United States Patent
Lo et al.

(10) Patent No.: US 8,563,242 B2
(45) Date of Patent: Oct. 22, 2013

(54) METHOD FOR DETECTING CHROMOSOMAL ANEUPLOIDY

(75) Inventors: Yuk Ming Dennis Lo, Kowloon (HK);
Rossa Wai Kwun Chiu, Shatin (HK);
Yu Kwan Tong, Tuen Mun (HK);
Shengnan Jin, Singapore (SG); Siu Chung Stephen Chim, Quarry Bay (HK); Wai Yi Tsui, Tsuen Wan (HK)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 64 days.

(21) Appl. No.: 12/833,460

(22) Filed: Jul. 9, 2010

(65) Prior Publication Data

US 2011/0039724 A1  Feb. 17, 2011

Related U.S. Application Data

(60) Provisional application No. 61/308,578, filed on Feb. 26, 2010, provisional application No. 61/233,042, filed on Aug. 11, 2009.

(51) Int. Cl.
*C12Q 1/68* (2006.01)
*C12Q 1/37* (2006.01)
*C12P 19/34* (2006.01)

(52) U.S. Cl.
USPC .......................... 435/6.1; 435/24.3; 435/91.1

(58) Field of Classification Search
None
See application file for complete search history.

(56) References Cited

FOREIGN PATENT DOCUMENTS

| WO | WO 2005/035725 A2 | 4/2005 |
|----|-------------------|--------|
| WO | WO 2006/097049 A1 | 9/2006 |
| WO | WO 2007/103910 A2 | 9/2007 |
| WO | WO 2007/132167 A2 | 11/2007 |

OTHER PUBLICATIONS

Tong et al., Noninvasive Prenatal Detection of Trisomy 21 by an Epigenetic—Genetic Chromosome-Dosage Approach, Molecular Diagnostics and Genetics, Clinical Chemistry 56:1, 90-98 (2010).*
Illanes et al., Detection of cell-fre fetal DNA in maternal urine, Prenatal Diagnosis, vol. 26, No. 13, pp. 1213-1218, 2006.*
YMD Lo, Noninvasive prenatal detection of fetal chromosomal aneuploidies by maternal plasma nucleic acid analysis: a review of the current state of the art, BJOG An International Journal of Obstetrics and Gynaecology, 2009;116:152-157.*
Poon et al., Differential DNA methylation between fetus and mother as a strategy for detecting fetal DNA in maternal plasma. Clin Chem 2002;48:35-41.*
International Search Report from PCT/GB2010/001327, dated Oct. 19, 2010.
Tong et al.; "Noninvasive prenatal detection of fetal trisomy 18 by epigenetic allelic ratio analysis in maternal plasma: Theoretical and empirical considerations"; *Clin. Chem.*; 52(12):2194-2202 (2006).

* cited by examiner

*Primary Examiner* — Jim Ketter
*Assistant Examiner* — Reza Ghafoorian
(74) *Attorney, Agent, or Firm* — Kilpatrick Townsend & Stockton LLP

(57) ABSTRACT

The present invention relates to a new, non-invasive method for detecting chromosomal aneuploidy by analyzing a sample from a pregnant woman. The detection is based on the ratio between the amount of a fetal methylation marker located on a chromosome relevant to the aneuploidy and the amount of a fetal genetic marker located on a reference chromosome, offering improved accuracy.

31 Claims, 21 Drawing Sheets

(A)
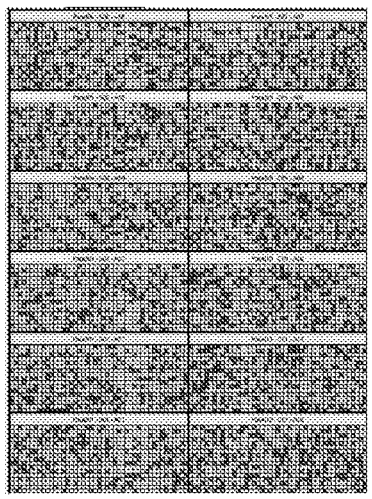
HLCS
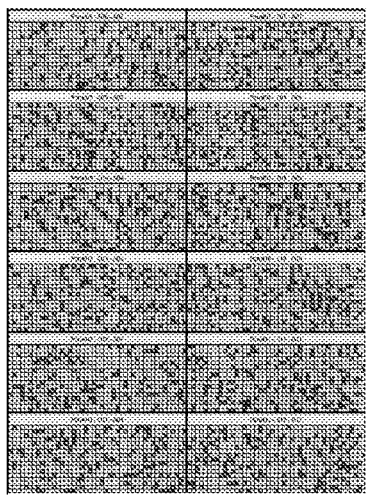
RASSF1A
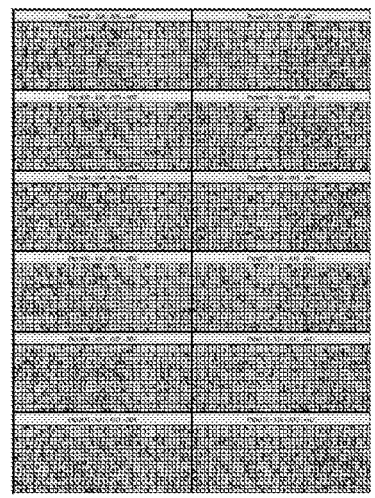
ZFX/Y
(B)
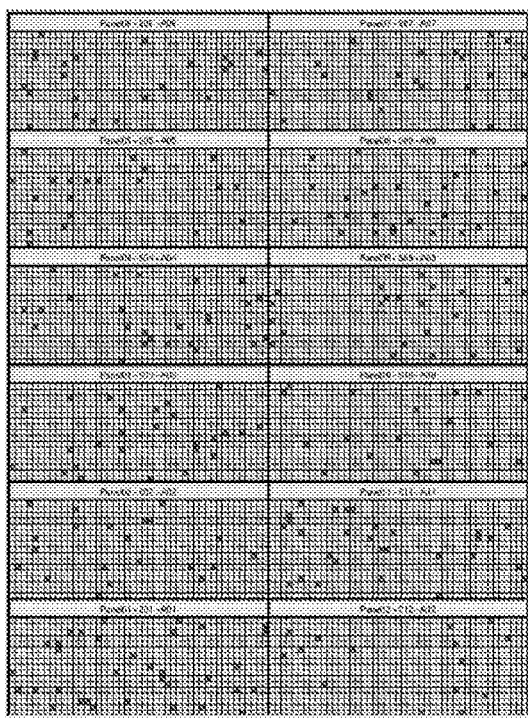
HLCS
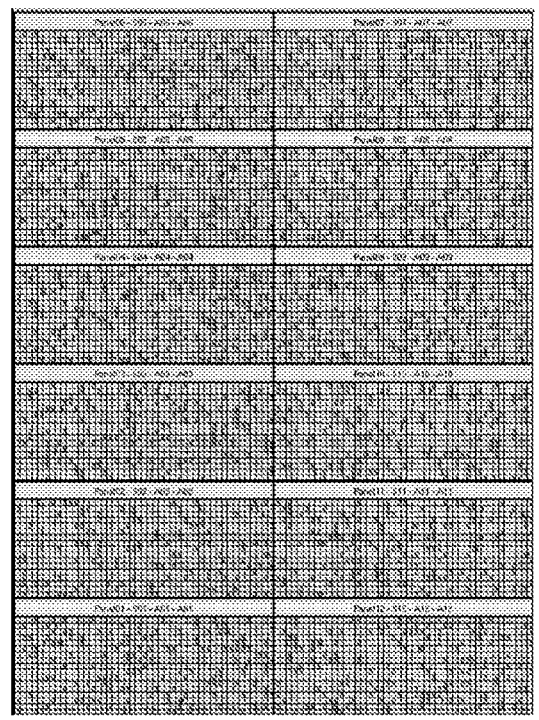
ZFX/Y
FIG. 2

HLCS

\>chr21:37274960-37275055    96bp

CCGTGTGGCCAGAGGTGgcaggggcgcggcctgagcggggctggggcgcg ggcaggatttggggctgcgccgagggggcgTCCCGACCTGGCCCTTT

RASSF1A

\>chr3:50353111-50353206    96bp

AGCTGGCACCCGCTGGcgcgctgggaagggccgcacccggctggagcgt gccaacgcgctgcgcatcgcgcggggcacCGCGTGCAACCCCACAC

ZFY

\>chrY:2889345+2889431    87bp

CAAGTGCTGGACTCAGATGTAACTGaagaagtttctttaccacactgcac agtcccagaTGATGTTTTAGCTTCTGACATTACTTCA

ZFX

\>chrX:24107448+24107534    87bp

CAAGTGCTGGACTCAGATGTAACTGaagaagtttctttagcacattgcac agtcccagaTGATGTTTTAGCTTCTGACATTACTTCA

FIG. 5

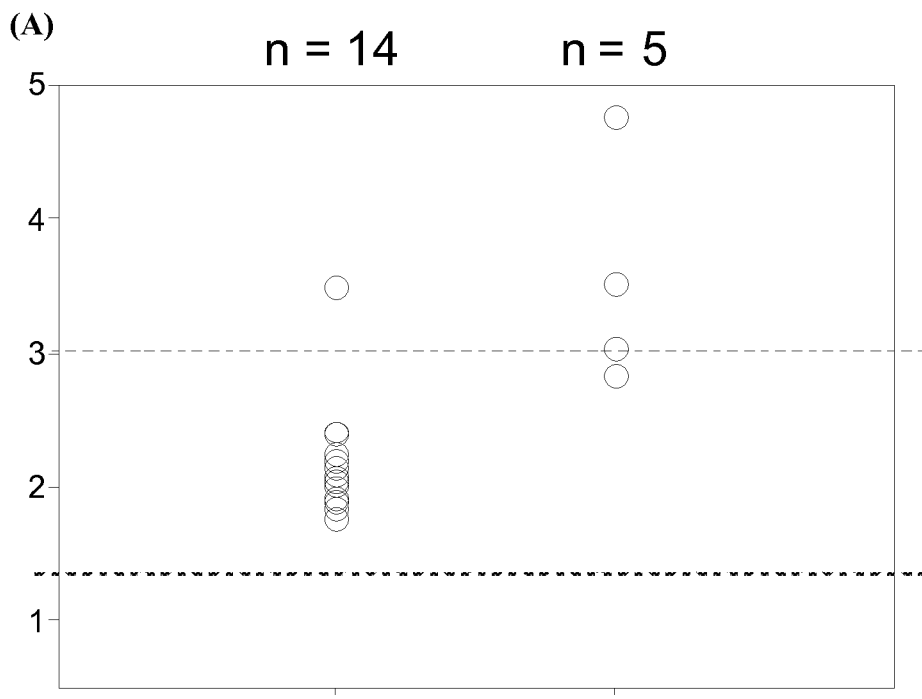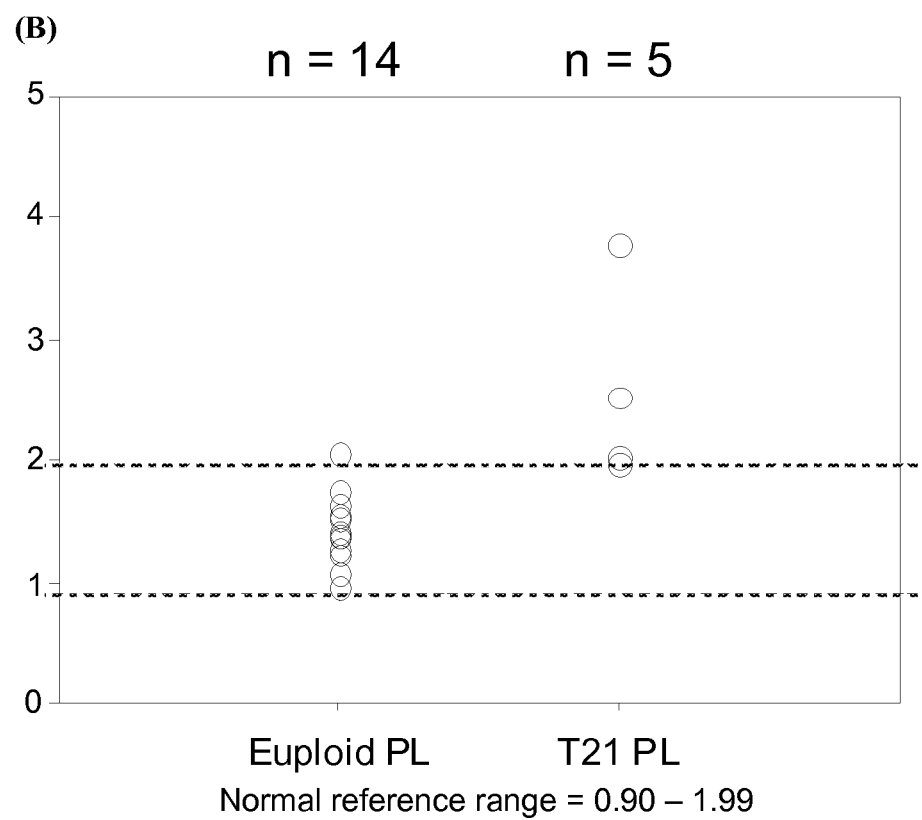
FIG. 10

| | | MI at CpG unit | | | | | | | | | |
|---|---|---|---|---|---|---|---|---|---|---|---|
| | | #1 | #2 | #3 | #4 | #5 | #6 | #7 | #8 | #9 | #10 |
| Euploid placental DNA | #1 | .25 | .33 | .33 | .31 | .31 | .21 | .31 | .39 | .39 | .33 |
| | #2 | .36 | .65 | .38 | .52 | .48 | .47 | .62 | .73 | .73 | .65 |
| | #3 | .71 | .77 | .63 | .75 | .72 | .62 | .76 | .80 | .80 | .77 |
| | #4 | .55 | .68 | .44 | .64 | .54 | .49 | .70 | .75 | .75 | .68 |
| | #5 | .55 | .68 | .50 | .67 | .63 | .54 | .71 | .75 | .75 | .68 |
| | #6 | .62 | .78 | .64 | .74 | .68 | .66 | .76 | .79 | .79 | .78 |
| T18 placental DNA | #1 | .56 | .75 | .50 | .73 | .63 | .52 | .75 | .72 | .72 | .75 |
| | #2 | .38 | .66 | .37 | .52 | .52 | .40 | .65 | .72 | .72 | .66 |
| | #3 | .41 | .67 | .36 | .48 | .46 | .42 | .63 | .71 | .71 | .67 |
| | #4 | .46 | .68 | .47 | .57 | .52 | .44 | .67 | .73 | .73 | .68 |
| | #5 | .54 | .70 | .43 | .63 | .57 | .44 | .67 | .75 | .75 | .70 |
| | #6 | .69 | .71 | .59 | .69 | .55 | .51 | .70 | .77 | .77 | .71 |
| Mann-Whitney Rank Sum Test | P-value | .94 | .94 | .59 | .59 | .59 | .24 | .59 | .39 | .39 | .94 |

Intensity Scale:
- $0.0 \leq MI < 0.2$
- $0.2 \leq MI < 0.4$
- $0.4 \leq MI < 0.6$
- $0.6 \leq MI < 0.8$
- $0.8 \leq MI \leq 1.0$

Beta-actin
Chromosomal location of CpG site (hg18)

Euploid placental tissues

| | chr7:5536443 | chr7:5536449 | chr7:5536458 Hpa II | chr7:5536463 Hin P1I | chr7:5536465 | chr7:5536472 | chr7:5536476 Hin P1I | chr7:5536478 | chr7:5536484 | chr7:5536486 Hin P1I | chr7:5536492 | chr7:5536500 | chr7:5536520 Hpa II | chr7:5536541 | chr7:5536543 | chr7:5536552 | chr7:5536555 | chr7:5536560 Hpa II | chr7:5536576 Hin P1I | chr7:5536583 | chr7:5536588 | Methylated site frequency |
|---|---|---|---|---|---|---|---|---|---|---|---|---|---|---|---|---|---|---|---|---|---|---|
| Case 1 | | | | | | | | | | | | | | | | | | | | | | |
| Methylation Index Case 2 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Methylation Index Case 3 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Methylation Index | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |

Euploid maternal blood cells

| | chr7:5536443 | chr7:5536449 | chr7:5536458 Hpa II | chr7:5536463 Hin P1I | chr7:5536465 | chr7:5536472 | chr7:5536476 Hin P1I | chr7:5536478 | chr7:5536484 | chr7:5536486 Hin P1I | chr7:5536492 | chr7:5536500 | chr7:5536520 Hpa II | chr7:5536541 | chr7:5536543 | chr7:5536552 | chr7:5536555 | chr7:5536560 Hpa II | chr7:5536576 Hin P1I | chr7:5536583 | chr7:5536588 | Methylated site frequency |
|---|---|---|---|---|---|---|---|---|---|---|---|---|---|---|---|---|---|---|---|---|---|---|
| Case 1 | | | | | | | | | | | | | | | | | | | | | | |
| Methylation Index Case 2 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Methylation Index Case 3 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Methylation Index | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |

|  | | MI at CpG unit | | | | |
|---|---|---|---|---|---|---|
|  | | #1 | #2 | #3 | #4 | #5 |
| Euploid placental DNA | #1 |  | 0.70 | 0.67 | 0.68 | 0.70 |
|  | #2 |  | 0.62 | 0.76 | 0.68 | 0.62 |
|  | #3 | 0.76 | 0.76 | 0.84 | 0.74 | 0.76 |
|  | #4 |  | 0.70 | 0.70 | 0.67 | 0.70 |
|  | #5 |  | 0.69 | 0.82 | 0.69 | 0.69 |
| T13 placental DNA | #1 |  | 0.76 | 0.85 | 0.68 | 0.76 |
|  | #2 |  | 0.86 | 0.85 | 0.80 | 0.86 |
|  | #3 |  | 0.74 | 0.91 | 0.68 | 0.74 |
|  | #4 |  | 0.76 | 0.80 | 0.67 | 0.76 |
|  | #5 | 0.68 | 0.79 | 0.85 | 0.75 | 0.79 |
| Mann-Whitney Rank Sum Test | $p$-value | 0.42 | 0.03 | 0.22 | 1.00 | 0.03 |

Intensity Scale: 0 to 1

*FIG. 19*

SEQUENCE LISTING

<160> NUMBER OF SEQ ID NOS: 151

<210> SEQ ID NO 1
<211> LENGTH: 601
<212> TYPE: DNA
<213> ORGANISM: Artificial Sequence
<220> FEATURE:
<223> OTHER INFORMATION: synthetic SNP rs6636 in transmembrane emp24
      protein transport domain containing 8 (TMED8) gene

<400> SEQUENCE: 1

```
gaagattttc caaactactt tatgtcattt agcttctatt ttctgaaggg ctttctttgg      60
tgccatgtac tcagatcagt cagttgactg aaagatgatc atgttttctt cgtaaagatt     120
taagcaattg gcaactacaa agacattatt ttcttactgt tctatatcat gtactgttgc     180
tgacattaca aaaagggtct ggaagggaaa ccgtgtcact gttttatctt ttttctttaa     240
aatacaaaag tatcccaact aatcatttat tatggtcagc ttgttttaca tgtcccctat     300
satgagaaat gctatcaaca tctgtgattt ctaagagtct taccaaattg ttactttaat     360
tcttgtgtcc tgctgagtgg ttttctttt aaaataccat ttttatcacc ctgtggcact     420
gggtgtgtta ctgcgattac actgatgatt ctgagctgtg cttcttcaag tagctcagtt     480
cttgcgtttt atattaggta acagttttgt gatgcttttg tgcattcttt gtcatctctt     540
ctgagttttc gaatctgtca taaataaact ttttcactat gcacctggta acatctgagt     600
t                                                                     601
```

<210> SEQ ID NO 2
<211> LENGTH: 201
<212> TYPE: DNA
<213> ORGANISM: Artificial Sequence
<220> FEATURE:
<223> OTHER INFORMATION: synthetic SNP rs6636 in transmembrane emp24
      protein transport domain containing 8 (TMED8) gene

<400> SEQUENCE: 2

```
ggaagggaaa ccgtgtcact gttttatctt ttttctttaa aatacaaaag tatcccaact      60
aatcatttat tatggtcagc ttgttttaca tgtcccctat satgagaaat gctatcaaca     120
tctgtgattt ctaagagtct taccaaattg ttactttaat tcttgtgtcc tgctgagtgg     180 ttttctttt aaaataccat t                                                201
```

```
<210> SEQ ID NO 3
<211> LENGTH: 96
<212> TYPE: DNA
<213> ORGANISM: Artificial Sequence
<220> FEATURE:
<223> OTHER INFORMATION: synthetic digital PCR assay (HLCS) genomic
      sequence, chr21:37274960-3775055

<400> SEQUENCE: 3
ccgtgtggcc agaggtggca ggggcgcggc ctgagcgggg ctggggcgcg ggcaggattt    60
ggggctgcgc cgagggggcgt cccgacctgg cccttt                            96

<210> SEQ ID NO 4
<211> LENGTH: 96
<212> TYPE: DNA
<213> ORGANISM: Artificial Sequence
<220> FEATURE:
<223> OTHER INFORMATION: synthetic digital PCR assay RASSF1A genomic
      sequence, chr3:50353111-50353206

<400> SEQUENCE: 4
agctggcacc cgctgggcgc gctgggaagg gccgcacccg gctggagcgt gccaacgcgc    60
tgcgcatcgc gcggggcacc gcgtgcaacc ccacac                             96

<210> SEQ ID NO 5
<211> LENGTH: 87
<212> TYPE: DNA
<213> ORGANISM: Artificial Sequence
<220> FEATURE:
<223> OTHER INFORMATION: synthetic digital PCR assay ZFY genomic
      sequence, chrY:2889345+2889431

<400> SEQUENCE: 5
caagtgctgg actcagatgt aactgaagaa gtttctttac cacactgcac agtcccagat    60
gatgttttag cttctgacat tacttca                                       87

<210> SEQ ID NO 6
<211> LENGTH: 87
<212> TYPE: DNA
<213> ORGANISM: Artificial Sequence
<220> FEATURE:
<223> OTHER INFORMATION: synthetic digital PCR assay ZFX genomic
      sequence, chrX:24107448+24107534

<400> SEQUENCE: 6
caagtgctgg actcagatgt aactgaagaa gtttctttag cacattgcac agtcccagat    60
gatgttttag cttctgacat tacttca                                       87

<210> SEQ ID NO 7
<211> LENGTH: 36
<212> TYPE: DNA
<213> ORGANISM: Artificial Sequence
<220> FEATURE:
<223> OTHER INFORMATION: synthetic PCR amplification forward primer
      targeting fetal trisomy 13 Marker 13A region

<400> SEQUENCE: 7
aggaagagag ggaggatagg aggagggagt tatagt                             36

<210> SEQ ID NO 8
<211> LENGTH: 60
<212> TYPE: DNA
<213> ORGANISM: Artificial Sequence
<220> FEATURE:
<223> OTHER INFORMATION: synthetic PCR amplification reverse primer
      targeting fetal trisomy 13 Marker 13A region
```

```
<400> SEQUENCE: 8
cagtaatacg actcactata gggagaaggc taaaattaca cacaatacac accaaaaaat    60

<210> SEQ ID NO 9
<211> LENGTH: 17
<212> TYPE: DNA
<213> ORGANISM: Artificial Sequence
<220> FEATURE:
<223> OTHER INFORMATION: synthetic conventional real-time PCR and
      digital PCR HLCS forward primer oligonucleotide

<400> SEQUENCE: 9
ccgtgtggcc agaggtg                                                  17

<210> SEQ ID NO 10
<211> LENGTH: 18
<212> TYPE: DNA
<213> ORGANISM: Artificial Sequence
<220> FEATURE:
<223> OTHER INFORMATION: synthetic conventional real-time PCR HLCS
      reverse primer oligonucleotide

<400> SEQUENCE: 10
tgggagccgg aacctacc                                                 18

<210> SEQ ID NO 11
<211> LENGTH: 20
<212> TYPE: DNA
<213> ORGANISM: Artificial Sequence
<220> FEATURE:
<223> OTHER INFORMATION: synthetic conventional real-time PCR HLCS
      TaqMan probe oligonucleotide
<220> FEATURE:
<221> NAME/KEY: modified_base
<222> LOCATION: (1)...(1)
<223> OTHER INFORMATION: t modified by 6-carboxyfluorescein (FAM)
<220> FEATURE:
<221> NAME/KEY: modified_base
<222> LOCATION: (20)...(20)
<223> OTHER INFORMATION: c modified by 6-carboxytetramethylrhodamine
      (TAMRA)

<400> SEQUENCE: 11
tcccgacctg gcccttcgcc                                               20

<210> SEQ ID NO 12
<211> LENGTH: 17
<212> TYPE: DNA
<213> ORGANISM: Artificial Sequence
<220> FEATURE:
<223> OTHER INFORMATION: synthetic conventional real-time PCR and
      digital PCR HLCS reverse primer oligonucleotide

<400> SEQUENCE: 12
aaagggccag gtcggga                                                  17

<210> SEQ ID NO 13
<211> LENGTH: 17
<212> TYPE: DNA
<213> ORGANISM: Artificial Sequence
<220> FEATURE:
<223> OTHER INFORMATION: synthetic conventional real-time PCR and
      digital PCR HLCS TaqMan probe oligonucleotide
<220> FEATURE:
<221> NAME/KEY: modified_base
<222> LOCATION: (1)...(1)
<223> OTHER INFORMATION: a modified by 6-carboxyfluorescein (FAM)
<220> FEATURE:
<221> NAME/KEY: modified_base
```

-continued

```
<222> LOCATION: (17)...(17)
<223> OTHER INFORMATION: c modified by minor-groove binder (MGB)

<400> SEQUENCE: 13
aggatttggg gctgcgc                                                        17

<210> SEQ ID NO 14
<211> LENGTH: 16
<212> TYPE: DNA
<213> ORGANISM: Artificial Sequence
<220> FEATURE:
<223> OTHER INFORMATION: synthetic conventional real-time PCR and
      digital PCR RASSF1A forward primer oligonucleotide

<400> SEQUENCE: 14
agctggcacc cgctgg                                                         16

<210> SEQ ID NO 15
<211> LENGTH: 17
<212> TYPE: DNA
<213> ORGANISM: Artificial Sequence
<220> FEATURE:
<223> OTHER INFORMATION: synthetic conventional real-time PCR and
      digital PCR RASSF1A reverse primer oligonucleotide

<400> SEQUENCE: 15
gtgtggggtt gcacgcg                                                        17

<210> SEQ ID NO 16
<211> LENGTH: 15
<212> TYPE: DNA
<213> ORGANISM: Artificial Sequence
<220> FEATURE:
<223> OTHER INFORMATION: synthetic conventional real-time PCR and
      digital PCR RASSF1A TaqMan probe oligonucleotide
<220> FEATURE:
<221> NAME/KEY: modified_base
<222> LOCATION: (1)...(1)
<223> OTHER INFORMATION: a modified by Applied Biosystems proprietary
      dye VIC
<220> FEATURE:
<221> NAME/KEY: modified_base
<222> LOCATION: (15)...(15)
<223> OTHER INFORMATION: t modified by minor-groove binder (MGB)

<400> SEQUENCE: 16
acccggctgg agcgt                                                          15

<210> SEQ ID NO 17
<211> LENGTH: 25
<212> TYPE: DNA
<213> ORGANISM: Artificial Sequence
<220> FEATURE:
<223> OTHER INFORMATION: synthetic conventional real-time PCR and
      digital PCR ZFX/Y forward primer oligonucleotide

<400> SEQUENCE: 17
caagtgctgg actcagatgt aactg                                               25

<210> SEQ ID NO 18
<211> LENGTH: 28
<212> TYPE: DNA
<213> ORGANISM: Artificial Sequence
<220> FEATURE:
<223> OTHER INFORMATION: synthetic conventional real-time PCR and
      digital PCR ZFX/Y reverse primer oligonucleotide

<400> SEQUENCE: 18
tgaagtaatg tcagaagcta aaacatca                                            28
```

<210> SEQ ID NO 19
<211> LENGTH: 17
<212> TYPE: DNA
<213> ORGANISM: Artificial Sequence
<220> FEATURE:
<223> OTHER INFORMATION: synthetic conventional real-time PCR and
      digital PCR ZFX/Y TaqMan probe_ZFY oligonucleotide
<220> FEATURE:
<221> NAME/KEY: modified_base
<222> LOCATION: (1)...(1)
<223> OTHER INFORMATION: t modified by 6-carboxyfluorescein
<220> FEATURE:
<221> NAME/KEY: modified_base
<222> LOCATION: (17)...(17)
<223> OTHER INFORMATION: c modified by minor-groove binder (MGB)

<400> SEQUENCE: 19
tctttaccac actgcac                                                17

<210> SEQ ID NO 20
<211> LENGTH: 16
<212> TYPE: DNA
<213> ORGANISM: Artificial Sequence
<220> FEATURE:
<223> OTHER INFORMATION: synthetic conventional real-time PCR and
      digital PCR ZFX/Y TaqMan probe_ZFX oligonucleotide
<220> FEATURE:
<221> NAME/KEY: modified_base
<222> LOCATION: (1)...(1)
<223> OTHER INFORMATION: t modified by Applied Biosystems proprietary
      dye VIC
<220> FEATURE:
<221> NAME/KEY: modified_base
<222> LOCATION: (16)...(16)
<223> OTHER INFORMATION: a modified by minor-groove binder (MGB)

<400> SEQUENCE: 20
tctttagcac attgca                                                 16

<210> SEQ ID NO 21
<211> LENGTH: 31
<212> TYPE: DNA
<213> ORGANISM: Artificial Sequence
<220> FEATURE:
<223> OTHER INFORMATION: synthetic PCR amplification F-primer for
      collagen, type VI, alpha 1 (COL6A1)

<400> SEQUENCE: 21
gtgttggata gtttagagag tattggtttg t                                31

<210> SEQ ID NO 22
<211> LENGTH: 22
<212> TYPE: DNA
<213> ORGANISM: Artificial Sequence
<220> FEATURE:
<223> OTHER INFORMATION: synthetic PCR amplification R-primer for
      collagen, type VI, alpha 1 (COL6A1)

<400> SEQUENCE: 22
aaacccacac ccaacactca aa                                          22

<210> SEQ ID NO 23
<211> LENGTH: 29
<212> TYPE: DNA
<213> ORGANISM: Artificial Sequence
<220> FEATURE:
<223> OTHER INFORMATION: synthetic PCR amplification F-primer for
      formamino transferase cyclodeaminase, formamino
      tetrahydrofolate cyclodeaminase (FTCD) combined
      bisulfite restriction analysis (COBRA) region A

```
<400> SEQUENCE: 23
agggttatty gtagtggtat agggaggtt                                        29

<210> SEQ ID NO 24
<211> LENGTH: 26
<212> TYPE: DNA
<213> ORGANISM: Artificial Sequence
<220> FEATURE:
<223> OTHER INFORMATION: synthetic PCR amplification R-primer for
      formamino transferase cyclodeaminase, formamino
      tetrahydrofolate cyclodeaminase (FTCD) combined
      bisulfite restriction analysis (COBRA) region A

<400> SEQUENCE: 24
caccracttc tcattaacca acaaaa                                           26

<210> SEQ ID NO 25
<211> LENGTH: 36
<212> TYPE: DNA
<213> ORGANISM: Artificial Sequence
<220> FEATURE:
<223> OTHER INFORMATION: synthetic PCR amplification F-primer for
      formamino transferase cyclodeaminase, formamino
      tetrahydrofolate cyclodeaminase (FTCD) combined
      bisulfite restriction analysis (COBRA) region B

<400> SEQUENCE: 25 gtaatttta gatggaatag aaaattgtat tttttt                                 36

<210> SEQ ID NO 26
<211> LENGTH: 30
<212> TYPE: DNA
<213> ORGANISM: Artificial Sequence
<220> FEATURE:
<223> OTHER INFORMATION: synthetic PCR amplification R-primer for
      formamino transferase cyclodeaminase, formamino
      tetrahydrofolate cyclodeaminase (FTCD) combined
      bisulfite restriction analysis (COBRA) region B

<400> SEQUENCE: 26
taatctccct aaacaaatct taaccaaaaa                                       30

<210> SEQ ID NO 27
<211> LENGTH: 27
<212> TYPE: DNA
<213> ORGANISM: Artificial Sequence
<220> FEATURE:
<223> OTHER INFORMATION: synthetic PCR amplification F-primer for
      formamino transferase cyclodeaminase, formamino
      tetrahydrofolate cyclodeaminase (FTCD) combined
      bisulfite restriction analysis (COBRA) region C

<400> SEQUENCE: 27
tggggtgtag tgtgtttatt gtttgtt                                          27

<210> SEQ ID NO 28
<211> LENGTH: 26
<212> TYPE: DNA
<213> ORGANISM: Artificial Sequence
<220> FEATURE:
<223> OTHER INFORMATION: synthetic PCR amplification R-primer for
      formamino transferase cyclodeaminase, formamino
      tetrahydrofolate cyclodeaminase (FTCD) combined
      bisulfite restriction analysis (COBRA) region C

<400> SEQUENCE: 28
aaatctccct acctaactca acccaa                                           26
```

<210> SEQ ID NO 29
<211> LENGTH: 29
<212> TYPE: DNA
<213> ORGANISM: Artificial Sequence
<220> FEATURE:
<223> OTHER INFORMATION: synthetic PCR amplification F-primer for
      lanosterol synthase (2,3-oxidosqualene-lanosterol
      cyclase) (LSS)

<400> SEQUENCE: 29
tttgtaggat tgtttgtgta gaggttttt                                    29

<210> SEQ ID NO 30
<211> LENGTH: 26
<212> TYPE: DNA
<213> ORGANISM: Artificial Sequence
<220> FEATURE:
<223> OTHER INFORMATION: synthetic PCR amplification R-primer for
      lanosterol synthase (2,3-oxidosqualene-lanosterol
      cyclase) (LSS)

<400> SEQUENCE: 30
tcctctctac attcactcaa cccaaa                                       26

<210> SEQ ID NO 31
<211> LENGTH: 30
<212> TYPE: DNA
<213> ORGANISM: Artificial Sequence
<220> FEATURE:
<223> OTHER INFORMATION: synthetic PCR amplification F-primer for
      C21orf81 (ankyrin repeat domain family, member A3
      pseudogene) combined bisulfite restriction
      analysis (COBRA) region A

<400> SEQUENCE: 31
ggttaggggt agtattyggt ggtatattgt                                   30

<210> SEQ ID NO 32
<211> LENGTH: 28
<212> TYPE: DNA
<213> ORGANISM: Artificial Sequence
<220> FEATURE:
<223> OTHER INFORMATION: synthetic PCR amplification R-primer for
      C21orf81 (ankyrin repeat domain family, member A3
      pseudogene) combined bisulfite restriction
      analysis (COBRA) region A

<400> SEQUENCE: 32
ccrccacaaa caatacaaca actaataa                                     28

<210> SEQ ID NO 33
<211> LENGTH: 25
<212> TYPE: DNA
<213> ORGANISM: Artificial Sequence
<220> FEATURE:
<223> OTHER INFORMATION: synthetic PCR amplification F-primer for
      C21orf81 (ankyrin repeat domain family, member A3
      pseudogene) combined bisulfite restriction
      analysis (COBRA) region B

<400> SEQUENCE: 33
ggagttgtyg ggggttaagt tgttt                                        25

<210> SEQ ID NO 34
<211> LENGTH: 19
<212> TYPE: DNA
<213> ORGANISM: Artificial Sequence
<220> FEATURE:
<223> OTHER INFORMATION: synthetic PCR amplification R-primer for

```
            C21orf81 (ankyrin repeat domain family, member A3
            pseudogene) combined bisulfite restriction
            analysis (COBRA) region B

<400> SEQUENCE: 34
tcccccaacc taccccta                                                    19

<210> SEQ ID NO 35
<211> LENGTH: 37
<212> TYPE: DNA
<213> ORGANISM: Artificial Sequence
<220> FEATURE:
<223> OTHER INFORMATION: synthetic PCR amplification F-primer for
      C21orf81 (ankyrin repeat domain family, member A3
      pseudogene) combined bisulfite restriction
      analysis (COBRA) region C

<400> SEQUENCE: 35
ggttttagta atattagtgg tttataaaga aggagtt                               37

<210> SEQ ID NO 36
<211> LENGTH: 22
<212> TYPE: DNA
<213> ORGANISM: Artificial Sequence
<220> FEATURE:
<223> OTHER INFORMATION: synthetic PCR amplification R-primer for
      C21orf81 (ankyrin repeat domain family, member A3
      pseudogene) combined bisulfite restriction
      analysis (COBRA) region C

<400> SEQUENCE: 36
ratccaccac aaccttcaac aa                                               22

<210> SEQ ID NO 37
<211> LENGTH: 26
<212> TYPE: DNA
<213> ORGANISM: Artificial Sequence
<220> FEATURE:
<223> OTHER INFORMATION: synthetic PCR amplification F-primer for
      C21orf81 (ankyrin repeat domain family, member A3
      pseudogene) combined bisulfite restriction
      analysis (COBRA) region D

<400> SEQUENCE: 37
aggtgaaaag gtgataggga gttgtt                                           26

<210> SEQ ID NO 38
<211> LENGTH: 24
<212> TYPE: DNA
<213> ORGANISM: Artificial Sequence
<220> FEATURE:
<223> OTHER INFORMATION: synthetic PCR amplification R-primer for
      C21orf81 (ankyrin repeat domain family, member A3
      pseudogene) combined bisulfite restriction
      analysis (COBRA) region D

<400> SEQUENCE: 38
ctccaccaac tactccaacc aaaa                                             24

<210> SEQ ID NO 39
<211> LENGTH: 30
<212> TYPE: DNA
<213> ORGANISM: Artificial Sequence
<220> FEATURE:
<223> OTHER INFORMATION: synthetic PCR amplification F-primer for
      C21orf30, clone DKFZp434C128 hypotetical protein combined
      bisulfite restriction analysis (COBRA) region A

<400> SEQUENCE: 39
```

```
ggatgtatag gtgaatgatt ggtgttattt                                    30
```

<210> SEQ ID NO 40
<211> LENGTH: 29
<212> TYPE: DNA
<213> ORGANISM: Artificial Sequence
<220> FEATURE:
<223> OTHER INFORMATION: synthetic PCR amplification R-primer for
      C21orf30, clone DKFZp434C128 hypotetical protein combined
      bisulfite restriction analysis (COBRA) region A

<400> SEQUENCE: 40

```
aaaactaact aacacccaca aaacacaaa                                     29
```

<210> SEQ ID NO 41
<211> LENGTH: 26
<212> TYPE: DNA
<213> ORGANISM: Artificial Sequence
<220> FEATURE:
<223> OTHER INFORMATION: synthetic PCR amplification F-primer for
      C21orf30, clone DKFZp434C128 hypotetical protein combined
      bisulfite restriction analysis (COBRA) region B

<400> SEQUENCE: 41

```
ggggttgtttt agtttagggt ttggtt                                       26
```

<210> SEQ ID NO 42
<211> LENGTH: 27
<212> TYPE: DNA
<213> ORGANISM: Artificial Sequence
<220> FEATURE:
<223> OTHER INFORMATION: synthetic PCR amplification R-primer for
      C21orf30, clone DKFZp434C128 hypotetical protein combined
      bisulfite restriction analysis (COBRA) region B

<400> SEQUENCE: 42

```
caaacaccca crataaaaac tccaata                                       27
```

<210> SEQ ID NO 43
<211> LENGTH: 31
<212> TYPE: DNA
<213> ORGANISM: Artificial Sequence
<220> FEATURE:
<223> OTHER INFORMATION: synthetic PCR amplification F-primer for
      C21orf87, RNA 257

<400> SEQUENCE: 43

```
aaaatttttt tgttttgtta ggttttttgat t                                 31
```

<210> SEQ ID NO 44
<211> LENGTH: 36
<212> TYPE: DNA
<213> ORGANISM: Artificial Sequence
<220> FEATURE:
<223> OTHER INFORMATION: synthetic PCR amplification R-primer for
      C21orf87, RNA 257

<400> SEQUENCE: 44

```
ccacaaatta taacttactc aaaatcaaac taataa                             36
```

<210> SEQ ID NO 45
<211> LENGTH: 35
<212> TYPE: DNA
<213> ORGANISM: Artificial Sequence
<220> FEATURE:
<223> OTHER INFORMATION: synthetic PCR amplification F-primer for
      C21orf18 (C21orf27), SET domain containing 4 (SETD4)

<400> SEQUENCE: 45
gggtagtata aaggtagtat taggaatagg ggttt                    35

<210> SEQ ID NO 46
<211> LENGTH: 31
<212> TYPE: DNA
<213> ORGANISM: Artificial Sequence
<220> FEATURE:
<223> OTHER INFORMATION: synthetic PCR amplification R-primer for
      C21orf18 (C21orf27), SET domain containing 4 (SETD4)

<400> SEQUENCE: 46
actcatccac cttatctcaa aacaacaata a                        31

<210> SEQ ID NO 47
<211> LENGTH: 30
<212> TYPE: DNA
<213> ORGANISM: Artificial Sequence
<220> FEATURE:
<223> OTHER INFORMATION: synthetic PCR amplification F-primer for
      potassium inwardly-rectifying channel, subfamily J, member
      15 (KCNJ15)

<400> SEQUENCE: 47
gtattgtttt tggattagtg tagagggttt                          30

<210> SEQ ID NO 48
<211> LENGTH: 33
<212> TYPE: DNA
<213> ORGANISM: Artificial Sequence
<220> FEATURE:
<223> OTHER INFORMATION: synthetic PCR amplification R-primer for
      potassium inwardly-rectifying channel, subfamily J, member
      15 (KCNJ15)

<400> SEQUENCE: 48
caaaattcca tccttaaaaa aaacttctaa taa                      33

<210> SEQ ID NO 49
<211> LENGTH: 39
<212> TYPE: DNA
<213> ORGANISM: Artificial Sequence
<220> FEATURE:
<223> OTHER INFORMATION: synthetic PCR amplification F-primer for Down
      syndrome critical region gene 9 (DSCR9) combined
      bisulfite restriction analysis (COBRA) region A

<400> SEQUENCE: 49
gtgaygtaat aatttaaatt atgaagaggt aatagagtt                39

<210> SEQ ID NO 50
<211> LENGTH: 20
<212> TYPE: DNA
<213> ORGANISM: Artificial Sequence
<220> FEATURE:
<223> OTHER INFORMATION: synthetic PCR amplification R-primer for Down
      syndrome critical region gene 9 (DSCR9) combined
      bisulfite restriction analysis (COBRA) region A

<400> SEQUENCE: 50
ccccaccrtt ccatcccaaa                                     20

<210> SEQ ID NO 51
<211> LENGTH: 29
<212> TYPE: DNA
<213> ORGANISM: Artificial Sequence
<220> FEATURE:
<223> OTHER INFORMATION: synthetic PCR amplification F-primer for Down
      syndrome critical region gene 9 (DSCR9) combined -continued bisulfite restriction analysis (COBRA) region B

<400> SEQUENCE: 51
gygttaggtt atgttggggt tgtattatt                29

<210> SEQ ID NO 52
<211> LENGTH: 23
<212> TYPE: DNA
<213> ORGANISM: Artificial Sequence
<220> FEATURE:
<223> OTHER INFORMATION: synthetic PCR amplification R-primer for Down
      syndrome critical region gene 9 (DSCR9) combined
      bisulfite restriction analysis (COBRA) region B

<400> SEQUENCE: 52
acaaccraaa aacaccaccc taa                23

<210> SEQ ID NO 53
<211> LENGTH: 27
<212> TYPE: DNA
<213> ORGANISM: Artificial Sequence
<220> FEATURE:
<223> OTHER INFORMATION: synthetic PCR amplification F-primer for
      C21orf125 (LOC100430175) combined bisulfite restriction
      analysis (COBRA) region A

<400> SEQUENCE: 53
ttaatagtat taagggtggg tgggttt                27

<210> SEQ ID NO 54
<211> LENGTH: 36
<212> TYPE: DNA
<213> ORGANISM: Artificial Sequence
<220> FEATURE:
<223> OTHER INFORMATION: synthetic PCR amplification R-primer for
      C21orf125 (LOC100430175) combined bisulfite restriction
      analysis (COBRA) region A

<400> SEQUENCE: 54
ctacctaaca taaaaatatt aattcttccc tatcta                36

<210> SEQ ID NO 55
<211> LENGTH: 25
<212> TYPE: DNA
<213> ORGANISM: Artificial Sequence
<220> FEATURE:
<223> OTHER INFORMATION: synthetic PCR amplification F-primer for
      C21orf125 (LOC100430175) combined bisulfite restriction
      analysis (COBRA) region B

<400> SEQUENCE: 55
gtatggttag gtaggaggtg gggtt                25

<210> SEQ ID NO 56
<211> LENGTH: 29
<212> TYPE: DNA
<213> ORGANISM: Artificial Sequence
<220> FEATURE:
<223> OTHER INFORMATION: synthetic PCR amplification R-primer for
      C21orf125 (LOC100430175) combined bisulfite restriction
      analysis (COBRA) region B

<400> SEQUENCE: 56
caataccaaa ttaaaataaa tccccaaaa                29

<210> SEQ ID NO 57
<211> LENGTH: 24
<212> TYPE: DNA

```
<213> ORGANISM: Artificial Sequence
<220> FEATURE:
<223> OTHER INFORMATION: synthetic PCR amplification F-primer for Down
      syndrome cell adhesion molecule isoform CHD2-42
      (DSCAM) combined bisulfite restriction analysis
      (COBRA) region A

<400> SEQUENCE: 57
ggttgggtag ygtgtggagt tgtt                                              24

<210> SEQ ID NO 58
<211> LENGTH: 27
<212> TYPE: DNA
<213> ORGANISM: Artificial Sequence
<220> FEATURE:
<223> OTHER INFORMATION: synthetic PCR amplification R-primer for Down
      syndrome cell adhesion molecule isoform CHD2-42
      (DSCAM) combined bisulfite restriction analysis
      (COBRA) region A

<400> SEQUENCE: 58
rataaaaacc aacaccacct ttacaaa                                           27

<210> SEQ ID NO 59
<211> LENGTH: 24
<212> TYPE: DNA
<213> ORGANISM: Artificial Sequence
<220> FEATURE:
<223> OTHER INFORMATION: synthetic PCR amplification F-primer for Down
      syndrome cell adhesion molecule isoform CHD2-42
      (DSCAM) combined bisulfite restriction analysis
      (COBRA) region B

<400> SEQUENCE: 59
ggttgggtag ygtgtggagt tgtt                                              24

<210> SEQ ID NO 60
<211> LENGTH: 39
<212> TYPE: DNA
<213> ORGANISM: Artificial Sequence
<220> FEATURE:
<223> OTHER INFORMATION: synthetic PCR amplification R-primer for Down
      syndrome cell adhesion molecule isoform CHD2-42
      (DSCAM) combined bisulfite restriction analysis
      (COBRA) region B

<400> SEQUENCE: 60
aactacaaaa aaaacataaa aatttactta taacaaaaa                              39

<210> SEQ ID NO 61
<211> LENGTH: 28
<212> TYPE: DNA
<213> ORGANISM: Artificial Sequence
<220> FEATURE:
<223> OTHER INFORMATION: synthetic PCR amplification F-primer for zinc
      finger protein 294 (ZNF294), ring finger protein
      160 (RNF160)  combined bisulfite restriction
      analysis (COBRA) region A

<400> SEQUENCE: 61
gggtttaatg tttggttttt tattggtt                                          28

<210> SEQ ID NO 62
<211> LENGTH: 31
<212> TYPE: DNA
<213> ORGANISM: Artificial Sequence
<220> FEATURE:
<223> OTHER INFORMATION: synthetic PCR amplification R-primer for zinc
      finger protein 294 (ZNF294), ring finger protein
      160 (RNF160)  combined bisulfite restriction
```

-continued analysis (COBRA) region A

<400> SEQUENCE: 62
cccataatcr crattacaac tatactctaa a                                31

<210> SEQ ID NO 63
<211> LENGTH: 26
<212> TYPE: DNA
<213> ORGANISM: Artificial Sequence
<220> FEATURE:
<223> OTHER INFORMATION: synthetic PCR amplification F-primer for zinc
      finger protein 294 (ZNF294), ring finger protein
      160 (RNF160) combined bisulfite restriction
      analysis (COBRA) region B

<400> SEQUENCE: 63
aygtgttaat yggggtttga gtgttt                                      26

<210> SEQ ID NO 64
<211> LENGTH: 24
<212> TYPE: DNA
<213> ORGANISM: Artificial Sequence
<220> FEATURE:
<223> OTHER INFORMATION: synthetic PCR amplification R-primer for zinc
      finger protein 294 (ZNF294), ring finger protein
      160 (RNF160) combined bisulfite restriction
      analysis (COBRA) region B

<400> SEQUENCE: 64
cacrattccc caatctactc aaaa                                        24

<210> SEQ ID NO 65
<211> LENGTH: 24
<212> TYPE: DNA
<213> ORGANISM: Artificial Sequence
<220> FEATURE:
<223> OTHER INFORMATION: synthetic PCR amplification F-primer for
      chloride intracellular channel 6 (CLIC6)

<400> SEQUENCE: 65
gagggaggag gggaagataa attt                                        24

<210> SEQ ID NO 66
<211> LENGTH: 29
<212> TYPE: DNA
<213> ORGANISM: Artificial Sequence
<220> FEATURE:
<223> OTHER INFORMATION: synthetic PCR amplification R-primer for
      chloride intracellular channel 6 (CLIC6)

<400> SEQUENCE: 66
aactccctaa actcttcctc cactactaa                                   29

<210> SEQ ID NO 67
<211> LENGTH: 28
<212> TYPE: DNA
<213> ORGANISM: Artificial Sequence
<220> FEATURE:
<223> OTHER INFORMATION: synthetic PCR amplification F-primer for 39S
      mitochondrial ribosomal protein L39 (MRPL39,
      L39mt) combined bisulfite restriction analysis
      (COBRA) region A

<400> SEQUENCE: 67
ggggaygtgt ttygaggttt ttattatt                                    28

<210> SEQ ID NO 68
<211> LENGTH: 24

```
<212> TYPE: DNA
<213> ORGANISM: Artificial Sequence
<220> FEATURE:
<223> OTHER INFORMATION: synthetic PCR amplification R-primer for 39S
      mitochondrial ribosomal protein L39 (MRPL39,
      L39mt) combined bisulfite restriction analysis
      (COBRA) region A

<400> SEQUENCE: 68
crcccaccac rtaaactcta caaa                                              24

<210> SEQ ID NO 69
<211> LENGTH: 23
<212> TYPE: DNA
<213> ORGANISM: Artificial Sequence
<220> FEATURE:
<223> OTHER INFORMATION: synthetic PCR amplification F-primer for 39S
      mitochondrial ribosomal protein L39 (MRPL39,
      L39mt) combined bisulfite restriction analysis
      (COBRA) region B

<400> SEQUENCE: 69
tggaggygtt ggttatgggt ttt                                               23

<210> SEQ ID NO 70
<211> LENGTH: 29
<212> TYPE: DNA
<213> ORGANISM: Artificial Sequence
<220> FEATURE:
<223> OTHER INFORMATION: synthetic PCR amplification R-primer for 39S
      mitochondrial ribosomal protein L39 (MRPL39,
      L39mt) combined bisulfite restriction analysis
      (COBRA) region B

<400> SEQUENCE: 70
ttcccataaa ttaatcctcc caaactata                                         29

<210> SEQ ID NO 71
<211> LENGTH: 33
<212> TYPE: DNA
<213> ORGANISM: Artificial Sequence
<220> FEATURE:
<223> OTHER INFORMATION: synthetic PCR amplification F-primer for
      holocarboxylase synthetase (biotin-(proprionyl-CoA-carboxylase
      (ATP-hydrolyzing)) ligase) (HLCS) combined
      bisulfite restriction analysis (COBRA) region A

<400> SEQUENCE: 71
ggagtgttaa atttggttat ttttgtttgt tat                                    33

<210> SEQ ID NO 72
<211> LENGTH: 28
<212> TYPE: DNA
<213> ORGANISM: Artificial Sequence
<220> FEATURE:
<223> OTHER INFORMATION: synthetic PCR amplification R-primer for
      holocarboxylase synthetase (biotin-(proprionyl-CoA-carboxylase
      (ATP-hydrolyzing)) ligase) (HLCS) combined
      bisulfite restriction analysis (COBRA) region A

<400> SEQUENCE: 72 crctacccttt ctccactaac tactcaaa                                         28

<210> SEQ ID NO 73
<211> LENGTH: 29
<212> TYPE: DNA
<213> ORGANISM: Artificial Sequence
<220> FEATURE:
<223> OTHER INFORMATION: synthetic PCR amplification F-primer for
      holocarboxylase synthetase (biotin-(proprionyl-CoA-carboxylase
```

(ATP-hydrolyzing)) ligase) (HLCS) combined
bisulfite restriction analysis (COBRA) region B1

<400> SEQUENCE: 73
aggagttaga ygttttagtt ygtgtggtt                                              29

<210> SEQ ID NO 74
<211> LENGTH: 22
<212> TYPE: DNA
<213> ORGANISM: Artificial Sequence
<220> FEATURE:
<223> OTHER INFORMATION: synthetic PCR amplification R-primer for
      holocarboxylase synthetase (biotin-(proprionyl-CoA-carboxylase
      (ATP-hydrolyzing)) ligase) (HLCS) combined
      bisulfite restriction analysis (COBRA) region B1

<400> SEQUENCE: 74
ctaaacaccc raatccccaa aa                                                     22

<210> SEQ ID NO 75
<211> LENGTH: 27
<212> TYPE: DNA
<213> ORGANISM: Artificial Sequence
<220> FEATURE:
<223> OTHER INFORMATION: synthetic PCR amplification F-primer for
      holocarboxylase synthetase (biotin-(proprionyl-CoA-carboxylase
      (ATP-hydrolyzing)) ligase) (HLCS) combined
      bisulfite restriction analysis (COBRA) region B2

<400> SEQUENCE: 75
gttttagtty gtgtggttag aggtggt                                                27

<210> SEQ ID NO 76
<211> LENGTH: 31
<212> TYPE: DNA
<213> ORGANISM: Artificial Sequence
<220> FEATURE:
<223> OTHER INFORMATION: synthetic PCR amplification R-primer for
      holocarboxylase synthetase (biotin-(proprionyl-CoA-carboxylase
      (ATP-hydrolyzing)) ligase) (HLCS) combined
      bisulfite restriction analysis (COBRA) region B2

<400> SEQUENCE: 76
ctaaaaaata aaaacaaaa tccaaaacaa a                                            31

<210> SEQ ID NO 77
<211> LENGTH: 36
<212> TYPE: DNA
<213> ORGANISM: Artificial Sequence
<220> FEATURE:
<223> OTHER INFORMATION: synthetic PCR amplification F-primer for
      C21orf4 hypothetical protein combined bisulfite
      restriction analysis (COBRA) region A

<400> SEQUENCE: 77 gtttttatt tttgagattt agaatttgat ttattt                                       36

<210> SEQ ID NO 78
<211> LENGTH: 24
<212> TYPE: DNA
<213> ORGANISM: Artificial Sequence
<220> FEATURE:
<223> OTHER INFORMATION: synthetic PCR amplification R-primer for
      C21orf4 hypothetical protein combined bisulfite
      restriction analysis (COBRA) region A

<400> SEQUENCE: 78
aaaaatttca ctttctcccc caaa                                                   24

```
<210> SEQ ID NO 79
<211> LENGTH: 31
<212> TYPE: DNA
<213> ORGANISM: Artificial Sequence
<220> FEATURE:
<223> OTHER INFORMATION: synthetic PCR amplification F-primer for
      C21orf4 hypothetical protein combined bisulfite
      restriction analysis (COBRA) region B

<400> SEQUENCE: 79
ttagtagaga ygggatttta ttatgttggt t                                          31

<210> SEQ ID NO 80
<211> LENGTH: 40
<212> TYPE: DNA
<213> ORGANISM: Artificial Sequence
<220> FEATURE:
<223> OTHER INFORMATION: synthetic PCR amplification R-primer for
      C21orf4 hypothetical protein combined bisulfite
      restriction analysis (COBRA) region B

<400> SEQUENCE: 80
aaaaaaaaaa aaatcatata cctaaataac tataaaata                                  40

<210> SEQ ID NO 81
<211> LENGTH: 33
<212> TYPE: DNA
<213> ORGANISM: Artificial Sequence
<220> FEATURE:
<223> OTHER INFORMATION: synthetic PCR amplification F-primer for
      C21orf4 hypothetical protein combined bisulfite
      restriction analysis (COBRA) region C

<400> SEQUENCE: 81
tttaggttgg agtgtagtgg tataattttg tat                                        33

<210> SEQ ID NO 82
<211> LENGTH: 36
<212> TYPE: DNA
<213> ORGANISM: Artificial Sequence
<220> FEATURE:
<223> OTHER INFORMATION: synthetic PCR amplification R-primer for
      C21orf4 hypothetical protein combined bisulfite
      restriction analysis (COBRA) region C

<400> SEQUENCE: 82
cctttcttaa aactttacac acaactttac tttaaa                                     36

<210> SEQ ID NO 83
<211> LENGTH: 32
<212> TYPE: DNA
<213> ORGANISM: Artificial Sequence
<220> FEATURE:
<223> OTHER INFORMATION: synthetic PCR amplification F-primer for
      ubiquitin-conjugating enzyme E2G2, ubiquitin-protein ligase G2,
      ubiquitin carrier protein G2 (UBE2G2), ubiquitin conjugating
      enzyme 7 (UBC7) combined bisulfite restriction analysis (COBRA)
      region A

<400> SEQUENCE: 83
ggaaatgtyg tttgttaata gatttgttgt tt                                         32

<210> SEQ ID NO 84
<211> LENGTH: 42
<212> TYPE: DNA
<213> ORGANISM: Artificial Sequence
<220> FEATURE:
<223> OTHER INFORMATION: synthetic PCR amplification R-primer for
      ubiquitin-conjugating enzyme E2G2, ubiquitin-protein ligase G2,
``` ubiquitin carrier protein G2 (UBE2G2), ubiquitin conjugating
enzyme 7 (UBC7) combined bisulfite restriction analysis (COBRA)
region A

<400> SEQUENCE: 84
ctcttaccta tcaattatat tttttaactt tttattataa aa                                42

<210> SEQ ID NO 85
<211> LENGTH: 22
<212> TYPE: DNA
<213> ORGANISM: Artificial Sequence
<220> FEATURE:
<223> OTHER INFORMATION: synthetic PCR amplification F-primer for
      ubiquitin-conjugating enzyme E2G2, ubiquitin-protein ligase G2,
      ubiquitin carrier protein G2 (UBE2G2), ubiquitin conjugating
      enzyme 7 (UBC7) combined bisulfite restriction analysis (COBRA)
      region B

<400> SEQUENCE: 85
agaggtggtg gttggatgga tt                                                      22

<210> SEQ ID NO 86
<211> LENGTH: 28
<212> TYPE: DNA
<213> ORGANISM: Artificial Sequence
<220> FEATURE:
<223> OTHER INFORMATION: synthetic PCR amplification R-primer for
      ubiquitin-conjugating enzyme E2G2, ubiquitin-protein ligase G2,
      ubiquitin carrier protein G2 (UBE2G2), ubiquitin conjugating
      enzyme 7 (UBC7) combined bisulfite restriction analysis (COBRA)
      region B

<400> SEQUENCE: 86
ccacctatcc tttacactat acccaaaa                                                28

<210> SEQ ID NO 87
<211> LENGTH: 37
<212> TYPE: DNA
<213> ORGANISM: Artificial Sequence
<220> FEATURE:
<223> OTHER INFORMATION: synthetic PCR amplification F-primer for PR
      domain containing 15 (PRDM15, PFM15), zinc finger protein
      298 (ZNF298), C21orf83 combined bisulfite
      restriction analysis (COBRA) region A

<400> SEQUENCE: 87
gtattataat ttttgattta gtttttatgt tagggtt                                      37

<210> SEQ ID NO 88
<211> LENGTH: 29
<212> TYPE: DNA
<213> ORGANISM: Artificial Sequence
<220> FEATURE:
<223> OTHER INFORMATION: synthetic PCR amplification R-primer for PR
      domain containing 15 (PRDM15, PFM15), zinc finger protein
      298 (ZNF298), C21orf83 combined bisulfite
      restriction analysis (COBRA) region A

<400> SEQUENCE: 88
caaatacact cactcctacc aaaacctaa                                               29

<210> SEQ ID NO 89
<211> LENGTH: 30
<212> TYPE: DNA
<213> ORGANISM: Artificial Sequence
<220> FEATURE:
<223> OTHER INFORMATION: synthetic PCR amplification F-primer for PR
      domain containing 15 (PRDM15, PFM15), zinc finger protein
      298 (ZNF298), C21orf83 combined bisulfite
      restriction analysis (COBRA) region B

<400> SEQUENCE: 89
attygttgtg tttttgaagg tatgaagatt                                    30

<210> SEQ ID NO 90
<211> LENGTH: 25
<212> TYPE: DNA
<213> ORGANISM: Artificial Sequence
<220> FEATURE:
<223> OTHER INFORMATION: synthetic PCR amplification R-primer for PR
      domain containing 15 (PRDM15, PFM15), zinc finger protein
      298 (ZNF298), C21orf83 combined bisulfite
      restriction analysis (COBRA) region B

<400> SEQUENCE: 90
acccacctaa cttccctaca caata                                        25

<210> SEQ ID NO 91
<211> LENGTH: 25
<212> TYPE: DNA
<213> ORGANISM: Artificial Sequence
<220> FEATURE:
<223> OTHER INFORMATION: synthetic PCR amplification F-primer for PR
      domain containing 15 (PRDM15, PFM15), zinc finger protein
      298 (ZNF298), C21orf83 combined bisulfite
      restriction analysis (COBRA) region C

<400> SEQUENCE: 91
gtttagggta gtgttggggt tgttt                                        25

<210> SEQ ID NO 92
<211> LENGTH: 33
<212> TYPE: DNA
<213> ORGANISM: Artificial Sequence
<220> FEATURE:
<223> OTHER INFORMATION: synthetic PCR amplification R-primer for PR
      domain containing 15 (PRDM15, PFM15), zinc finger protein
      298 (ZNF298), C21orf83 combined bisulfite
      restriction analysis (COBRA) region C

<400> SEQUENCE: 92
cttcaaccac ataaaatcca catatacact ata                               33

<210> SEQ ID NO 93
<211> LENGTH: 40
<212> TYPE: DNA
<213> ORGANISM: Artificial Sequence
<220> FEATURE:
<223> OTHER INFORMATION: synthetic PCR amplification F-primer for PR
      domain containing 15 (PRDM15, PFM15), zinc finger protein
      298 (ZNF298), C21orf83 combined bisulfite
      restriction analysis (COBRA) region D

<400> SEQUENCE: 93
aagtagagag gttagtttat taatagaagt attaattgtt                        40

<210> SEQ ID NO 94
<211> LENGTH: 25
<212> TYPE: DNA
<213> ORGANISM: Artificial Sequence
<220> FEATURE:
<223> OTHER INFORMATION: synthetic PCR amplification R-primer for PR
      domain containing 15 (PRDM15, PFM15), zinc finger protein
      298 (ZNF298), C21orf83 combined bisulfite
      restriction analysis (COBRA) region D

<400> SEQUENCE: 94
aaacttctcc ccacacctct caata                                        25

<210> SEQ ID NO 95
<211> LENGTH: 30
<212> TYPE: DNA
<213> ORGANISM: Artificial Sequence
<220> FEATURE:
<223> OTHER INFORMATION: synthetic PCR amplification F-primer for v-ets
      erythroblastosis virus E26 oncogene homolog 2
      (ETS2, ETS2IT1, C-ets-2)

<400> SEQUENCE: 95
gtagttatgt ggattttggg tagattgttt                                    30

<210> SEQ ID NO 96
<211> LENGTH: 29
<212> TYPE: DNA
<213> ORGANISM: Artificial Sequence
<220> FEATURE:
<223> OTHER INFORMATION: synthetic PCR amplification R-primer for v-ets
      erythroblastosis virus E26 oncogene homolog 2
      (ETS2, ETS2IT1, C-ets-2)

<400> SEQUENCE: 96
cacattcact caaaatctcc acttaataa                                     29

<210> SEQ ID NO 97
<211> LENGTH: 23
<212> TYPE: DNA
<213> ORGANISM: Artificial Sequence
<220> FEATURE:
<223> OTHER INFORMATION: synthetic PCR amplification F-primer for
      GDP-fucose protein-O-fucosyltransferase 2,
      protein-O-fucosyltransferase 2 (POFUT2, O-FucT-2,
      FUT13), C21orf80

<400> SEQUENCE: 97
ttyggggaat agygggagtt gtt                                           23

<210> SEQ ID NO 98
<211> LENGTH: 27
<212> TYPE: DNA
<213> ORGANISM: Artificial Sequence
<220> FEATURE:
<223> OTHER INFORMATION: synthetic PCR amplification R-primer for
      GDP-fucose protein-O-fucosyltransferase 2,
      protein-O-fucosyltransferase 2 (POFUT2, O-FucT-2,
      FUT13), C21orf80

<400> SEQUENCE: 98
aatactctcr ccccctctaaa actaaaa                                      27

<210> SEQ ID NO 99
<211> LENGTH: 31
<212> TYPE: DNA
<213> ORGANISM: Artificial Sequence
<220> FEATURE:
<223> OTHER INFORMATION: synthetic PCR amplification F-primer for BTB
      and CNC homology 1, basic region leucine zipper
      transcriptional regulator 1 (BACH1), transcription
      factor BACH1t

<400> SEQUENCE: 99
gaagaatggt tatgtagggt agaggataat t                                  31

<210> SEQ ID NO 100
<211> LENGTH: 37
<212> TYPE: DNA
<213> ORGANISM: Artificial Sequence
<220> FEATURE:
<223> OTHER INFORMATION: synthetic PCR amplification R-primer for BTB -continued and CNC homology 1, basic region leucine zipper
transcriptional regulator 1 (BACH1), transcription
factor BACH1t

<400> SEQUENCE: 100
aattcrtaac tttcataaaa atctactcct cttctaa                              37

<210> SEQ ID NO 101
<211> LENGTH: 32
<212> TYPE: DNA
<213> ORGANISM: Artificial Sequence
<220> FEATURE:
<223> OTHER INFORMATION: synthetic PCR amplification F-primer for
      C21orf84

<400> SEQUENCE: 101
gttaggttag atatgttggg tagttagggt tt                                   32

<210> SEQ ID NO 102
<211> LENGTH: 24
<212> TYPE: DNA
<213> ORGANISM: Artificial Sequence
<220> FEATURE:
<223> OTHER INFORMATION: synthetic PCR amplification R-primer for
      C21orf84

<400> SEQUENCE: 102
catataaccc ctaaccaccc caaa                                            24

<210> SEQ ID NO 103
<211> LENGTH: 29
<212> TYPE: DNA
<213> ORGANISM: Artificial Sequence
<220> FEATURE:
<223> OTHER INFORMATION: synthetic PCR amplification F-primer for solute
      carrier family 19 (folate transporter), member 1 (SLC19A1),
      intestinal folate carrier 1 (IFC1), reduced folate carrier (REFC)
      combined bisulfite restriction analysis (COBRA) region A

<400> SEQUENCE: 103
ttttagtttt tttggttgta ggagaggtt                                       29

<210> SEQ ID NO 104
<211> LENGTH: 30
<212> TYPE: DNA
<213> ORGANISM: Artificial Sequence
<220> FEATURE:
<223> OTHER INFORMATION: synthetic PCR amplification R-primer for solute
      carrier family 19 (folate transporter), member 1 (SLC19A1),
      intestinal folate carrier 1 (IFC1), reduced folate carrier (REFC)
      combined bisulfite restriction analysis (COBRA) region A

<400> SEQUENCE: 104
aataaacacc ttataattca acccaaaaaa                                      30

<210> SEQ ID NO 105
<211> LENGTH: 26
<212> TYPE: DNA
<213> ORGANISM: Artificial Sequence
<220> FEATURE:
<223> OTHER INFORMATION: synthetic PCR amplification F-primer for solute
      carrier family 19 (folate transporter), member 1 (SLC19A1),
      intestinal folate carrier 1 (IFC1), reduced folate carrier (REFC)
      combined bisulfite restriction analysis (COBRA) region B

<400> SEQUENCE: 105
gttattggga tagtggaggt gttgtt                                          26

<210> SEQ ID NO 106
<211> LENGTH: 33
<212> TYPE: DNA
<213> ORGANISM: Artificial Sequence
<220> FEATURE:
<223> OTHER INFORMATION: synthetic PCR amplification R-primer for solute
      carrier family 19 (folate transporter), member 1 (SLC19A1),
      intestinal folate carrier 1 (IFC1), reduced folate carrier (REFC)
      combined bisulfite restriction analysis (COBRA) region B

<400> SEQUENCE: 106
acacataata ctcaccccta taaataacct taa                                    33

<210> SEQ ID NO 107
<211> LENGTH: 20
<212> TYPE: DNA
<213> ORGANISM: Artificial Sequence
<220> FEATURE:
<223> OTHER INFORMATION: synthetic PCR amplification F-primer for solute
      carrier family 19 (folate transporter), member 1 (SLC19A1),
      intestinal folate carrier 1 (IFC1), reduced folate carrier (REFC)
      combined bisulfite restriction analysis (COBRA) region C

<400> SEQUENCE: 107
tygtgggtgg gagggtgttt                                                   20

<210> SEQ ID NO 108
<211> LENGTH: 21
<212> TYPE: DNA
<213> ORGANISM: Artificial Sequence
<220> FEATURE:
<223> OTHER INFORMATION: synthetic PCR amplification R-primer for solute
      carrier family 19 (folate transporter), member 1 (SLC19A1),
      intestinal folate carrier 1 (IFC1), reduced folate carrier (REFC)
      combined bisulfite restriction analysis (COBRA) region C

<400> SEQUENCE: 108
cccccacact cacctcacaa a                                                 21

<210> SEQ ID NO 109
<211> LENGTH: 30
<212> TYPE: DNA
<213> ORGANISM: Artificial Sequence
<220> FEATURE:
<223> OTHER INFORMATION: synthetic PCR amplification F-primer for beta 2
      integrin (complement component 3 receptor 3 and 4 subunit)
      (ITGB2), leukocyte-associated antigen CD18/11A,11B,11C, cell
      surface adhesion protein LFA-1/p150,95 subunit beta, combined
      bisulfite restriction analysis (COBRA) region A

<400> SEQUENCE: 109
gtgtgtattt ggaaataaaa gggtaggatt                                        30

<210> SEQ ID NO 110
<211> LENGTH: 26
<212> TYPE: DNA
<213> ORGANISM: Artificial Sequence
<220> FEATURE:
<223> OTHER INFORMATION: synthetic PCR amplification R-primer for beta 2
      integrin (complement component 3 receptor 3 and 4 subunit)
      (ITGB2), leukocyte-associated antigen CD18/11A,11B,11C, cell
      surface adhesion protein LFA-1/p150,95 subunit beta, combined
      bisulfite restriction analysis (COBRA) region A

<400> SEQUENCE: 110
tacactctac cccaatatac cccaaa                                            26

<210> SEQ ID NO 111
<211> LENGTH: 25
<212> TYPE: DNA

<213> ORGANISM: Artificial Sequence
<220> FEATURE:
<223> OTHER INFORMATION: synthetic PCR amplification F-primer for beta 2
      integrin (complement component 3 receptor 3 and 4 subunit)
      (ITGB2), leukocyte-associated antigen CD18/11A,11B,11C, cell
      surface adhesion protein LFA-1/p150,95 subunit beta, combined
      bisulfite restriction analysis (COBRA) region B

<400> SEQUENCE: 111 agggagttt tatgggtggt tagtt                                           25

<210> SEQ ID NO 112
<211> LENGTH: 23
<212> TYPE: DNA
<213> ORGANISM: Artificial Sequence
<220> FEATURE:
<223> OTHER INFORMATION: synthetic PCR amplification R-primer for beta 2
      integrin (complement component 3 receptor 3 and 4 subunit)
      (ITGB2), leukocyte-associated antigen CD18/11A,11B,11C, cell
      surface adhesion protein LFA-1/p150,95 subunit beta, combined
      bisulfite restriction analysis (COBRA) region B

<400> SEQUENCE: 112
caccaccccc aaatacaaaa aaa                                            23

<210> SEQ ID NO 113
<211> LENGTH: 21
<212> TYPE: DNA
<213> ORGANISM: Artificial Sequence
<220> FEATURE:
<223> OTHER INFORMATION: synthetic PCR amplification F-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region A

<400> SEQUENCE: 113
tggggtggtg gtggtttagt t                                              21

<210> SEQ ID NO 114
<211> LENGTH: 21
<212> TYPE: DNA
<213> ORGANISM: Artificial Sequence
<220> FEATURE:
<223> OTHER INFORMATION: synthetic PCR amplification R-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region A

<400> SEQUENCE: 114
ctcccaacrc aaaaaaccaa a                                              21

<210> SEQ ID NO 115
<211> LENGTH: 36
<212> TYPE: DNA
<213> ORGANISM: Artificial Sequence
<220> FEATURE:
<223> OTHER INFORMATION: synthetic PCR amplification F-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region B

<400> SEQUENCE: 115
aagtgaggat attataaagg attttaaaga attttt                              36

<210> SEQ ID NO 116
<211> LENGTH: 39
<212> TYPE: DNA

<213> ORGANISM: Artificial Sequence
<220> FEATURE:
<223> OTHER INFORMATION: synthetic PCR amplification R-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region B

<400> SEQUENCE: 116
taataaataa tcatatacct tatcataatc ctcaatata                        39

<210> SEQ ID NO 117
<211> LENGTH: 39
<212> TYPE: DNA
<213> ORGANISM: Artificial Sequence
<220> FEATURE:
<223> OTHER INFORMATION: synthetic PCR amplification F-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region C

<400> SEQUENCE: 117
gtttagattg tatatgggaa ttatattatg ttagttttt                        39

<210> SEQ ID NO 118
<211> LENGTH: 25
<212> TYPE: DNA
<213> ORGANISM: Artificial Sequence
<220> FEATURE:
<223> OTHER INFORMATION: synthetic PCR amplification R-primer for
      ubiquitin specific protease 16 (USP16), ubiquitin carboxyl-
      terminal hydrolase 16, ubiquitin-processing protease UBP-M,
      deubiquitinating enzyme 16 combined bisulfite restriction analysis
      (COBRA) region C

<400> SEQUENCE: 118
ctcccacaat tcccacatat cataa                                       25

<210> SEQ ID NO 119
<211> LENGTH: 34
<212> TYPE: DNA
<213> ORGANISM: Artificial Sequence
<220> FEATURE:
<223> OTHER INFORMATION: synthetic PCR amplification F-primer for
      C21orf121, PRED87 combined bisulfite restriction
      analysis (COBRA) region A

<400> SEQUENCE: 119
ggggttattt atttggtgat agtggtatat attt                             34

<210> SEQ ID NO 120
<211> LENGTH: 30
<212> TYPE: DNA
<213> ORGANISM: Artificial Sequence
<220> FEATURE:
<223> OTHER INFORMATION: synthetic PCR amplification R-primer for
      C21orf121, PRED87 combined bisulfite restriction
      analysis (COBRA) region A

<400> SEQUENCE: 120
atccctaccc tattattcct cttttacaaa                                  30

<210> SEQ ID NO 121
<211> LENGTH: 34
<212> TYPE: DNA
<213> ORGANISM: Artificial Sequence
<220> FEATURE:
<223> OTHER INFORMATION: synthetic PCR amplification F-primer for
      C21orf121, PRED87 combined bisulfite restriction analysis (COBRA) region B

<400> SEQUENCE: 121 tttatgaga aatttttta aaatggatta attt                                    34

<210> SEQ ID NO 122
<211> LENGTH: 21
<212> TYPE: DNA
<213> ORGANISM: Artificial Sequence
<220> FEATURE:
<223> OTHER INFORMATION: synthetic PCR amplification R-primer for
      C21orf121, PRED87 combined bisulfite restriction
      analysis (COBRA) region B

<400> SEQUENCE: 122
catcccaaca caccrctaaa a                                                21

<210> SEQ ID NO 123
<211> LENGTH: 17
<212> TYPE: DNA
<213> ORGANISM: Artificial Sequence
<220> FEATURE:
<223> OTHER INFORMATION: synthetic PCR amplification forward primer for
      holocarboxylase synthetase
      (biotin-(proprionyl-CoA-carboxylase
      (ATP-hydrolyzing)) ligase) (HLCS)

<400> SEQUENCE: 123
ccgtgtggcc agaggtg                                                     17

<210> SEQ ID NO 124
<211> LENGTH: 17
<212> TYPE: DNA
<213> ORGANISM: Artificial Sequence
<220> FEATURE:
<223> OTHER INFORMATION: synthetic PCR amplification reverse primer for
      holocarboxylase synthetase
      (biotin-(proprionyl-CoA-carboxylase
      (ATP-hydrolyzing)) ligase) (HLCS)

<400> SEQUENCE: 124
aaagggccag gtcggga                                                     17

<210> SEQ ID NO 125
<211> LENGTH: 17
<212> TYPE: DNA
<213> ORGANISM: Artificial Sequence
<220> FEATURE:
<223> OTHER INFORMATION: synthetic PCR amplification TaqMan probe (FAM)
      for holocarboxylase synthetase
      (biotin-(proprionyl-CoA-carboxylase
      (ATP-hydrolyzing)) ligase) (HLCS)
<220> FEATURE:
<221> NAME/KEY: modified_base
<222> LOCATION: (1)...(1)
<223> OTHER INFORMATION: a modified by 6-carboxylfluorescein (FAM)
<220> FEATURE:
<221> NAME/KEY: modified_base
<222> LOCATION: (17)...(17)
<223> OTHER INFORMATION: c modified by minor-groove binder (MGB)

<400> SEQUENCE: 125
aggatttggg gctgcgc                                                     17

<210> SEQ ID NO 126
<211> LENGTH: 17
<212> TYPE: DNA
<213> ORGANISM: Artificial Sequence
<220> FEATURE:
<223> OTHER INFORMATION: synthetic PCR amplification TaqMan probe (VIC)

```
             for holocarboxylase synthetase
             (biotin-(proprionyl-CoA-carboxylase
             (ATP-hydrolyzing)) ligase) (HLCS)
<220> FEATURE:
<221> NAME/KEY: modified_base
<222> LOCATION: (1)...(1)
<223> OTHER INFORMATION: a modified by Applied Biosystems proprietary
      dye VIC
<220> FEATURE:
<221> NAME/KEY: modified_base
<222> LOCATION: (17)...(17)
<223> OTHER INFORMATION: c modified by minor-groove binder (MGB)

<400> SEQUENCE: 126
aggatttggg gctgcgc                                                    17

<210> SEQ ID NO 127
<211> LENGTH: 29
<212> TYPE: DNA
<213> ORGANISM: Artificial Sequence
<220> FEATURE:
<223> OTHER INFORMATION: synthetic PCR amplification forward primer for
      transmembrane emp24 protein transport domain
      containing 8 (TMED8)

<400> SEQUENCE: 127
tggtaagact cttagaaatc acagatgtt                                       29

<210> SEQ ID NO 128
<211> LENGTH: 29
<212> TYPE: DNA
<213> ORGANISM: Artificial Sequence
<220> FEATURE:
<223> OTHER INFORMATION: synthetic PCR amplification reverse primer for
      transmembrane emp24 protein transport domain
      containing 8 (TMED8)

<400> SEQUENCE: 128
gtatcccaac taatcattta ttatggtca                                       29

<210> SEQ ID NO 129
<211> LENGTH: 17
<212> TYPE: DNA
<213> ORGANISM: Artificial Sequence
<220> FEATURE:
<223> OTHER INFORMATION: synthetic PCR amplification TaqMan
      probe_TMED8-C for transmembrane emp24 protein transport domain
      containing 8 (TMED8)
<220> FEATURE:
<221> NAME/KEY: modified_base
<222> LOCATION: (1)...(1)
<223> OTHER INFORMATION: c modified by 6-carboxyfluorescein (FAM)
<220> FEATURE:
<221> NAME/KEY: modified_base
<222> LOCATION: (17)...(17)
<223> OTHER INFORMATION: t modified by minor-groove binder (MGB)

<400> SEQUENCE: 129
cccctatcat gagaaat                                                    17

<210> SEQ ID NO 130
<211> LENGTH: 17
<212> TYPE: DNA
<213> ORGANISM: Artificial Sequence
<220> FEATURE:
<223> OTHER INFORMATION: synthetic PCR amplification TaqMan
      probe_TMED8-G for transmembrane emp24 protein transport domain
      containing 8 (TMED8)
<220> FEATURE:
<221> NAME/KEY: modified_base
<222> LOCATION: (1)...(1)
<223> OTHER INFORMATION: c modified by Applied Biosystems proprietary
```

```
                       dye VIC
<220> FEATURE:
<221> NAME/KEY: modified_base
<222> LOCATION: (17)...(17)
<223> OTHER INFORMATION: t modified by minor-groove binder (MGB)

<400> SEQUENCE: 130
cccctatgat gagaaat                                                        17

<210> SEQ ID NO 131
<211> LENGTH: 16
<212> TYPE: DNA
<213> ORGANISM: Artificial Sequence
<220> FEATURE:
<223> OTHER INFORMATION: synthetic PCR amplification forward primer for
      beta-actin

<400> SEQUENCE: 131
ccaccaccgc cgagac                                                         16

<210> SEQ ID NO 132
<211> LENGTH: 17
<212> TYPE: DNA
<213> ORGANISM: Artificial Sequence
<220> FEATURE:
<223> OTHER INFORMATION: synthetic PCR amplification reverse primer for
      beta-actin

<400> SEQUENCE: 132
tggccgggct tacctgg                                                        17

<210> SEQ ID NO 133
<211> LENGTH: 16
<212> TYPE: DNA
<213> ORGANISM: Artificial Sequence
<220> FEATURE:
<223> OTHER INFORMATION: synthetic PCR amplification TaqMan probe for
      beta-actin
<220> FEATURE:
<221> NAME/KEY: modified_base
<222> LOCATION: (1)...(1)
<223> OTHER INFORMATION: a modified by 6-carboxyfluorescein (FAM)
<220> FEATURE:
<221> NAME/KEY: modified_base
<222> LOCATION: (16)...(16)
<223> OTHER INFORMATION: c modified by minor-groove binder (MGB)

<400> SEQUENCE: 133
agcacagagc ctcgcc                                                         16

<210> SEQ ID NO 134
<211> LENGTH: 30
<212> TYPE: DNA
<213> ORGANISM: Artificial Sequence
<220> FEATURE:
<223> OTHER INFORMATION: synthetic PCR amplification forward primer for
      bisulfite sequencing of fetal trisomy 18 Marker
      18A

<400> SEQUENCE: 134
aggaagagag ggttatttgg gggtagtagg                                          30

<210> SEQ ID NO 135
<211> LENGTH: 56
<212> TYPE: DNA
<213> ORGANISM: Artificial Sequence
<220> FEATURE:
<223> OTHER INFORMATION: synthetic PCR amplification reverse primer for
      bisulfite sequencing of fetal trisomy 18 Marker
      18A
```

<400> SEQUENCE: 135
cagtaatacg actcactata gggagaaggc taaactcaaa actaaaacaa acactc         56

<210> SEQ ID NO 136
<211> LENGTH: 30
<212> TYPE: DNA
<213> ORGANISM: Artificial Sequence
<220> FEATURE:
<223> OTHER INFORMATION: synthetic PCR amplification forward primer for
    Epityp[er assay of fetal trisomy 18 Marker 18A

<400> SEQUENCE: 136
aggaagagag ggttatttgg gggtagtagg                                     30

<210> SEQ ID NO 137
<211> LENGTH: 56
<212> TYPE: DNA
<213> ORGANISM: Artificial Sequence
<220> FEATURE:
<223> OTHER INFORMATION: synthetic PCR amplification reverse primer for
    Epityper assay of fetal trisomy 18 Marker 18A

<400> SEQUENCE: 137
cagtaatacg actcactata gggagaaggc taaactcaaa actaaaacaa acactc         56

<210> SEQ ID NO 138
<211> LENGTH: 30
<212> TYPE: DNA
<213> ORGANISM: Artificial Sequence
<220> FEATURE:
<223> OTHER INFORMATION: synthetic PCR amplification forward primer for
    bisulfite sequencing of beta-actin

<400> SEQUENCE: 138
tttattttgy gatttttatt ggtaagagtt                                     30

<210> SEQ ID NO 139
<211> LENGTH: 22
<212> TYPE: DNA
<213> ORGANISM: Artificial Sequence
<220> FEATURE:
<223> OTHER INFORMATION: synthetic PCR amplification reverse primer for
    bisulfite sequencing of beta-actin

<400> SEQUENCE: 139
aacacaaaac ctcrccttta cc                                             22

<210> SEQ ID NO 140
<211> LENGTH: 16
<212> TYPE: DNA
<213> ORGANISM: Artificial Sequence
<220> FEATURE:
<223> OTHER INFORMATION: synthetic quantitative real-time PCR (qPCR)
    amplification forward primer for fetal trisomy 18
    Marker 18A

<400> SEQUENCE: 140
aggcctgcgc aggtgg                                                    16

<210> SEQ ID NO 141
<211> LENGTH: 18
<212> TYPE: DNA
<213> ORGANISM: Artificial Sequence
<220> FEATURE:
<223> OTHER INFORMATION: synthetic quantitative real-time PCR (qPCR)
    amplification reverse primer for fetal trisomy 18
    Marker 18A

```
<400> SEQUENCE: 141
cactcgctga gcgtcccc                                                    18

<210> SEQ ID NO 142
<211> LENGTH: 18
<212> TYPE: DNA
<213> ORGANISM: Artificial Sequence
<220> FEATURE:
<223> OTHER INFORMATION: synthetic quantitative real-time PCR (qPCR)
      amplification TaqMan probe (FAM) for fetal trisomy
      18 Marker 18A
<220> FEATURE:
<221> NAME/KEY: modified_base
<222> LOCATION: (1)...(1)
<223> OTHER INFORMATION: c modified by 6-carboxyfluorescein (FAM)
<220> FEATURE:
<221> NAME/KEY: modified_base
<222> LOCATION: (18)...(18)
<223> OTHER INFORMATION: g modified by Black-hole quencher 1 (BHQ1)

<400> SEQUENCE: 142
cgccccgcac agcgctcg                                                    18

<210> SEQ ID NO 143
<211> LENGTH: 25
<212> TYPE: DNA
<213> ORGANISM: Artificial Sequence
<220> FEATURE:
<223> OTHER INFORMATION: synthetic quantitative real-time PCR (qPCR) and
      digital PCR amplification forward primer for zinc
      finger protein, Y-linked (ZFY)

<400> SEQUENCE: 143
caagtgctgg actcagatgt aactg                                            25

<210> SEQ ID NO 144
<211> LENGTH: 28
<212> TYPE: DNA
<213> ORGANISM: Artificial Sequence
<220> FEATURE:
<223> OTHER INFORMATION: synthetic quantitative real-time PCR (qPCR) and
      digital PCR amplification reverse primer for zinc
      finger protein, Y-linked (ZFY)

<400> SEQUENCE: 144
tgaagtaatg tcagaagcta aaacatca                                         28

<210> SEQ ID NO 145
<211> LENGTH: 17
<212> TYPE: DNA
<213> ORGANISM: Artificial Sequence
<220> FEATURE:
<223> OTHER INFORMATION: synthetic quantitative real-time PCR (qPCR) and
      digital PCR amplification TaqMan probe (VIC) for
      zinc finger protein, Y-linked (ZFY)
<220> FEATURE:
<221> NAME/KEY: modified_base
<222> LOCATION: (1)...(1)
<223> OTHER INFORMATION: t modified by Applied Biosystems proprietary
      dye VIC
<220> FEATURE:
<221> NAME/KEY: modified_base
<222> LOCATION: (17)...(17)
<223> OTHER INFORMATION: c modified by minor-groove binder (MGB)

<400> SEQUENCE: 145
tctttaccac actgcac                                                     17

<210> SEQ ID NO 146
```

```
<211> LENGTH: 17
<212> TYPE: DNA
<213> ORGANISM: Artificial Sequence
<220> FEATURE:
<223> OTHER INFORMATION: synthetic quantitative real-time PCR (qPCR)
      amplification forward primer for beta-actin

<400> SEQUENCE: 146
cccccatctc cggaggc                                                  17

<210> SEQ ID NO 147
<211> LENGTH: 16
<212> TYPE: DNA
<213> ORGANISM: Artificial Sequence
<220> FEATURE:
<223> OTHER INFORMATION: synthetic quantitative real-time PCR (qPCR)
      amplification reverse primer for beta-actin

<400> SEQUENCE: 147
gtctgggccg cagcgg                                                   16

<210> SEQ ID NO 148
<211> LENGTH: 17
<212> TYPE: DNA
<213> ORGANISM: Artificial Sequence
<220> FEATURE:
<223> OTHER INFORMATION: synthetic quantitative real-time PCR (qPCR)
      amplification TaqMan probe (VIC) for beta-actin
<220> FEATURE:
<221> NAME/KEY: modified_base
<222> LOCATION: (1)...(1)
<223> OTHER INFORMATION: a modified by Applied Biosystems proprietary
      dye VIC
<220> FEATURE:
<221> NAME/KEY: modified_base
<222> LOCATION: (17)...(17)
<223> OTHER INFORMATION: c modified by minor-groove binder (MGB)

<400> SEQUENCE: 148
aggggcttct cccgcgc                                                  17

<210> SEQ ID NO 149
<211> LENGTH: 23
<212> TYPE: DNA
<213> ORGANISM: Artificial Sequence
<220> FEATURE:
<223> OTHER INFORMATION: synthetic digital PCR amplification forward
      primer for fetal trisomy 13 Marker 13A

<400> SEQUENCE: 149
gaaataaacg ccggaacatc ttg                                           23

<210> SEQ ID NO 150
<211> LENGTH: 24
<212> TYPE: DNA
<213> ORGANISM: Artificial Sequence
<220> FEATURE:
<223> OTHER INFORMATION: synthetic digital PCR amplification reverse
      primer for fetal trisomy 13 Marker 13A

<400> SEQUENCE: 150
tctcacggaa ccgtagacta ggaa                                          24

<210> SEQ ID NO 151
<211> LENGTH: 26
<212> TYPE: DNA
<213> ORGANISM: Artificial Sequence
<220> FEATURE:
<223> OTHER INFORMATION: synthetic digital PCR amplification TaqMan
      probe (FAM) for fetal trisomy 13 Marker 13A
```

```
<220> FEATURE:
<221> NAME/KEY: misc_feature
<222> LOCATION: (1)...(1)
<223> OTHER INFORMATION: a modified by 6-carboxyfluorescein (FAM)
<220> FEATURE:
<221> NAME/KEY: modified_base
<222> LOCATION: (26)...(26)
<223> OTHER INFORMATION: c modified by Black-hole quencher 1 (BHQ1)

<400> SEQUENCE: 151
acagagcagg aagccgatgt gactgc                                           26
```

METHOD FOR DETECTING CHROMOSOMAL ANEUPLOIDY

RELATED APPLICATIONS

This application claims priority to U.S. Provisional Patent Application No. 61/233,042, filed Aug. 11, 2009, and U.S. Provisional Patent Application No. 61/308,578, filed Feb. 26, 2010, the contents of each are hereby incorporated by reference in the entirety for all purposes.

BACKGROUND OF THE INVENTION

Various genetic disorders, such as chromosomal aneuploidies, are detectable during pregnancy according to a variety of methods currently in use by hospitals and medical professionals. Most of these methods, however, are invasive and carry a risk of unintended loss of fetus or miscarriage. Noninvasive prenatal diagnosis of chromosomal aneuploidies using fetal DNA in maternal plasma is an actively researched area, and there exists a clear need for new and more reliable methods for early detection. This invention provides a novel method for detecting chromosomal aneuploidies such as trisomy 21 by the combination of fetal-specific epigenetic and genetic markers.

In particular, the present inventors searched for fetal DNA markers on chromosomes 21, 18, and 13 that were differentially methylated in the placenta and maternal blood cells using methods including combined bisulfite restriction analysis and immunoprecipitation of methylated DNA followed by tiling array hybridization (MeDIP-chip), with confirmation of any target locus with bisulfite sequencing. The resultant markers were analyzed using methylation-sensitive restriction endonuclease digestion followed by real-time polymerase chain reaction (PCR) or microfluidics digital PCR analysis. Chromosome dosage analysis was performed by comparing the dosage of these epigenetic markers to a genetic marker, a DNA sequence that is derived from a fetus and can be distinguished from a maternal DNA sequence by virtue of its distinct polynucleotide sequence. One example of such genetic marker is the zinc finger protein, Y-linked (ZFY) gene present on chromosome Y.

For example, it was discovered that the putative promoter of the *holocarboxylase synthetase* (HLCS) gene was hypermethylated in the placenta and hypomethylated in maternal blood cells. Chromosome dosage comparison using the hypermethylated HLCS and ZFY loci can distinguish trisomy 21 and euploid placental DNA samples. The inventors showed that the epigenetic-genetic chromosome dosage approach is a new method for the noninvasive prenatal detection of chromosomal aneuploidies such as trisomy 21 (T21), trisomy 18 (T18), or trisomy 13 (T13). This approach provides a generally usable technique for noninvasive prenatal diagnosis, utilizing epigenetic markers on any chromosome involved in a chromosomal aneuploidy.

BRIEF SUMMARY OF THE INVENTION

This invention provides a method for detecting a chromosomal aneuploidy in a fetus carried by a pregnant woman. The method comprises the steps of: (a) determining in a biological sample taken from the pregnant woman the amount of a methylation marker of fetal origin, wherein the methylation marker is located on a chromosome relevant to the chromosomal aneuploidy or within a section of a chromosome relevant to the chromosomal aneuploidy, and wherein the methylation marker of fetal origin is distinguished from its counterpart of maternal origin due to differential DNA methylation; (b) determining the amount of a genetic marker of fetal origin in the sample, wherein the genetic marker is located on a reference chromosome, and wherein the genetic marker of fetal origin is distinguished from its counterpart of maternal origin in the sample due to difference in polynucleotide sequence, or the genetic marker does not exist in the maternal genome; (c) determining the ratio of the amounts from (a) and (b); and (d) comparing the ratio with a standard control, wherein the ratio higher or lower than the standard control indicates the presence of the chromosomal aneuploidy in the fetus. Typically, the standard control value approximates the expected gene or chromosome dosage or ratio in the human genome, although slight variations may exist depending on the specific methodology used in the detection method. For example, there are two copies of chromosome 21 and one copy of chromosome Y in a euploid male genome. Hence, the ratio of dosage between an epigenetic marker on chromosome 21 to a genetic marker on chromosome Y would be approximately 2.

In some cases, the methylation marker of fetal origin is from the placenta. In other cases, the counterpart of maternal origin is from the pregnant woman's blood cells. The methylation marker of fetal origin may be more methylated than its counterpart of maternal origin, or it may be less methylated than its counterpart of maternal origin.

In some cases, the sample is maternal whole blood, serum, plasma, urine, amniotic fluid, genital tract lavage fluid, placental-tissue sample, chorionic villus sample, or a sample containing fetal cells isolated from maternal blood. In other cases, the sample is any sample that contains fetal nucleic acids.

In some cases, the methylation marker is part of, or in proximity to, the *Holocarboxylase Synthetase* (HLCS) gene. For example, several regions of the HLCS gene (including the putative promoter region) as shown in Table 2 may be used as methylation markers. Other methylation markers include Marker 18A and Marker 13A. Additional methylation markers are defined as follows: a region of about 15 to 450 nucleotides and comprises one cytosine, the region being (1) a genomic locus selected from the group consisting of MAT.18.0094, MAT.13.0023, MAT.13.0020, MAT.13.0038, MAT.18.0071, MAT.18.0097, MAT.21.0178, and TAS.21.1175; or (2) no more than 10 kb upstream and/or downstream from the locus. Some particular markers on chromosome 21 are defined as follows: a region of about 15 to 450 nucleotides on chromosome 21 and comprises one cytosine, the region being (1) a genomic locus selected from the group consisting of CGI137, phosphodiesterase 9A (PDE9A), *Homo sapiens* protein phosphatase 1, regulatory (inhibitory) subunit 2 pseudogene 2 (PPP1R2P2), and Similarity to Fem1A (*Caenorhabditis elegans*), or (2) no more than 10 kb upstream and/or downstream from the locus. These methylation markers are intended for use in accordance with the detection method of this invention in combination with any one or more of the genetic markers described herein.

In some cases, step (a) comprises treating the sample with a reagent that differentially modifies methylated and unmethylated DNA. Such reagent may comprise bisulfite or a protein or chemical that binds to DNA based on methylation status; or the reagent may comprise an enzyme that either preferentially cleaves methylated DNA or preferentially cleaves unmethylated DNA.

In some cases, the genetic marker does not exist in the maternal genome. In other cases, the genetic marker is located on the Y chromosome. Frequently, the genetic marker of fetal origin is distinguished from the genetic marker of maternal origin based on genetic polymorphism, which includes a single nucleotide polymorphism (SNP), simple tandem repeat polymorphism, and insertion-deletion polymorphism. In one example, the genetic marker is the Zinc-Finger protein, Y-linked (ZFY) gene. In another example, the genetic marker is a genomic sequence comprising SNP rs6636 in TMED8 gene, e.g., SEQ ID NO:1 or SEQ ID NO:2.

In some cases, more than one methylation marker or more than one genetic marker may be used. Frequently, step (a) or step (b) may include the process of amplification of the methylation marker and/or the genetic marker, especially the methylation marker and the genetic marker of the fetal origin. As one example, the amplification is by a polymerase chain reaction (PCR), such as a methylation-specific PCR; or the amplification may be a nucleic acid sequence-specific amplification.

In some cases, step (a) or (b) is performed by molecular counting. In other cases, step (a) or (b) comprises digital polymerase chain reaction, real-time quantitative polymerase chain reaction, array capture, a nucleic acid sequence-based detection, massively parallel genomic sequencing, single molecule sequencing, or multiplexed detection of polynucleotide with color-coded probe pairs. In some other cases, step (a) or (b) comprises mass spectrometry or hybridization to a microarray, fluorescence probe, or molecular beacon.

In some cases, the chromosome relevant to the chromosomal aneuploidy is chromosome 13, 18, 21, or X. For the purpose of data interpretation, in some cases, when the ratio is higher or lower than the standard control by at least 1 standard deviation, it indicates the presence of the chromosomal aneuploidy in the fetus, whereas in other cases, the presence of the chromosomal aneuploidy in the fetus is indicated when the ratio is higher or lower than the standard control by at least 2 or even 3 standard deviations.

Broadly applied, the above described methods can be used in a non-diagnostic context for assessing any potential change in the amount of a particular chromosome of interest in relation to another chromosome, a reference chromosome that is not suspected to have any change in its relative amount.

The present invention can also be embodied in a device or a system comprising one or more such devices, which is capable of carrying out all or some of the method steps described herein. For instance, in some cases, the device or system performs the following steps upon receiving a biological sample taken from the pregnant woman: (a) determining in sample the amount of a fetus derived methylation marker relevant to a chromosomal aneuploidy; (b) determining in the sample the amount of a fetus derived genetic marker on a reference chromosome; (c) determining the ratio of the amounts from (a) and (b); and (d) comparing the ratio with a standard control and providing an output indicating whether the chromosomal aneuploidy is present in the fetus. In other cases, the device or system of the invention performs the task of steps (c) and (d), after steps (a) and (b) have been performed and the amounts from (a) and (b) have been entered into the device. Preferably, the device or system is partially or fully automated.

BRIEF DESCRIPTION OF THE DRAWINGS

FIG. 2. Digital readout of the gene dosage experiment. The HLCS and RASSF1A assays were run as monoplex, while the ZFX/Y assays were run in a duplex fashion. Each chip is divided into 12 panels with each panel being compartmentalized into 765 reaction wells. Reaction wells with the target molecules are shown as red or blue colored dots, while reaction wells with no amplification are shown as grey-colored dots. HLCS, RASSF1A and ZFY are shown in red. ZFX is shown in blue. (A) Illustration of the digital PCR results for enzyme-digested euploid placental DNA samples. Four panels were counted for each sample, hence each chip could accommodate three samples. (B) Illustration of the digital PCR results for an enzyme-digested maternal plasma DNA sample. DNA from the sample was evenly distributed in all 12 panels. It is noted that for maternal plasma analysis, the copy number of ZFY (fetal DNA) was much less than that of ZFX (fetal plus maternal DNA).

FIG. 5. Genomic sequences of the four digital PCR assays (HLCS, RASSF1A, ZFY and ZFX SEQ ID NOS:3-6)). The chromosomal location on the March 2006 human reference sequence (NCBI Build 36.1) of the UCSC Genome Browser is indicated. The underlined nucleotides represent the enzyme recognition sites. The bold nucleotides in capital letters represent the forward and reverse primers. The bold nucleotides in small letters represent the minor groove binding (MGB) probe sequence.

FIG. 10. Chromosome dosage comparison in euploid and trisomy 21 placental tissue DNA samples by determining the ratio of (A) HLCS to TMED8-G with mock digestion, and (B) HLCS to TMED8-G with BstUI digestion. The normal reference range is depicted by dotted lines.

FIG. 13. DNA methylation levels of Marker 18A in euploid (n=6) and TI 8 (n=6) placentas analyzed by the Epityper assay. All T18 and euploid placentas were obtained from the first trimester. The methylation indices (MIs) of the euploid cases were compared with the T18 cases at each CpG unit using Mann Whitney Rank Sum Test.

FIG. 17. DNA methylation levels of a region on the beta-actin gene in 3 pairs of first-trimester euploid placentas and maternal blood cells determined by cloned bisulfite sequencing. For legends of the bisulfite sequencing data, refer to FIG. 12. This region was used for the development of a control assay to check the efficiency of enzyme digestion.

FIG. 19. DNA methylation levels of Marker 13A in euploid (n=5) and T13 (n=5) placentas analyzed by the EPITYPER™ assay. Four of the trisomy 13 (T13) placentas were obtained from the first trimester while one was obtained from the second trimester. All of the euploid placentas were obtained from the first trimester. The MIs of the euploid cases were compared with the T13 cases at each CpG unit using Mann Whitney Rank Sum Test.

DEFINITIONS

Figure 1:
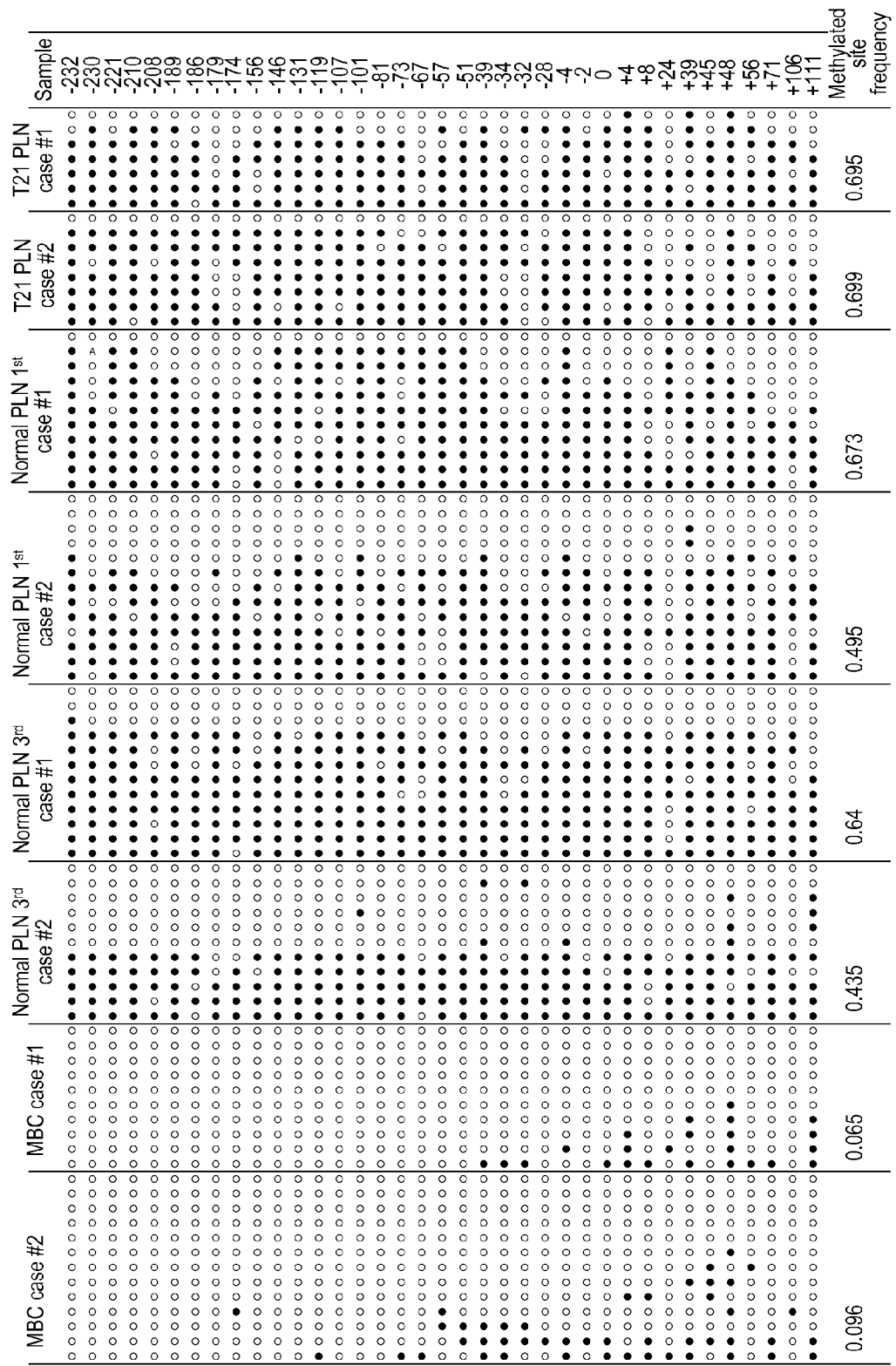
FIG. 1. Cloning and bisulfite sequencing results of HLCS region B2. Individual CpG sites are numbered across the first row, with nucleotide positions defined relative to the transcription start site (position 0). The first CpG site (−232) corresponds to chr21: 37275031 (reverse strand) of the Human March 2006 (hg 18) assembly of the UCSC Genome Browser. Each subsequent row depicts the methylation status across the CpG sites in a single DNA molecule studied by cloning. Filled and unfilled circles represent methylated and unmethylated CpG sites, respectively. Clones from trisomy 21, normal first-trimester and normal third-trimester placental tissue samples are labeled with the prefix "T21 PLN," "Normal PLN 1st," and "Normal PLN 3rd," respectively, while those from maternal blood cells are labeled with the prefix "MBC." Placenta and maternal blood cells from different pregnant individuals are identified by sample numbers following the prefix.

The term "pregnancy-associated disorder," as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. A "pregnancy-associated disorder" is necessarily accompanied by pregnancy and is not merely a condition that is incidentally occurring to a pregnant woman. In other words, the disorder is not one that can occur to a non-pregnant woman. Some examples of a pregnancy-associated disorder include ectopic pregnancy, preeclampsia, preterm labor, and fetal chromosomal abnormalities such as trisomy 13, 18, or 21.

The term "chromosomal aneuploidy," as used herein, encompasses any genetic defect exhibiting an abnormal number of chromosomes, including having more or fewer than normal number of any one chromosome, as well as having an extra portion of any one chromosome in addition to the normal pair, or missing a portion of any one chromosome in the normal pair. In some cases, the abnormality can involve more than one chromosome, or more than one portion of one or more chromosomes. The most common chromosome aneuploidy is trisomy, e.g., trisomy 21, where the genome of an afflicted patient has three rather than the normal two (i.e., a pair) chromosome 21. In rarer cases, the patient may have an extra piece of chromosome 21 (less than full length) in addition to the normal pair. In yet other cases, a portion of chromosome 21 may be translocated to another chromosome, e.g. chromosome 14. In this example, chromosome 21 is referred as the "chromosome relevant to the chromosomal aneuploidy" and a second, irrelevant chromosome, i.e., one that is present in the normal pair in the patient's genome, for example chromosome 1, is a "reference chromosome." There are also cases where the number of a relevant chromosome is less than the normal number of 2. Turner syndrome is one example of a chromosomal aneuploidy where the number of X chromosome in a female subject has been reduced from two to one.

A "genetic marker," as used in the context of comparison with a "methylation marker" to determine their relative amount or concentration, i.e., a ratio, refers to a polynucleotide sequence present in the genomic sequence of a reference chromosome that permits different alleles (e.g., alleles from two different individuals, such as alleles from a fetus v. alleles from the pregnant woman) to be distinguished from each other based on difference in the polynucleotide sequence (e.g., polymorphism), or presence or absence of the sequence at all (e.g., a sequence present on the Y chromosome from a male fetus but not present in the pregnant woman's genome). In this context, a "methylation marker" located on a chromosome relevant to the chromosomal aneuploidy refers to a genomic polynucleotide sequence on a chromosome having an abnormal number; or in the case where there is an extra piece of the chromosome or a portion of the chromosome is missing, the "methylation marker" is located within the piece or portion of the relevant chromosome. Difference in methylation profiles of the methylation marker allows distinction of the corresponding methylation marker from two different individuals, e.g., a fetus and the pregnant woman.

The term "epigenetic state" or "epigenetic status" as used herein refers to any structural feature at the molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins, e.g., histones and the modifications of such proteins, e.g., acetylation, deacetylation, and methylation.

The term "methylation profile" or "methylation status," when used in this application to describe the state of methylation of a genomic sequence, refers to the characteristics of a DNA fragment at a particular genetic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation profile" or "methylation status" may also refer to the relative or absolute concentration of methylated C or unmethylated C at any particular stretch of residues in a biological sample.

The term "single nucleotide polymorphism" or "SNP" as used herein refers to the polynucleotide sequence variation present at a single nucleotide residue among different alleles of the same gene, which may be the same gene located on the two copies of the same chromosome from the same individual (e.g., two alleles from a fetus) or may be the same gene from two different individuals (e.g., fetus and pregnant woman). This variation may occur within the coding region or non-coding region (e.g., the promoter region or its proximity, or the intron) of a gene, or in the intergenic region. Detection of one or more SNP allows differentiation of different alleles of a single gene.

The term "simple tandem repeat polymorphism" as used herein refers to the polynucleotide sequence variation demonstrated in the varying number of tandem repeats of a nucleotide sequence (e.g., a tandem repeat of 1 or more nucleotides) among different alleles of the same gene, which may be the same gene located on two copies of the same chromosome from the same individual (e.g., fetus) or may be the same gene from two different individuals (e.g., fetus and pregnant woman). This variation often occurs within the non-coding region (e.g., the promoter region or its proximity, or intron) of a gene, or in the intergenic region. Detection of difference in tandem repeat numbers allows differentiation of different alleles of a single gene.

The term "insertion-deletion polymorphism" as used herein refers to the polynucleotide sequence variation demonstrated in the presence or absence of a short nucleotide sequence (e.g., 1-3 nucleotides) among different alleles of the same gene, which may be the same gene located on two copies of the same chromosome from the same individual (e.g., fetus) or may be the same gene from two different individuals (e.g., fetus and pregnant woman). This variation can occurs within both the coding region and the non-coding region (e.g., the promoter region or its proximity, or intron) of a gene, or in the intergenic region. Detection of whether a short nucleotide sequence is present allows differentiation of different alleles of a single gene.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibit differential ability in its binding to DNA sequences or precipitation of DNA sequences depending on their methylation status. One class of such reagents consists of methylated DNA binding proteins.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

The term "locus" means the segment of DNA defined by a start nucleotide position to an end nucleotide position on a chromosome (i.e., a genomic location, or a chromosomal location) of a reference genome assembly (e.g., the Human Genome March 2006 assembly (hg18) on the UCSC Genome Browser). A locus may or may not overlap with the genomic location of a gene, a CpG island, or any product of transcription/translation. In this application, a locus usually refers to a continuous segment of DNA identified by experimental data (e.g., a MeDIP-chip dataset) and the subsequent data analysis (e.g., MAT, TAS) to contain different DNA methylation levels. A locus may contain one or more CpG sites. A locus may be sub-divided into shorter segments (e.g., CpG-containing genomic sequences, fragments or regions) that are amenable to analysis (e.g., Epityper assay, bisulfite sequencing, polynucleotide amplification and determination). A locus may be developed into one or more fetal epigenetic markers. In some context of this application, a locus also refers to a continuous segment of DNA identified by certain bioinformatics criteria.

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from an established standard control. An increase is a positive change by at least 10% or 20% or by at least 50%, 80%, or 100% of the standard control value; in some case, an increase can be at least about 1.5-fold, at least about 2-fold, or at least about 3-fold of the control value. Similarly, a decrease is a negative change by at least 1/10, 1/6, 1/5, or by at least 1/3 or even 1/2 of the control value. Other terms indicating quantitative changes or differences from a comparative basis, such as "more," "less," "higher," and "lower," are used in this application in the same fashion as described above.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the HLCS gene in various methylation states. At least one of the PCR primers for amplification of a polynucleotide sequence is sequence-specific for the sequence.

The term "digital polymerase chain reaction" as used herein refers to a refined version of conventional polymerase chain reaction (PCR) methods that can be used to directly quantify and clonally amplify nucleic acids including DNA, cDNA or RNA, such that the amount of target nucleic acid can be directly quantitatively measured. Digital PCR achieves this direct quantitative measurement by capturing or isolating each individual nucleic acid molecule present in a sample within many separate reaction chambers that are able to localize and concentrate the amplification product to detectable levels. After PCR amplification, a count of chambers containing the PCR end-product is a direct measure of the absolute nucleic acid quantity. The capture or isolation of individual nucleic acid molecules, typically by way of dilution, may be effected in capillaries, microemulsions, arrays of miniaturized chambers, or on nucleic acid binding surfaces. The basic methodology of digital PCR is described in, e.g., Sykes et al., *Biotechniques* 13 (3): 444-449, 1992; and Vogelstein and Kinzler, *Proc Natl Acad Sci U S A* 1999; 96:9236-41.

The term "molecular counting" as used herein refers to any method that allows quantitative measurement of the number of a molecule or molecular complex, often the relative number in the context of other co-existing molecules or complexes of distinct characteristics. Various methods of molecular counting are described in, e.g., Leaner et al., *Analytical Chemistry* 69:2115-2121, 1997; Hirano and Fukami, *Nucleic Acids Symposium Series No.* 44:157-158, 2000; Chiu et al., *Trends in Genetics* 25:324-331, 2009; and U.S. Pat. No. 7,537,897.

"Standard control" as used herein refers to a value reflective of the ratio, or the amount or concentration of a fetal genomic sequence located on a chromosome relevant to a particular chromosomal aneuploidy (e.g., trisomy 13, 18, or 21) over the amount or concentration of a fetal genetic marker located on a reference chromosome, as the amounts or concentrations are found in a biological sample (e.g., blood, plasma, or serum) from an average, healthy pregnant woman carrying a chromosomally normal fetus. A "standard control" may be determined differently and represent different value depending on the context in which it is used. For instance, when used in an epigenetic-genetic dosage method where an epigenetic marker is measured against a genetic marker, the "standard control" is a value reflective of the ratio, or the amount or concentration of a fetal genomic sequence located on a chromosome relevant to a particular chromosomal aneuploidy (e.g., trisomy 13, 18, or 21) over the amount or concentration of a fetal genetic marker located on a reference chromosome, as the amounts or concentrations are found in a biological sample (e.g., blood, plasma, or serum) from an average, healthy pregnant woman carrying a chromosomally normal fetus. In some case, a standard control is determined based on an average healthy pregnant woman at a certain gestational age, whereas in other cases, no distinction is made with regard to the gestational age.

The term "average," as used in the context of describing a pregnant woman, refers to certain relevant characteristics, such as the methylation profile of a particular gene or genomic sequence of both maternal and fetal origins found in the woman's blood, that are representative of a randomly selected group of healthy women who are pregnant with chromosomally normal fetuses and not suffering from any pregnancy-related diseases or conditions at the time of sample collection. This selected group should comprise a sufficient number of women such that the average amount or methylation profile of the gene of interest among these women reflects, with reasonable accuracy, the corresponding profile in the general population of healthy pregnant women with healthy fetuses. In addition, the selected group of women generally have a similar gestational age to that of a woman whose blood is tested for indication of a potential pregnancy-associated disorder. The preferred gestational age for practicing the present invention may vary depending on the disorder that is being screened for. For example, fetal chromosomal aneuploidy is preferably screened for and diagnosed as early as possible. Moreover, the preferred gestational age for testing may also depend on the gene of interest in testing.

The term "amount" as used in this application refers to the quantity of a polynucleotide sequence of interest, e.g., a genetic marker or an epigenetic/methylation marker of fetal origin, present in a sample. Such quantity may be expressed in the absolute terms, i.e., the total quantity (e.g. in mass, or in number of molecules) of the polynucleotide sequence in the sample, or in the relative terms (e.g. a ratio, or relative to other markers), or as the concentration (e.g. mass per unit volume, or number of molecules per unit volume) of the polynucleotide sequence in the sample.

DETAILED DESCRIPTION OF THE INVENTION

I. Introduction

The screening for trisomies such as trisomy 21 (T21) constitutes an important component in modern obstetrics care in many countries. The common screening methods that are routinely available in prenatal clinics target the epiphenomena associated with the chromosomal aneuploidy, rather than directly targeting the actual chromosome dosage in the fetus (Wapner et al., *N Engl J Med* 2003; 349:1405-13; Malone et al., *N Engl J Med* 2005; 353:2001-11). For a definitive test, invasive procedures, such as chorionic villus sampling and amniocentesis, are needed in conventional screening programs. These methods, however, can lead to procedure-related fetal loss (Tabor et al., *Lancet* 1986; 1:1287-93).

The discovery of cell-free fetal DNA in maternal plasma in 1997 has offered new possibilities for noninvasive prenatal diagnosis (Lo et al., *Lancet* 1997; 350:485-7; Lo and Chiu, *Nat Rev Genet.* 2007; 8:71-7). Detection of the fetal-derived, paternally-inherited genetic materials in maternal plasma samples has allowed the prenatal determination of fetal Rhesus D blood group (Lo et al., *N Engl J Med* 1998; 339: 1734-8; Finning et al., *BMJ* 2008; 336:816-8) and fetal sex determination for sex-linked disorders (Costa et al., *N Engl J Med* 2002; 346:1502). The development of noninvasive prenatal diagnostic tests for fetal chromosomal aneuploidies, however, has been more challenging.

Two main groups of approaches have been developed for the direct detection of T21 from maternal plasma nucleic acid analysis. The first group involves allelic ratio analysis of single nucleotide polymorphisms (SNPs) present in a fetal-specific nucleic acid marker (Lo and Chiu, *Nat Rev Genet.* 2007; 8:71-7). Examples of the latter include circulating placental mRNA (the so-called RNA-SNP approach) (Lo et al., *Nat Med* 2007; 13:218-23) and DNA methylation markers (the so-called epigenetic allelic ratio approach) (Tong et al., *Clin Chem* 2006; 52:2194-202). The main disadvantage of this approach is that these methods are only applicable to fetuses that are heterozygous for the analyzed SNP. Furthermore, there is a finite number of SNPs with sufficiently high heterozygosity rates within a particular locus so population coverage is a major challenge for this approach. The second group of approaches involves the use of single molecule counting approaches such as digital PCR (Lo et al., *Proc Natl Acad Sci USA* 2007; 104:13116-21) and massively parallel genomic sequencing (Chiu et al., *Proc Natl Acad Sci USA* 2008; 105:20458-63; Fan et al., *Proc Natl Acad Sci USA* 2008; 105:16266-71). In these approaches, individual plasma DNA molecules are counted. The precision of such methods allows the slight increase in chromosome 21-derived DNA molecules that is present in the plasma of a pregnant woman carrying a T21 fetus to be detected. One disadvantage of these approaches is that if used on markers with no fetal-specificity (e.g., random sequences from chromosome 21), then an extremely large number of molecules would need to be counted, as exemplified in recent experiments using massively parallel genomic sequencing when millions of molecules would need to be analyzed per case (Chiu et al., *Proc Natl Acad Sci USA* 2008; 105:20458-63; Fan et al., *Proc Natl Acad Sci USA* 2008; 105:16266-71). This latter requirement is associated with the use of expensive equipment and reagents, and relatively complex bioinformatics.

This application describes a new approach for the noninvasive prenatal detection of chromosomal aneuploidies (e.g., trisomy 21) from maternal plasma that is based on the determination of the ratio of the concentrations of a fetal-specific DNA methylation marker on chromosome potentially involved in the aneuploidy (e.g., chromosome 21) and a fetal-specific DNA marker on a reference chromosome. This is called the epigenetic-genetic (EGG) chromosome dosage approach. Compared with the epigenetic alleic ratio described above, the EGG approach does not require the fetal-specific DNA methylation marker and the SNP to be present within a short stretch of DNA and thus population coverage would be much easier to be achieved. The EGG approach is more precise than an approach based purely on epigenetic markers, the latter being typically performed with one on chromosome 21 and one on a reference chromosome.

For the EGG approach to work for trisomy detection, it is crucial to have a good fetal-specific DNA methylation marker on the relevant chromosome, such as chromosome 21, 18, or 13. One preferred type of markers would be one that is hyper-methylated in the fetus and hypomethylated in maternal blood cells, so that one can use methylation-sensitive restriction enzyme to digest away the maternal sequences. Indeed, previous work has shown that the promoter of the RASSF1A gene is one such marker, except that it is on chromosome 3 (Chan et al., *Clin Chem* 2006; 52:2211-8; Chiu et al., *Am J Pathol* 2007; 170:941-50). A number fetal DNA methylation markers on chromosome 21 has been reported (Chim et al., *Clin Chem* 2008; 54:500-11; Old et al., *Reprod Biomed Online* 2007; 15:227-35; Papageorgiou et al., *Am J Pathol* 2009; 174:1609-18). The present inventors searched for additional markers using combined bisulfite restriction analysis (COBRA) (Xiong and Laird, *Nucleic Acids Res* 1997; 25:2532-4) targeting 35 gene promoter regions on chromosome 21. This has led to the discovery of differential methylation of the putative promoter region of the *Holocarboxylase Synthetase* (biotin-(proprionyl-Coenzyme A-carboxylase (ATP-hydrolysing)) ligase) (HLCS) gene as a new hypermethylated fetal DNA marker. The EGG concept was then implemented using HLCS. The discovery of fetal-specific methylation markers on chromosomes 18 and 13 further permits the use of similar strategies for detection of trisomy 18 and 13.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of a genetic marker or genomic sequence used in this invention, e.g., the polynucleotide sequence of HLCS or ZFY gene, and synthetic oligonucleotides (e.g., primers) can be verified using, e.g., the chain termination method for sequencing double-stranded templates of Wallace et al., *Gene* 16: 21-26 (1981).

III. Acquisition of Blood Samples and Extraction of DNA

The present invention relates to analyzing the epigenetic-genetic chromosome dosage of appropriate fetal chromosomal DNA found in maternal blood as a non-invasive means to detect the presence and/or to monitor the progress of a pregnancy-associated condition or disorder. Thus, the first steps of practicing this invention are to obtain a blood sample from a pregnant woman and extract DNA from the sample.

A. Acquisition of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 mL, is collected and maybe stored according to standard procedure prior to further preparation.

B. Preparation of Blood Samples

The analysis of fetal DNA found in maternal blood according to the present invention may be performed using, e.g., whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. As alternatives to EDTA, heparin or citrate can be used as anticoagulants. On the other hand, serum may be obtained with or without centrifugation-following blood clotting. If centrifugation is used then it is typically, though not exclusively, conducted at an appropriate speed, e.g., 1,500-3,000×g. Plasma or serum may be subjected to additional centrifugation steps before being transferred to a fresh tube for DNA extraction. Instead or in additional to such centrifugation steps, it is also possible to use one or more filtration steps to remove particulate matters from plasma or serum.

In addition to the acellular portion of the whole blood, DNA may also be recovered from the cellular fraction, enriched in the buffy coat portion, which can be obtained following centrifugation of a whole blood sample from the woman and removal of the plasma. The cellular fraction can also be previously enriched for fetal nucleated cells circulating in maternal blood. Such enrichment procedures may include a sorting or selection procedure involving one or more antibodies against fetal cells or a procedure targeting physical, chemical, biochemical or other characteristics which can differentiate fetal from maternal cells. The sorting procedure can involve technologies such as the fluorescence activated cell sorter, magnetic activated cell sorting or microfluidics. The selection procedure can involve micromanipulation, or laser-captured microdissection, manipulation with optical tweezers or any other single cell manipulation procedure. Fetal cell types that can be targeted include nucleated red blood cells, lymphocytes, mononuclear cells, trophoblasts, or cellular remnants, e.g., apoptotic fetal cells.

C. Extraction of DNA

There are numerous known methods for extracting DNA from a biological sample including blood. The general methods of DNA preparation (e.g., described by Sambrook and Russell, *Molecular Cloning: A Laboratory Manual* 3d ed., 2001) can be followed; various commercially available reagents or kits, such as the QIAamp DNA Mini Kit or QIAamp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

IV. Methylation-Specific Modification of DNA

To properly identify the origin of an epigenetic marker or a genomic sequence (e.g., the HLCS gene) that is differentially methylated between the fetal and maternal DNA present in a sample, DNA isolated from the last step must be analyzed for their methylation status so as to distinguish the fetal and maternal DNA. Upon being extracted from a blood sample of a pregnant woman, the DNA is treated with a reagent capable of chemically modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996) and will not be discussed in detail here.

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfate restriction analysis (COBRA), may be used for practicing the present invention.

V. Polynucleotide Sequence Amplification and Determination

Following the modification of DNA in a methylation-differential manner, the treated DNA is then subjected to sequence-based analysis, such that the genomic sequence acting as the epigenetic marker (e.g., the HLCS gene) derived from the fetal DNA of a chromosome relevant to an aneuploidy may be distinguished from the same gene from the maternal DNA, and that the amount or concentration of the fetal gene in the sample may be quantitatively determined and compared to the amount or concentration of a genetic marker from a reference chromosome of fetal origin, and the ratio of the two is then compared to a standard control.

A. Amplification of Nucleotide Sequences

An amplification reaction is optional prior to the epigenetic marker's sequence analysis after methylation specific modification. In some embodiments of this invention, the amplification is performed to preferentially amplify a portion of the marker that has a particular methylation pattern, such that only the marker from one particular source, e.g., from the placenta or other tissues of the fetus, is detected and analyzed for its quantity or concentration. If desired, the amplification of a genetic marker on a reference chromosome that allows determination of fetal or maternal origin based on differences in polynucleotide sequence is carried out using known amplification methods that selectively amplify the fetal version of the marker sequence. Typically, preferential amplification is achieved by careful primer design.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available. Improved and more sensitive PCR methods such as real-time PCR and digital PCR are also useful in certain embodiments of the present invention.

Although PCR amplification of a target polynucleotide sequence (e.g., a portion of the epigenetic marker where the fetal and maternal sequence is differentially methylated) is typically used in practicing the present invention, one of skill in the art will recognize that amplification of the HLCS gene sequence found in a maternal blood sample may be accomplished by any known method, such as the ligase chain reaction (LCR), transcription-mediated amplification, and self-sustained sequence replication or nucleic acid sequence-based amplification (NASBA), each of which provides sufficient amplification. Branched-DNA technology may also be used to qualitatively demonstrate the presence of a particular marker sequence (which represents a particular methylation pattern or a particular polynucleotide sequence), or to quantitatively determine the amount or concentration of a particular marker sequence in the maternal blood. For a review of branched-DNA signal amplification for direct quantitation of nucleic acid sequences in clinical samples, see Nolte, *Adv. Clin. Chem.* 33:201-235, 1998.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

VI. Establishing a Standard Control

In order to establish a standard control for practicing the method of this invention, a group of healthy pregnant women carrying healthy fetuses is first selected. These women are within the appropriate time period of pregnancy for the purpose of screening for pregnancy-associated conditions such as fetal chromosomal aneuploidy and others using the methods of the present invention. Optionally, the women are of similar gestational age, e.g., within the same trimester of pregnancy, such as in the first or second trimester.

The healthy status of the selected pregnant women and the fetuses they are carrying are confirmed by well established, routinely employed methods including but not limited to general physical examination of the women, genetic analysis of the women, and fetal genetic analysis using CVS and amniocentesis.

Furthermore, the selected number of healthy pregnant women carrying healthy fetuses must be of a reasonable size, such that the average amount/concentration of fetal genetic and epigenetic markers in the maternal blood, the amount/concentration ratio, and the methylation profile of one or more of the epigenetic markers in the maternal blood obtained from the group can be reasonably regarded as representative of the normal or average level or methylation profile among the general population of healthy women carrying healthy fetuses. Preferably, the selected group comprises at least 10 women.

A fetal epigenetic marker methylation profile may reflect multiple different and separable aspects of the methylation status of this gene. For example, one aspect of a methylation profile is whether the C residue is methylated or not; another aspect is the number of methylated C bases within a particular region of the marker; a further aspect of the profile is the percentage(s) of methylated C at any given locations in a number of analyzed DNA molecules. Additional aspects of a methylation profile may include, but are not limited to, the allelic difference in methylation, the ratio of differentially methylated alleles, and the like. Fetal epigenetic marker methylation profile may also vary depending on the tissue type, e.g., placental or other fetal tissue. Thus, separate standard controls may be established for different fetal tissues used in testing.

Once an average value for the fetal epigenetic-genetic marker ratio is established for the particular set of fetal markers present in the maternal sample based on the individual values found in each woman of the selected healthy control group, this average or median or representative value or profile is considered a standard control. The samples taken from these healthy control women should ideally be taken prior to an invasive procedure. A standard deviation is also determined during the same process. In some cases, separate standard controls may be established for different aspects of the methylation profile of the epigenetic marker, such as based on different regions of the epigenetic marker sequence.

EXAMPLES

The following examples are provided by way of illustration only and not by way of limitation. Those of skill in the art will readily recognize a variety of non-critical parameters that could be changed or modified to yield essentially the same or similar results.

Example 1

I. Materials and Methods
Study Participants

Women with euploid and trisomy 21 pregnancies who attended the Department of Obstetrics and Gynaecology, Prince of Wales Hospital, Hong Kong, were recruited. Informed consent was obtained from individuals who joined the study, and ethics approval was obtained from the Joint Chinese University of Hong Kong—New Territories East Cluster Clinical Research Ethical Committee.
Screening of Differentially-Methylated Regions on Chromosome 21 By Cobra COBRA (Xiong and Laird, *Nucleic Acids Res* 1997; 25:2532-4) was used to assess the methylation status of genomic sequences on chromosome 21 in DNA samples from placentas and maternal blood cells.
Cloning and Bisulfite Sequencing Analysis of the Differentially-Methylated Locus Identified by Cobra PCR products from the COBRA analysis were used for cloning and bisulfite sequencing. To analyze methylation status at the resolution of a single molecule, the PCR product was TA-cloned into a plasmid vector using the pGEM-T Easy Vector System (Promega, Madison, Wis.). The inserts from the positive recombinant clones were PCR amplified using vector primers T7 and SP6, and were then analyzed by cycle sequencing using the BigDye Terminator Cycle Sequencing v1.1 kit (Applied Biosystems, Foster City, Calif.) according to the manufacturer's instructions. After ethanol precipitation, the samples were resuspended in 10 µL of Hi-Di formamide and run on a 3100 DNA Analyzer (Applied Biosystems). The sequencing data were analyzed using the SeqScape software (Applied Biosystems). The completeness of bisulfite conversion was confirmed before scoring. The methylated site frequency was calculated by dividing the total number of methylated CpG sites over all cloned CpG sites (Chiu et al., *Am J Pathol* 2007; 170:941-50).
Conventional Real-Time Quantitative PCR Analysis of the HLCS Locus Based on the COBRA screening and bisulfite sequencing results, we developed a methylation-sensitive restriction endonuclease (MSRE) digestion assay followed by real-time quantitative PCR analysis targeting the HLCS locus region B2, which is hypermethylated in the placenta and unmethylated in maternal blood cells. The use of enzyme digestion allowed the analysis of the methylation pattern of the HLCS locus in different genomic DNA samples. In addition, the background maternal DNA molecules in maternal plasma samples could be eliminated. The sequences for primers and probe for the real-time PCR assay are listed in Table 1.

Gene Dosage Analysis by the Microfluidics Digital PCR Platform

Gene dosage comparison of the chromosome 21 and the reference markers was analyzed by the polymerase chain reaction on a microfluidics digital PCR platform (Ottesen et al., *Science* 2006; 314:1464-7; Warren et al., *Proc Natl Acad Sci USA* 2006; 103:17807-12). The loci for an epigenetic-epigenetic comparison were HLCS on chromosome 21 and RASSF1A on chromosome 3 (Chiu et al., *Am J Pathol* 2007; 170:941-50). Both were hypermethylated fetal DNA markers. The loci for an epigenetic-genetic comparison were HLCS on chromosome 21 and ZFY on chromosome Y from pregnancies with a male fetus. The sequences of primers and probes with the PCR thermal cycle conditions for all the assays are listed in Table 1.
Statistical Analysis Statistical analyses were performed using the SigmaStat 3.5 software (SPSS).
Collection of Blood and Tissue Samples Chorionic villus samples (CVS) were collected during conventional prenatal diagnosis sessions in the first trimester of pregnancy. Placental tissue samples were collected from euploid third-trimester pregnancies after delivery and from euploid and trisomy 21 pregnancies after termination of pregnancy. The fetal chromosomal status was confirmed by full karyotyping. Maternal peripheral blood samples (12-20 mL EDTA) were collected from all subjects. An additional 12 mL of blood was collected into EDTA tubes from the third trimester pregnancies after delivery. Gestational ages of the first-, second- and third-trimester samples were 12-14 weeks, 17-21 weeks and 38-40 weeks, respectively.
Processing of Blood and Tissue Samples Maternal peripheral blood samples were processed by a double centrifugation protocol as previously described (Chiu et al., *Clin Chem* 2001; 47:1607-13). The blood cell portion was recentrifuged at 2,500 g, and any residual plasma was removed. DNA from the peripheral blood cells and that from maternal plasma was extracted with the blood and body fluid protocol of the QIAamp DNA Blood Mini Kit and the QIAamp DSP DNA Blood Mini Kit, respectively (Qiagen, Hilden, Germany). DNA from the CVS and placentas was extracted with the QIAamp DNA Mini Kit (Qiagen) according to the manufacturer's tissue protocol.
Screening of Differentially-Methylated Regions on Chromosome 21 By Cobra The COBRA procedure is described as follows. Bisulfite conversion was performed on one microgram of each DNA sample using the EZ DNA Methylation Kit (Zymo Research, Orange, Calif.) according to manufacturer's instructions. Forty nanograms of bisulfite-converted DNA (calculation based on the original DNA input) were then subjected to PCR amplification with reagents supplied in the HotStar Taq DNA Polymerase Kit (Qiagen, Hilden, Germany). Reagent compositions for each PCR are listed in Table 2. Typically, PCR was performed in a 20 µL reaction with 1×PCR Buffer, $MgCl_2$, 50 µM of each dNTP, forward and reverse primers, HotStar Taq polymerase, and with or without 2×PCRx Enhancer (Invitrogen, Carlsbad, Calif.). The thermal profile was 95° C. for 15 min, followed by 45-55 cycles of 95° C. for 20 s, appropriate annealing temperature for 30 s, 72° C. for 1.5 min, and a final extension of 72° C. for 3 min. PCR products were then subjected to restriction enzyme digestion. The restriction enzyme to be used for each respective locus was chosen for its ability to distinguish between the methylated and unmethylated sequences after bisulfite conversion. In essence, restriction sites were only present in either the methylated or unmethylated sequence but not both, so that one of the sequences would be digested while the other would remain intact. Restriction enzyme digestions were performed in 20 μL reactions with 5 μL PCR products, 1× appropriate buffer, and 10 U restriction enzyme (or none for mock digestion) under the manufacturer's recommended temperatures for 2 h. All enzymes were purchased from New England Biolabs (Ipswich, Mass.). Digested products were then analyzed by agarose gel electrophoresis.

Conventional Real-Time Quantitative PCR Analysis of the HLCS Locus

MSRE digestion. For each placental and maternal blood cell DNA sample, 100 ng DNA was subjected to MSRE digestion. Restriction enzyme digestion was performed in a 50 μL reaction with 1× appropriate buffer, 25 U of HpaII and 50 U of BstUI (or none for mock digestion) (New England Biolabs) under the manufacturer's recommended temperatures for at least 16 h. For each maternal plasma sample, 1.6 mL plasma was used for DNA extraction, and was eluted in 50 μL of deionized water, 21 μL of which was subjected to restriction enzyme digestion. Enzyme digestion was performed in a 30 μL reaction with 1× appropriate buffer, 20 U of HpaII and 30 U of BstUI (or none for mock digestion) under the manufacturer's recommended temperatures for at least 16 h. Digested products were then analyzed by real-time quantitative PCR. The selected restriction enzymes only digested the unmethylated DNA but not the methylated DNA. Since the data from the COBRA analysis have shown that HLCS is hypermethylated in placental tissues and unmethylated in maternal blood cells, it was expected that a proportion of DNA from placental tissues would remain detectable while most DNA from maternal blood cells would be digested, thus becoming undetectable after restriction enzyme treatment.

Real-time quantitative PCR analysis. Real-time PCR assay was developed for quantitative analysis of HLCS genomic DNA with and without restriction enzyme digestion. Four microliters of restriction enzyme treated DNA or mock digestion sample were used in the real time PCR assay. Each reaction contained 1× TaqMan Universal PCR Master Mix (Applied Biosystems), 300 nM of each of the forward and reverse primers (Integrated DNA Technologies, Coralville, Iowa), and 100 nM of the TaqMan probe (Applied Biosystems). The sequences of the primers and probes are listed in Table 1. The thermal profile was 50° C. for 2 min, 95° C. for 10 min, followed by 50 cycles of 95° C. for 15 s, and 60° C. for 1 min. All reactions were run in duplicates, and the mean quantity was taken. Serially-diluted human genomic DNA originally quantified by optical density measurement was used as the quantitative standard for the assay and the detection limit for the assay was 1 copy per reaction. As the detectable HLCS molecules after restriction enzyme digestion represented the methylated fraction, the real-time quantitative PCR was expressed as a methylation index. The methylation index of a sample was calculated by dividing the copy number of HLCS after enzyme digestion by that obtained with mock digestion. Maternal plasma DNA analysis was performed to show the postpartum clearance of the hypermethylated HLCS molecules.

Gene Dosage Analysis by the Microfluidics Digital PCR Platform

MSRE digestion. The MSRE, BstUI (New England Biolabs), was used to digest the hypomethylated DNA. Extracted DNA was digested with the BstUI enzyme at 60° C. for 16 h. For CVS, placental tissues and maternal blood cells, 40 U of BstUI enzyme was used to digest 200 ng of DNA for the microfluidics digital PCR assays. A mock-digested aliquot was included as the digestion control. For mock-digestion, an equal amount of DNA was subjected to the same digestion condition without the addition of enzyme. For the plasma samples, 20 U of the BstUI enzyme was used to digest the DNA from 3.4-4.8 mL plasma in the third-trimester samples. For the first- and second-trimester plasma samples, 40 U or 60 U of the BstUI enzyme was used to digest the DNA extracted from 4.4-9.1 mL plasma. The target sequences with the BstUI restriction sites underlined are illustrated in FIG. 5.

Microfluidics digital PCR analysis. Microfluidics digital PCR assays were designed for the HLCS, RASSF1A and ZFY loci (FIG. 5), representing the dosage of chromosome 21, chromosome 3 and chromosome Y, respectively. The ZFX/Y assay and the basis of the digital PCR analysis have been described previously (Lun et al., *Clin Chem* 2008; 54:1664-72). The sequences of the primers and probes are listed in Table 1. The digital experiments were carried out on the BioMark System (Fluidigm, South San Francisco, Calif.) using the 12.765 Digital Arrays (Fluidigm). The Digital Array consists of 12 panels, and each panel is further partitioned into 765 reaction wells. With each panel, the reaction was set up as a 10 μL mixture at a final concentration of 1× TaqMan Universal PCR Master Mix (Applied Biosystems), 125 nM TaqMan probe (Applied Biosystems), and 900 nM forward and reverse primers (Integrated DNA Technologies) diluted with the assay loading buffer and sample loading buffer according to the manufacturer's protocol. The input DNA volume was 3.5 μL for each of the 10 μL reaction mixture. The thermal profile was 50° C. for 2 min, 95° C. for 10 min, followed by 50 cycles of 95° C. for 15 or 30 s, and 57° C. or 60° C. for 1 min. The thermal cycle condition for each assay is specified in Table 1. The HLCS and RASSF1A assays were performed as a monoplex assay. The ZFX/Y assays were performed as a duplex reaction.

Assay specificity on the BstUI-digested genomic DNA samples. DNA samples from the CVS, placenta, and maternal blood cells were subjected to the HLCS, RASSF1A, and ZFX/Y digital PCR analysis after BstUI digestion. After enzyme digestion, the DNA was diluted to a concentration of 1-2 ng/μL for loading into the reaction mixture for digital PCR analysis. DNA samples from the CVS and placenta constituted enzyme digestion-resistant HLCS and RASSF1A molecules, thus signals should be detected after restriction enzyme digestion. On the other hand, we would expect no or low level of detection in the blood cells as they are hypomethylated at these two loci.

The ZFX/Y loci did not contain any BstUI enzyme digestion sites, thus restriction enzyme treatment should not confer any effects on the DNA molecules. The ZFY molecules constituted the fetal-derived sequences from a male fetus for the ratio comparison.

Assay specificity on the BstUI-digested plasma DNA samples. After BstUI-digestion on the maternal plasma DNA samples, a four-fold dilution with deionized water was performed. The samples were then mixed with the reaction mixture for loading onto the microfluidics chips for analysis.

Gene dosage comparison by the epigenetic-epigenetic approach and the epigenetic-genetic approaches. Digital PCR analyses of the HLCS, RASSF1A and ZFX/Y loci were performed on euploid and T21 placental DNA samples after BstUI restriction enzyme digestion. For maternal plasma analysis, we compared the ratio of HLCS to ZFY in BstUI-digested DNA samples from euploid and T21 pregnancies.

II. Results

Screening of Differentially-Methylated Regions on Chromosome 21 BY COBRA

Thirty-five promoter regions on chromosome 21 were selected for differential methylation screening using the COBRA method, thirty of which were not associated with CpG islands (CGIs) while the other five were associated with CGIs. The criteria to define a CGI were as follows: length >400 bp, GC content >50%, and observed/expected CpG ratio >0.6 (Yamada et al., *Genome Res* 2004; 14:247-66). DNA sequences proximal to the transcription start sites (−1 kb to +500 bp; transcription start site being 0) of the 35 promoters were obtained from the March 2006 human reference sequence of the UCSC Genome Bioinformatics Database (website: www.genome.ucsc.edu/) (NCBI Build 36.1), and designed 51 COBRA assays to compare the methylation patterns between placental tissues and maternal blood cells (Table 2).

Figure 6:
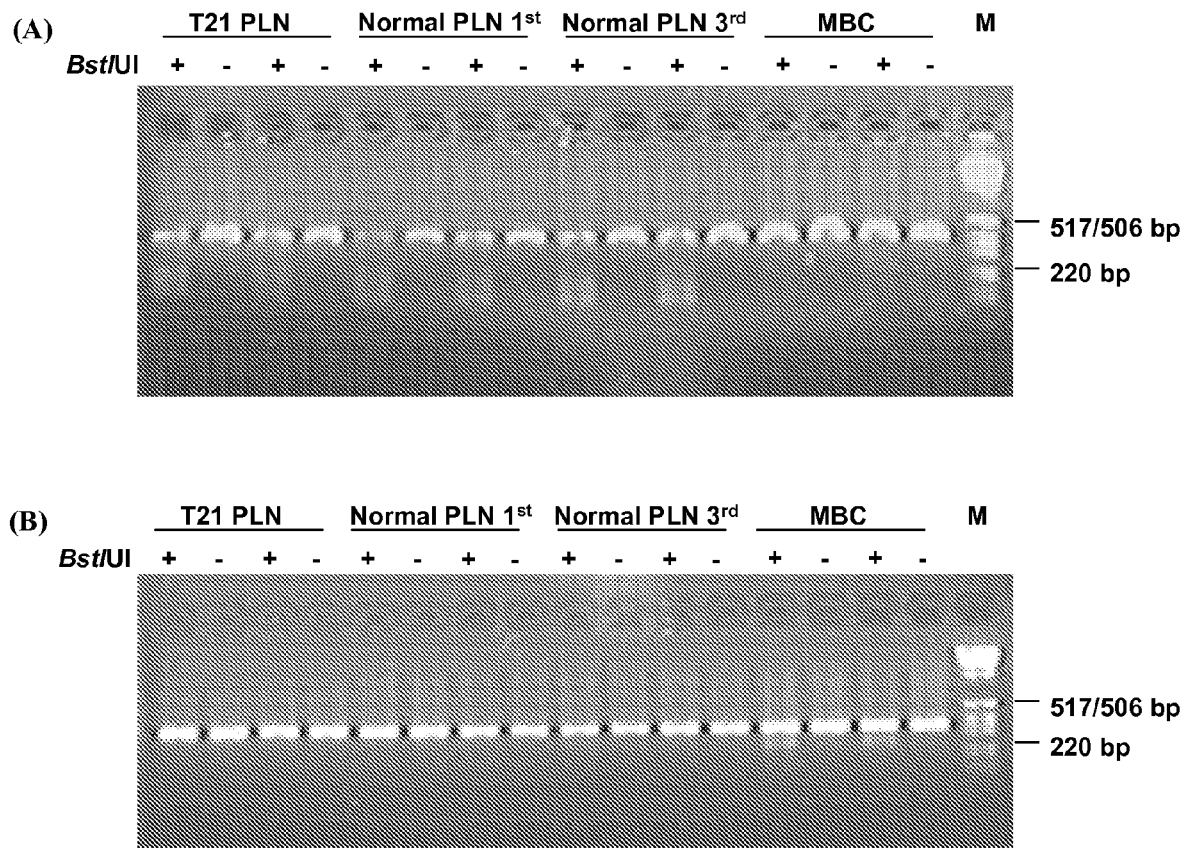
FIG. 6. Gel electrophoresis of COBRA results for (A) HLCS region B2, and (B) C21orf81. Two trisomy 21 placentas (T21 PLN), two first-trimester normal placentas (Normal PLN 1$^{st}$), two third-trimester normal placentas (Normal PLN 3$^{rd}$), and two first-trimester maternal blood cells (MBC) were analyzed. PCR products were incubated with (+) or without (−) the BstUI enzyme. DNA methylation was detected by the appearance of the smaller size digestion products. One kb ladder (Invitrogen Carlsbad, Calif.) (M) was used in gel electrophoresis.

Among the 51 assays, the methylation profiles of the promoter regions between placental tissues collected from the first- and third-trimesters and maternal blood cells were compared. At least one placental tissue and one maternal blood cell sample from normal pregnancies were used for the COBRA screening (Table 2). Among the screened regions, the putative promoter regions of HLCS and C21orf81 (GenBank accession AF326257) were identified by COBRA to be differentially-methylated between placental tissues and maternal blood cells. Representative COBRA results are illustrated in FIG. 6A for HLCS region B2, in which the placenta was hypermethylated when compared to maternal blood cells; and 6B for C21orf81, in which the maternal blood cells were slightly methylated when compared to placental tissues.

Cloning and Bisulfite Sequencing Analysis of the HLCS Locus

Cloning and bisulfite sequencing experiments were performed on the HLCS region for further analysis of the methylation status at the resolution of a single molecule, and the results are shown in FIG. 1. Sequencing results for the HLCS region confirmed that the hypermethylation of HLCS is placenta-specific with a methylated site frequency from 0.435 to 0.699. Although low methylation level was detected at the 3'-end (i.e., position −57 to +111, transcription start site being 0) of the target sequence in maternal blood cell samples (methylated site frequency <0.100), almost no methylation was observed for CpG sites from −232 to −67.

Real-Time Quantitative PCR for MSRE-Digested Placental, Maternal Blood Cell and Plasma DNA Samples Based on the COBRA and bisulfite sequencing data of the HLCS region B2, an MSRE digestion assay was developed followed by real-time quantitative PCR analysis to analyze the differential methylation of genomic DNA extracted from placentas and maternal blood cells.

Figure 7:
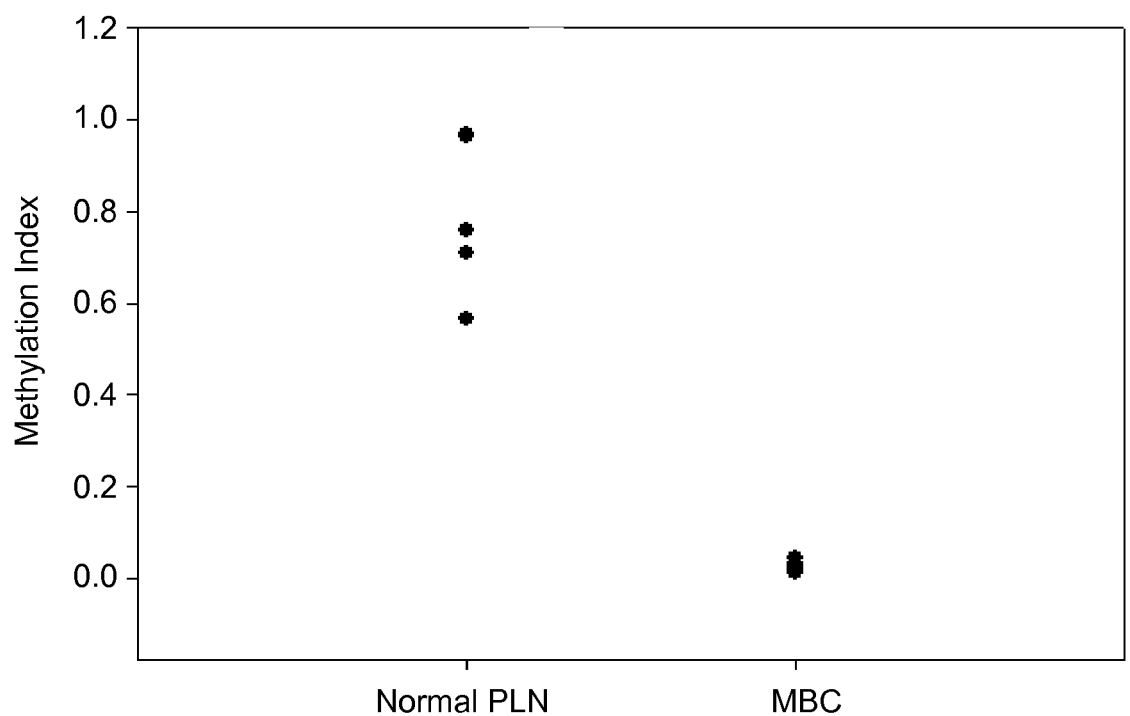
FIG. 7. Quantification of HLCS DNA from four placental tissues and eight maternal blood cells. The methylation index of a sample was calculated by dividing the copy number of HLCS after enzyme digestion by that obtained from mock digestion. "Normal PLN" represents placental DNA and "MBC" represents maternal blood cell DNA.

The methylation profiles of the putative promoter region of HLCS from eight maternal blood cell samples were compared with those from two first-trimester and two third-trimester placental tissue samples collected from euploid pregnancies. Restriction enzyme digestion followed by real-time quantitative PCR analysis was performed and the results are shown in FIG. 7. DNA from all maternal blood cell samples were mostly digested by restriction enzymes, resulting in methylation indices approaching 0 (Median: 0.0178, interquartile range (IQR): 0.0121-0.0281). Placental tissue DNA samples were partially digested, resulting in methylation indices ranging from 0.567 to 0.966.

Figure 8:
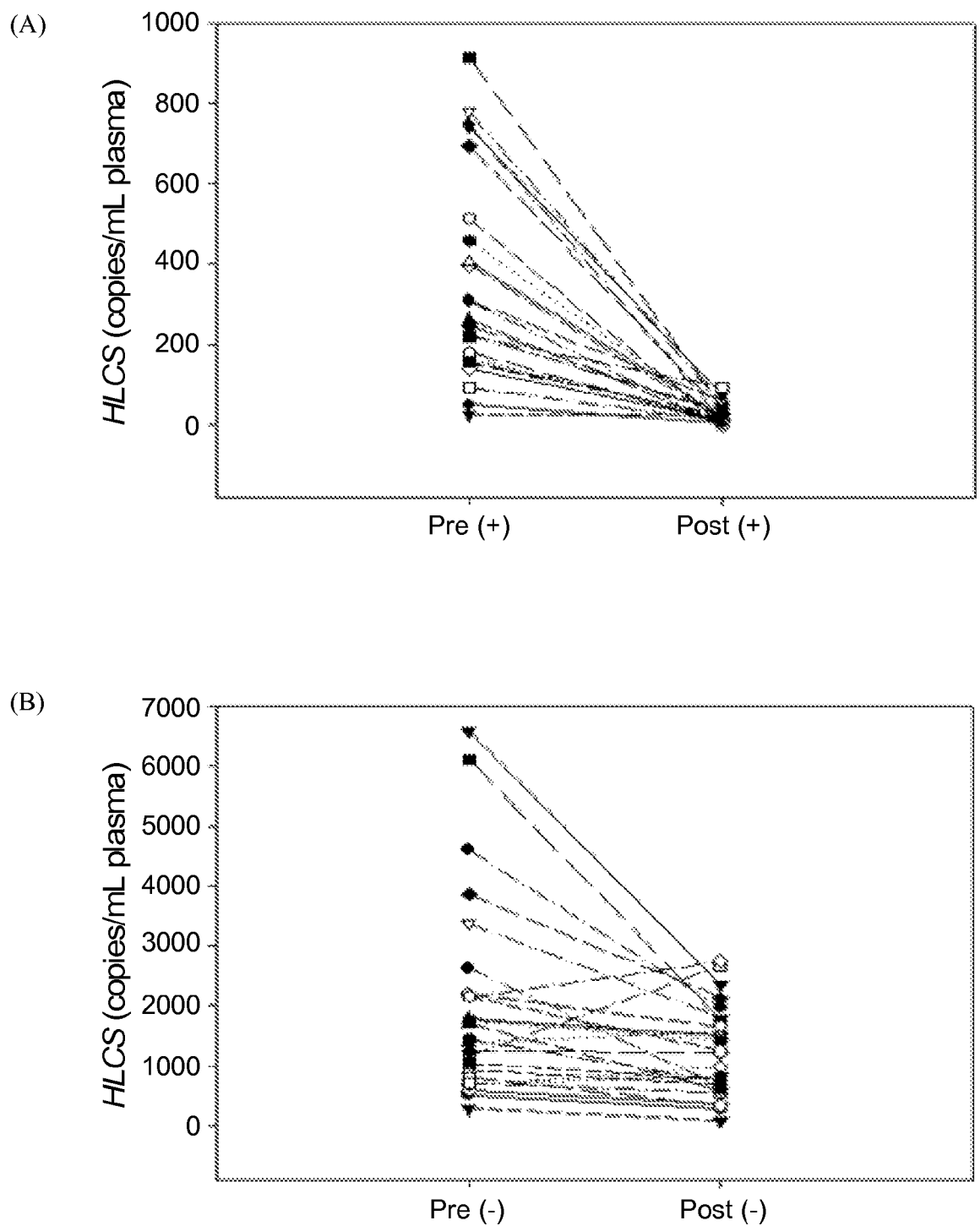
FIG. 8. Postpartum clearance in plasma. Detection of HLCS in maternal plasma samples (A) with (+), or (B) without (−) restriction enzyme digestion. "Pre" represents pre-delivery plasma samples and "Post" represents post-delivery plasma samples. Paired samples from the same subject are depicted by identical symbols connected by a line.

Previous data suggested that the placenta was the predominant source of fetal DNA (Bianchi, *Placenta* 2004; 25 Suppl A:S93-S101), while maternal blood cells were the main contributor of the background maternal DNA (Lui et al., *Clin Chem* 2002; 48:421-7) detectable in maternal plasma. It was therefore hypothesized that the placental-specific fraction of the HLCS DNA molecules, namely the methylated or non-digestible fraction, could be detected in maternal plasma. 25 pairs of pre- and post-delivery third-trimester maternal plasma samples were recruited, and restriction enzyme digestion followed by real-time quantitative PCR analysis were performed. The results are illustrated in FIG. 8. Positive HLCS signals were obtained in all of the enzyme-digested pre-delivery plasma samples. The clearance pattern from the enzyme-treated pre- and post-delivery plasma samples suggested that the digestion-resistant HLCS molecules were pregnancy-specific (P=<0.001, Wilcoxon signed-rank test). The median HLCS concentration in the post-delivery plasma samples was only 8.1% of that in the pre-delivery samples (20.1 vs. 247.8 copies/mL, respectively (FIG. 8A). For samples which underwent mock-digestions, the median HLCS concentration in the post-delivery plasma samples was 83.8% of that in the pre-delivery samples (1208.5 vs. 1442.4 copies/mL, respectively) (FIG. 8B). With mock-digestion, both the fetal and maternal DNA were detected in the pre-delivery plasma samples while only maternal DNA was counted in the post-delivery samples. It is noted that the difference in the HLCS concentration between pre- and post-delivery samples with mock digestion is statistically significant (P=0.003, Wilcoxon signed-rank test). Data from the BstUI digestion aliquot show that there were five maternal plasma samples having a relatively high level of fetal DNA, and these five samples were identical to the ones demonstrating a major drop in HLCS concentration in post-delivery sample even without enzyme digestion. This may contribute to the apparent "clearance" pattern even without enzyme digestion. The reduction of HLCS concentration observed in the post-delivery plasma samples might be due to some samples having unusually high levels of fetal DNA (P=0.003, Wilcoxon signed-rank test). It is noted that the five pre-delivery samples with extraordinarily high concentration of HLCS matched with the top five samples in the enzyme-digestion comparison.

Gene Dosage Analysis on the Microfluidics Digital PCR Platform

The gene dosage comparison of the chromosome 21 and reference chromosome markers was performed on a microfluidics digital PCR platform. The chromosome 21 marker was the hypermethylated HLCS, and the reference markers on chromosome 3 and chromosome Y were the hypermethylated RASSF1A and male-specific ZFY, respectively.

Two pairs of placental tissues and maternal blood cells samples were used to check the performance of the HLCS and RASSF1A assays with and without enzyme digestion. The ZFX/Y assay was also performed (GenBank accession of ZFX: NM_003410 and ZFY: NM_003411). Since there is no enzyme digestion site on these loci, it was expected the copy number would not be affected by the enzyme digestion. Two post-delivery maternal plasma samples were used to test the postpartum clearance of the digestion-resistant HLCS and RASSF1A molecules.

One panel for each assay was performed on each of the genomic DNA samples. For the post-delivery maternal plasma, enzyme-digested DNA was distributed into two panels for the scoring of any wells with positive signals. Results for the genomic DNA and plasma DNA samples are summarized in Tables 3A and 3B, respectively. The number of wells that were positive for each target locus were counted. The actual number of molecules distributed into the panel followed the Poisson distribution, and was corrected by the following equation:

$$\text{Target} = -\ln[E/N] \times N,$$

where Target is the Poisson-corrected counts of the target molecules, ln is the natural logarithm, E is the number of negative (empty) wells, and N is the total number of digital PCR wells in the reaction.

Results from the BstUI-digested placental DNA samples showed that about 60%-70% of the HLCS and RASSF1A molecules remained detectable when compared to the mock-digested samples. In the maternal blood DNA, the hypomethylated RASSF1A molecules were completely digested by BstUI enzyme treatment, while a few HLCS molecules remained detectable in the samples. For the ZFY and ZFX assays, there was no change in the copy number counted from the mock- or BstUI-digested DNA samples (Table 3A).

Post-delivery maternal plasma analysis showed that extremely low levels of both the HLCS and RASSF1A molecules were detected after BstUI enzyme digestion (Table 3B).

Figure 3:
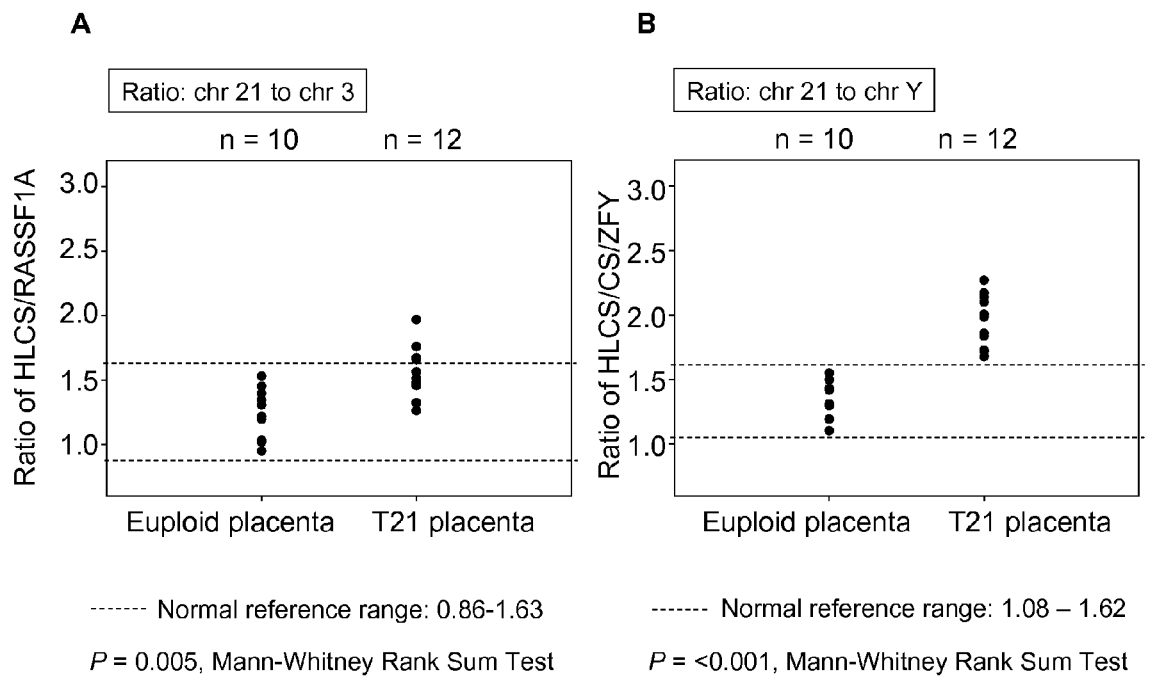
FIG. 3. Gene dosage comparison in euploid and trisomy 21 placental tissue DNA samples. (A) Ratios of HLCS to RASSF1A. (B) Ratios of HLCS to ZFY. The normal reference range is depicted by the dotted lines.

Gene Dosage Comparison in Placental DNA Samples by MSRE Digestion Followed by Digital PCR Analysis The HLCS and RASSF1A assays were applied to ten euploid and 12 trisomy 21 placental DNA samples (Table 4A). Four panels were counted for each assay (FIG. 2A). The ratios of the number of positive HLCS and RASSF1A amplifications in the euploid and T21 samples were statistically significantly different (P=0.005, Mann-Whitney Rank Sum Test). However, there was a large overlap between the two groups (FIG. 3A). A normal reference range, defined as the mean HLCS to RASSF1A ratio±1.96SD, was calculated from the euploid samples as 0.86-1.63. More than half of the T21 cases fell within the reference range. The heterogeneity in the methylation density of the two loci across different samples may contribute to the large inter-individual variation in the HLCS to RASSF1A ratio. To solve this precision problem, a more stable baseline would be required for the dosage comparison between the euploid and T21 DNA samples.

A fetal-specific locus which is independent of its methylation status, namely the ZFY locus, was then explored to serve as a baseline for the gene dosage comparison in pregnancy involving a male fetus. This is an important feature of the epigenetic-genetic (EGG) approach.

The same restriction enzyme-digested placental DNA samples used for the HLCS and RASSF1A comparison were subjected to the ZFY digital PCR analysis (FIG. 2A). The total copy number from four panels was used as the reference baseline for the total copy number of the HLCS molecules obtained above. A normal reference range, defined as the mean HLCS to ZFY ratio±1.96SD, was calculated from the euploid samples as 1.08-1.62. All the T21 samples showed a higher ratio than the normal reference range (FIG. 3B).

Gene Dosage Comparison in Maternal Plasma DNA Samples by MSRE Digestion Followed by Digital PCR Analysis The EGG technique was then applied to maternal plasma DNA samples from euploid and T21 pregnancies to determine whether the EGG approach can be applied for noninvasive prenatal detection of fetal trisomy 21. It was reasoned that while the maternal HLCS molecules in the maternal plasma was restriction digested by the BstUI enzyme, leaving the fetal-derived hypermethylated HLCS molecules intact for analysis, the fetal-derived ZFY locus would not be affected as there was no BstUI enzyme recognition site located within the PCR amplicon, thus providing a stable baseline for gene dosage comparison.

Eight maternal plasma samples were obtained from each of the third-, second-, and first-trimester pregnancies with a euploid fetus. After BstUI digestion, each DNA sample was analyzed in at least six panels on the microfluidics chips for the HLCS and ZFY assays (FIG. 2B). The total number of positive wells was used to calculate the ratio of HLCS to ZFY in each sample (Table 4B).

Figure 4:
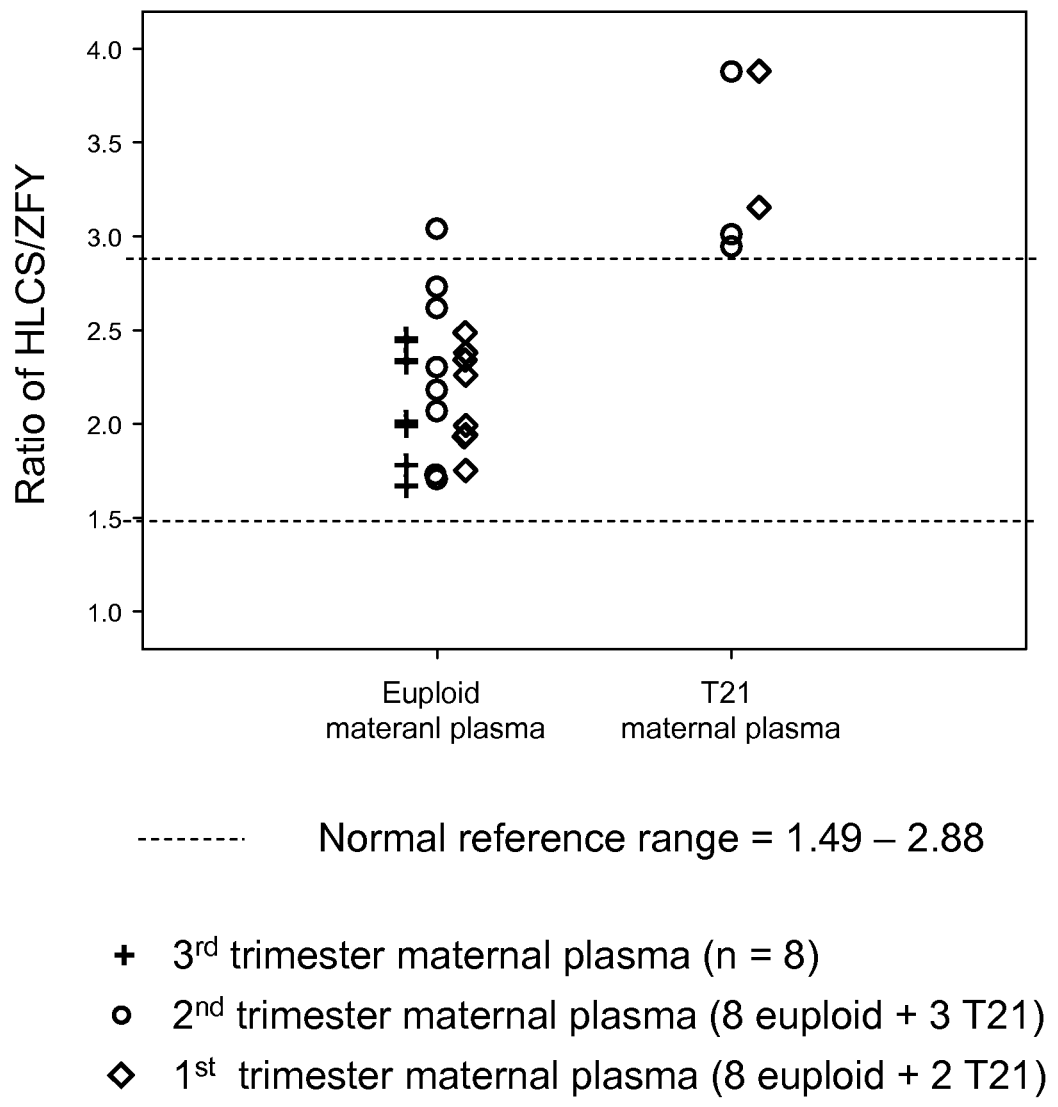
FIG. 4. Gene dosage comparison in euploid and trisomy 21 maternal plasma DNA samples. The ratios of HLCS to ZFY were plotted for each sample. The normal reference range is depicted by the dotted lines.

A normal reference range of 1.49-2.88 was calculated from the 24 maternal plasma samples with euploid pregnancies. The ratio of one euploid DNA sample fell out of the normal reference range. This sample dried up during Speedvac concentration, and was reconstituted with water during sample preparation, which might explain the inaccuracy. All five maternal plasma samples from T21 pregnancies had a higher ratio of HLCS to ZFY than the reference range (FIG. 4). The data showed that with the EGG approach, fetal trisomy 21 can be detected noninvasively in maternal plasma samples.

III. Discussion

In the first part of this study, the present inventors have successfully validated a hypermethylated fetal DNA marker on chromosome 21, namely, the promoter region of the HLCS gene (US Patent Application Publication No. 2007/0275402). The hypermethylated nature of this marker allows it to be detected relatively easily in maternal plasma through the use of methylation-sensitive restriction enzyme digestion and PCR amplification.

HLCS was then used to demonstrate that the novel EGG approach is a feasible method for fetal chromosome dosage analysis. The main advantage of the EGG method over the previously epigenetic allelic ratio analysis (Tong et al., *Clin Chem* 2006; 52:2194-202) is that using this method one has bypassed the requirement of the latter method for the epigenetic target and the genetic target (i.e., the SNP) to be present in the same locus and within a short distance from one another. In this study, the ZFY gene on the Y chromosome was used as a model for the fetal-specific genetic target. In practice, however, any fetal-specific genetic target, e.g., an SNP allele that the fetus has inherited from the father but absent in the pregnant mother, can be used. A panel of such markers would be relatively easily developed to ensure a broad population coverage of this approach.

It was also demonstrated that the EGG approach has a higher discrimination power for T21 than an approach based purely on epigenetic markers, using the ratio of the hypermethylated HLCS to hypermethylated RASSF1A as an example. One possible explanation of the suboptimal performance of the latter approach is because of the fact that there is a variability in the level of DNA methylation of individual fetal-derived HLCS and RASSF1A molecules, as can be seen in FIG. 1 and in previously published bisulfite sequencing results (Chiu et al., *Am J Pathol* 2007; 170:941-50). Thus, one would expect that a ratio determined from these two potentially varying parameters would have a wider reference interval than if one of the parameter is a relatively stable genetic marker (as in the case for the EGG approach).

In this study, microfluidics digital PCR was used as the detection and measurement platform because previous results have shown it to be a highly precise analytical method (Lun et Clin Chem 2008; 54:1664-72; Lun et al., *Proc Natl Acad Sci USA* 2008; 105:19920-5). The EGG approach can also be implemented in other variation of this molecular counting theme, e.g., by targeted sequencing using a 'next-generation' sequencer.

The development of fetal epigenetic markers on the other chromosomes important for prenatal screening, e.g., chromosomes 18 and 13, would further broaden the usefulness of the EGG approach. One example of a fetal epigenetic marker is the SERPINB5 gene, coding for maspin, on chromosome 18 (Chim et al., *Proc Natl Acad Sci USA* 2005; 102:14753-8). Other examples of fetal epigenetic markers on chromosome 18 and 13 are described by Papageorgiou et al. (Papageorgiou et al., *Am J Pathol* 2009; 174:1609-18).

Example 2

A novel epigenetic-genetic chromosome dosage approach is recently developed for fetal trisomy 21 detection using a fetal epigenetic marker, the putative promoter of *holocarboxylase synthetase* (HLCS) on chromosome 21, and a fetal genetic marker, the zinc finger protein, Y-linked (ZFY) gene present on chromosome Y (Tong et al., *Clin Chem* 2010; 56:90-8). To demonstrate that this method can be used for the detection of both male and female fetuses, the inventors have explored the use of a paternally-inherited fetal single nucleotide polymorphism (SNP) allele on a reference chromosome to serve as the baseline for epigenetic-genetic chromosome 21 dosage determination in place of the chromosome Y marker.

I. Materials and Methods

Study Participants

Women with euploid and trisomy 21 (T21) pregnancies who attended the Department of Obstetrics and Gynaecology, Prince of Wales Hospital were recruited between October 2009 and March 2010. Informed consent was obtained from individuals who joined the study, and ethics approval was obtained from the Joint Chinese University of Hong Kong—New Territories East Cluster Clinical Research Ethical Committee.

Chorionic villus samples (CVS) were collected during conventional prenatal diagnosis sessions in the first trimester of pregnancy. Placental tissue samples were collected from euploid third-trimester pregnancies after delivery and from T21 pregnancies after termination of pregnancy (TOP). The chromosome status of each T21 case was confirmed by full karyotyping. Maternal peripheral blood samples (12 mL in EDTA tubes) were collected from all subjects.

Processing of Blood and Tissue Samples

Peripheral blood samples were processed by a double centrifugation protocol as previously described (Chiu et al. *Clin Chem* 2001; 47:1607-13). The blood cell portion was recentrifuged at 2,500 g, and any residual plasma was removed. DNA from the peripheral blood cells and that from maternal plasma was extracted with the blood and body fluid protocol of the QIAamp DNA Blood Mini Kit and the QIAamp DSP DNA Blood Mini Kit, respectively (Qiagen).

DNA from the CVS and placentas was extracted with the QIAamp DNA Mini Kit (Qiagen) according to the manufacturer's tissue protocol.

Chromosome Dosage Analysis

Chromosome dosage comparison of the chromosome 21 and the reference marker in placental tissue and maternal plasma DNA samples was analyzed by real-time quantitative polymerase chain reaction (qPCR) and digital PCR (Vogelstein and Kinzler *Proc Natl Acad Sci USA* 1999; 96:9236-41), respectively. Chromosome dosage analysis was performed by comparing the amount of hypermethylated HLCS to that of a SNP allele (rs6636, a C/G SNP) that the fetus has inherited from the father but absent in the pregnant mother. SNP rs6636 is located within the transmembrane emp24 protein transport domain containing 8 (TMED8) gene on chromosome 14 with an average heterozygosity of 0.451+/−0.149 (dbSNP build 130). rs6636 is one of the SNPs that have been previously described (Chow et al. Clin Chem 2007; 53:141-2). The rs6636 SNP assays are denoted as TMED8-C/G SNP assays in this document.

Methylation-Sensitive Restriction Endonuclease (MSRE) Digestion

A methylation-sensitive restriction endonuclease, BstUI (New England Biolabs), was used to digest the hypomethylated DNA. Extracted DNA was digested with the BstUI enzyme at 60° C. for 16 hours. For CVS, placental tissues and maternal and normal control blood cells, 40 U of BstUI enzyme was used to digest 100 ng of DNA for the PCR assays. A mock-digested aliquot was included as the digestion control. For mock-digestion, an equal amount of DNA was subjected to the same digestion condition without the addition of enzyme. For the plasma samples, 20 U to 40 U of the BstUI enzyme was used to digest the DNA from 1.6-5.2 mL plasma.

Assay Design and Reaction Conditions for Conventional Real-Time QPCR Analysis

Real-time PCR analysis was performed for the HLCS and TMED8 loci. The sequences of the primers and probes are listed in Table 5. The HLCS, TMED8-C allele and TMED8-G allele assays were all performed as a monoplex reaction. Within the PCR amplicon of the HLCS locus, there were two BstUI enzyme recognition sites. In contrast, the TMED8 SNP assays did not contain any BstUI enzyme recognition sites.

Each reaction was set up as a 25 µL mixture at a final concentration of 1× TaqMan® Universal PCR Master Mix (Applied Biosystems), 100 nM TaqMan® probe (Applied Biosystems), and 300 nM of each of the forward and reverse primers (Integrated DNA Technologies) with 25 ng DNA input. The reaction was initiated at 50° C. for 2 min and continued at 95° C. for 10 min and followed by 40 cycles of 95° C. for 15 s and 60° C. for 1 min. The experiments were carried out on the 7300 Real-time PCR System (Applied Biosystems) and the fluorescence data were collected and analyzed by the SDS v1.3.0 software (Applied Biosystems). All reactions were run in duplicates with the mean quantity taken. A calibration curve was constructed by serially-diluted genomic DNA extracted from adult male blood cells with concentration ranging from 10000 genome equivalents (GE) to 3 GE per reaction.

Assay Design and Reaction Conditions for the Digital PCR Analysis

The same oligonucleotide sequences for real-time PCR analysis were used for the HLCS and TMED8-C/G SNP digital PCR analysis (Table 5). Here, the HLCS assay was performed as a duplex reaction with each of the TMED8-C/G SNP assays. The fluorescent probes were labeled as HLCS (VIC) duplex with TMED8-C(FAM) and HLCS(FAM) duplex with TMED8-G(VIC).

The basis of the digital PCR analysis have been described previously (Lo et al. *Proc Natl Acad Sci USA* 2007; 104: 13116-21; Lun et al. Clin Chem 2008; 54:1664-72). The total reaction volume was 5 µL per well in a 384-well plate at a final concentration of 1× TaqMan® Universal PCR Master Mix (Applied Biosystems), 100 nM TaqMan® probe (Applied Biosystems), and 300 nM of each of the forward and reverse primers (Integrated DNA Technologies). The reaction was initiated at 50° C. for 2 min and continued at 95° C. for 10 min and followed by 50 cycles of 95° C. for 15 s and 60° C. for 1 min. The experiments were carried out on the 7900HT Sequence Detection System (Applied Biosystems) in a 384-well format, and the fluorescence data were collected by the "Absolute Quantification" application of SDS 2.3 software (Applied Biosystems).

Specificity of the TMED8-C/G SNP Assay

Genomic DNA extracted from placental tissues with known TMED8 genotypes were subjected to the HLCS and TMED8 duplex assays. Samples that were homozygous for one allele were tested with the TMED8-C/G SNP assay for the other allele. A sample homozygous for the C allele should not show any signals for the TMED8 assay detecting the G allele, and vice versa.

Beta-Actin Assay as a Digestion Control

A previously-described beta-actin region that is unmethylated in both the placenta and maternal blood cells was used to determine the efficiency of BstUI digestion (Chan et al. *Clin Chem* 2006; 52:2211-8). The beta-actin assay was modified to contain two BstUI enzyme recognition sites to match the number of BstUI enzyme recognition sites of the current HLCS assay. The sequences of the primers and probes are listed in Table 5. The same sequences were used for both the real-time qPCR and digital PCR analyses.

Statistical Analysis

Statistical analyses were performed using the SigmaStat 3.5 software (SPSS).

II. Results and Discussion

Chromosome Dosage Analysis by Conventional Real-Time qPCR

The HLCS and TMED8-C/G SNP assays were applied to a total of 20 euploid and nine T21 placental tissue samples with the heterozygous C/G genotype. Six euploid and four T21 samples were analyzed by using the HLCS to TMED8-C ratio, and the remaining 14 euploid and five T21 samples were analyzed by the HLCS to TMED8-G ratio. A calibration curve constructed by serially-diluted genomic DNA extracted from adult male blood cells with concentration ranging from 10000 GE to 3 GE per reaction was used to determine the absolute copy number of the two loci in the tested samples.

All three assays were optimized to have similar efficiencies, as indicated by the slopes and y-intercepts of the calibration curves. The slopes of the calibration curves of the HLCS, TMED8-C and TMED8-G assays were −3.71, −3.70 and −3.62, respectively, whereas the y-intercepts showed threshold cycle values of 39.62, 39.79 and 42.04, respectively.

HLCS to TMED8-C Ratio in Placental DNA Samples

Figure 9:
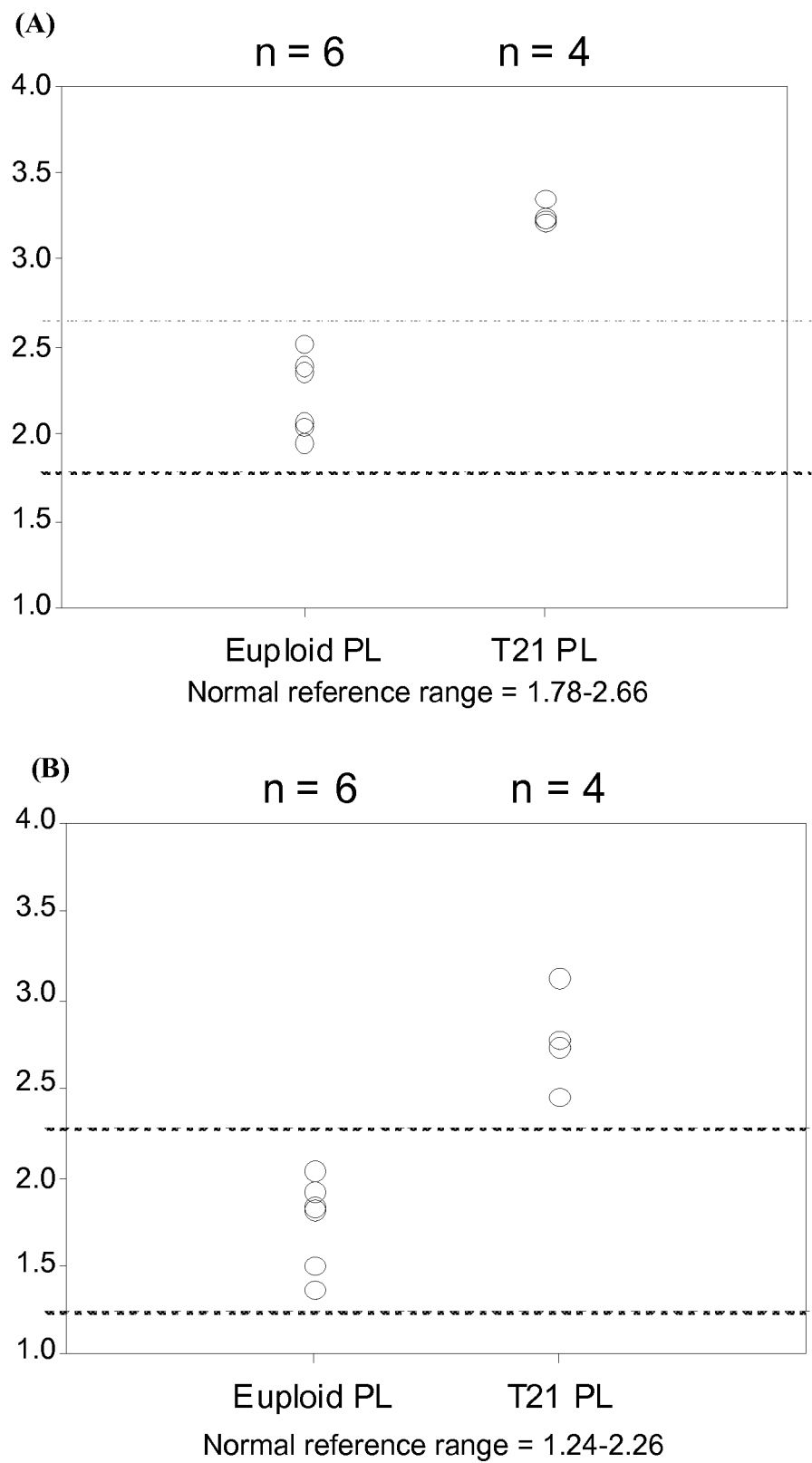
FIG. 9. Chromosome dosage comparison in euploid and trisomy 21 placental tissue DNA samples by determining the ratio of (A) HLCS to TMED8-C with mock digestion, and (B) HLCS to TMED8-C with BstUI digestion. The normal reference range is depicted by dotted lines.
Figure 11:
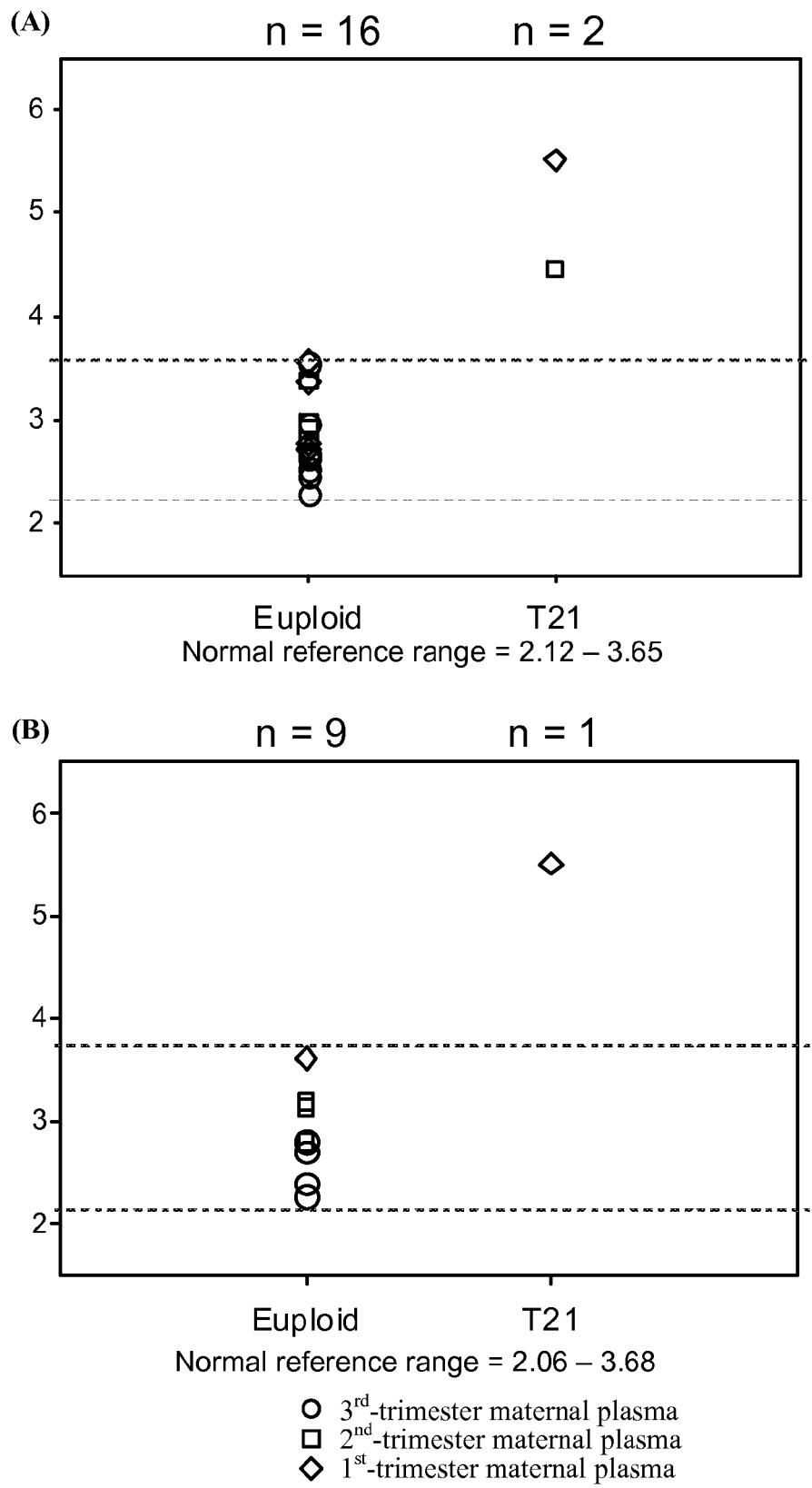
FIG. 11. Chromosome dosage comparison in BstUI-digested, euploid and trisomy 21 maternal plasma DNA samples by determining the ratio of (A) hypermethylated HLCS to TMED8-C allele, and (B) hypermethylated HLCS to TMED8-G allele. The normal reference range is depicted by dotted lines.

The HLCS to TMED8-C ratio was first determined in mock-digested placental DNA samples. A normal reference range, defined as the mean HLCS to TMED8-C ratio±1.96SD, was calculated from the six euploid samples as 1.78-2.66. All four T21 samples showed a higher ratio than the normal reference range (Table 6A) (FIG. 9A).

The same samples were then subjected to BstUI restriction enzyme digestion before real-time PCR analysis. While the unmethylated HLCS molecules would be digested by BstUI enzyme treatment, leaving only the digestion-resistant, hypermethylated HLCS molecules for PCR detection, the TMED8 molecules would remain intact as there was no BstUI enzyme recognition site within the TMED8 PCR amplicon. A normal reference range was calculated as 1.24-2.26. All samples were correctly classified (Table 6B) (FIG. 9B).

In both the mock and BstUI digestion experiments, a placental DNA sample with the homozygous GG genotype for the TMED8 SNP was included for testing the assay specificity. There was no signal when the TMED8 assay for detecting the C allele was applied (Table 6A and 6B).

HLCS to TMED8-G Ratio in Placental DNA Samples

The HLCS to TMED8-G ratio was first determined in mock-digested placental DNA samples. A normal reference range was calculated from the 14 euploid samples as 1.36-3.03. One sample from each of the euploid and T21 groups was misclassified (Table 7A) (FIG. 10A).

The same samples were then subjected to BstUI restriction enzyme digestion before real-time PCR analysis. A normal reference range was calculated as 0.90-1.99. One sample from each of the euploid and T21 groups was misclassified (Table 7B) (FIG. 10B). These are not the same samples as the misclassified ones in the mock digestion experiment.

In both mock and BstUI digestion experiments, a placental DNA sample with the homozygous CC genotype for the TMED8 SNP was included for testing the assay specificity. There was no signal when the TMED8 assay for detecting the G allele was applied (Table 7A and 7B).

Beta-Actin as a Digestion Control

The BstUI enzyme digestion efficiency was evaluated by applying the beta-actin assay to the same mock- and BstUI-digested placental DNA samples as those used for HLCS to TMED8 chromosome dosage analysis. The same calibration standard was used to quantify the amount of beta-actin sequences in the samples. The slope of the calibration curve was −3.41, whereas the y-intercept showed threshold cycle value of 37.97. Results showed that over 96% of the DNA was digested in all tested samples (Table 8A and 8B).

Chromosome Dosage Analysis by Digital PCR

Specificity of the TMED8-C/G SNP Assay

Placental DNA samples of the heterozygous C/G, homozygous C/C and homozygous G/G genotypes were tested with the HLCS and TMED8 duplex assay to ascertain the specificity for detecting either one of the SNP alleles. Two samples were used for each of the three groups. A sample homozygous for the C allele should not show any signals for the TMED8 assay detecting the G allele, and vice versa.

The number of wells that were positive for each of the target loci was counted. The total number of molecules distributed into the 384-well plate followed the Poisson distribution, and was corrected as previously described (Tong et al. *Clin Chem* 2010; 56:90-8).

By applying the HLCS and TMED8-C duplex assay, placental DNA samples of the heterozygous C/G and homozygous C/C genotypes showed positive wells for both loci, whereas samples of the homozygous G/G genotypes were only positive for the HLCS locus, and no detectable signal was observed for the TMED8-C allele (Table 9A).

By applying the HLCS and TMED8-G duplex assay, placental DNA samples of the heterozygous C/G and homozygous G/G genotypes showed positive wells for both loci, whereas samples of homozygous C/C were only positive for the HLCS locus, and no detectable signal was observed for the TMED8-G allele (Table 9B).

The results showed that the TMED8-C/G SNP assays were specific in detecting the individual SNP allele. The specificity was conferred by the allele-specific probes labeled with difference fluorescent dyes.

HLCS to TMED8-C Ratio in Maternal Plasma DNA Samples

Maternal plasma DNA analysis was performed by comparing the ratio of digestion-resistant HLCS to fetal-specific TMED8 SNP allele in informative samples. An informative sample was defined as one in which the fetus was heterozygous and the mother was homozygous, being the TMED8-C/G SNP in the current example. The extra allele that the fetus had inherited from the father was used as the reference baseline for chromosome 21 dosage determination.

The HLCS and TMED8-C duplex assay was applied to a total of 16 euploid and two T21 pregnancies. In these samples, the fetal and maternal genotypes for the TMED8 SNP were C/G and G/G, respectively. The fetal-specific SNP allele was the C allele. Maternal plasma DNA samples were analyzed by digital PCR after BstUI enzyme digestion. Each sample was analyzed in at least one 384-well plate. The total number of positive wells was used to calculate the ratio of HLCS to TMED8-C allele in each sample.

A normal reference range of 2.12-3.65 was calculated from the euploid maternal plasma samples. Eight samples were collected from the third-trimester, and four samples were collected from each of the second- and first-trimester pregnancies. Among these 16 euploid samples, ten were from pregnancies carrying a female fetus, and six from those carrying a male fetus. The HLCS to TMED8-C allele ratios of all euploid samples fell within the reference range. The T21 samples collected from the second- and first-trimester pregnancies showed a higher ratio than the reference range (FIG. 7A). Both T21 cases carried a female fetus.

HLCS to TMED8-G Ratio in Maternal Plasma DNA Samples

In the other group of informative samples, the fetal and maternal genotypes for the TMED8 SNP were C/G and C/C, respectively. The fetal-specific SNP allele was the G allele. The HLCS and TMED8-G duplex digital PCR assay was applied to BstUI-digested maternal plasma DNA samples from nine euploid pregnancies and one T21 pregnancy. Each sample was analyzed in at least one 384-well plate. The total number of positive wells was used to calculate the ratio of HLCS to TMED8-G allele in each sample.

A normal reference range of 2.06-3.68 was calculated from euploid maternal plasma samples. Among the nine euploid samples, five, three and one cases were collected from the third-, second- and first-trimester pregnancies, respectively. They included four pregnancies with a female fetus, and five with a male fetus. The HLCS to TMED8-G allele ratios of all euploid samples fell within the reference range. The first-trimester T21 pregnancy with a female fetus showed a higher HLCS to TMED8-G ratio than the reference range (FIG. 7B).

Beta-Actin as a Digestion Control

The BstUI enzyme digestion efficiency was evaluated by applying the beta-actin digital PCR assay to the same BstUI-digested maternal plasma DNA samples as those used for HLCS to TMED8 chromosome dosage analysis. An aliquot of the digested DNA samples (1/50 of the total digestion mixture) was confirmed to show no more than one positive well for the beta-actin assay before subjected to chromosome dosage analysis.

III. Conclusion

In an earlier example, the inventors have demonstrated in principle that the EGG approach was a feasible method for fetal chromosome dosage analysis in maternal plasma DNA samples. The hypermethylated HLCS locus was used as the epigenetic component, which represented a class of fetal-specific molecules, and the ZFY locus was a genetic marker which was specific to a male fetus. By comparing the ratio between the fetal-specific epigenetic marker on chromosome 21 and the fetal-specific genetic marker on a reference chromosome, the chromosome 21 dosage could be deduced.

In this example, we further demonstrated that the epigenetic-genetic chromosome dosage approach can be applied to the prenatal diagnosis of trisomy 21 using a fetal-specific SNP allele as a genetic reference baseline in place of a chromosome Y marker derived from a male fetus.

Here, SNP rs6636 located within the TMED8 locus on chromosome 14 was used as an example. By comparing the ratio between the hypermethylated HLCS and the fetal-specific TMED8 SNP allele, the chromosome 21 dosage could be deduced. It was demonstrated that both SNP alleles could serve as such a genetic reference baseline.

By using an informative SNP allele as the genetic reference baseline, the EGG chromosome dosage approach can be applied to the prenatal diagnosis of trisomy 21 for both male and female fetuses. Furthermore, development of a panel of such markers will ensure a broad population coverage of this approach. As previously described (Chow et al. *Clin Chem* 2007; 53:141-2), one could first test a maternal buffy coat sample, which comprises of mostly maternal DNA, to ascertain the maternal genotypes for the panel of SNPs. For SNPs where the mother was shown to be homozygous, one could then aim to detect the allele that is not represented in the maternal genotype in maternal plasma. If the plasma sample is positive for the non-maternal allele, it suggests that the fetus has inherited that allele from the father. The quantification of that paternally inherited fetal-specific allele in maternal plasma could then be used as the reference for gene dosage assessment using the peigenetic-genetic approach. Finally, the use of epigenetic markers for the other chromosomes involved in other aneuploidies important for prenatal testing, e.g., chromosomes 18 and 13, will further expand the clinical utility of the EGG approach.

Example 3

Epigenetic-Genetic Chromosome Dosage Approach for the Detection of Fetal Trisomy 18

This example demonstrates the application of epigenetic-genetic (EGG) chromosome dosage approach for the detection of fetal trisomy 18 (T18). This example of the EGG approach involved a fetal epigenetic marker located on chromosome 18 and a fetal genetic marker located on a reference chromosome, respectively, in maternal plasma. The fetal epigenetic marker is, preferably, Marker 18A [genomic location chr18:10022533-10022724, defined according to the Human Genome March 2006 Assembly (hg18)], which is a 146-bp intergenic region located 75 kb downstream of the gene VAPA (vesicle-associated membrane protein)-associated protein A) and 421 kb upstream of the gene APCDD1 (adenomatosis polyposis coli down-regulated 1), as identified by an methylated DNA immunoprecipitation and tiling array analysis (described in U.S. Ser. No. 61/308,578). However, this fetal epigenetic marker can also be any cytosine-containing DNA genomic region located within 100 kb upstream or downstream of the above locus, i.e., chr18:10022533-10022724. Furthermore, this fetal epigenetic marker can also be any cytosine-containing DNA genomic region with different epigenetic signature (DNA methylation levels) that distinguishes the fetal from the maternal chromosome 18 in maternal plasma.

The fetal genetic marker in maternal plasma is, preferably, a region located in the zinc-finger Y-linked (ZFY) gene on chromosome Y. However, this fetal genetic marker can also be any genetic differences between the fetus and its mother, including single-nucleotide polymorphism (SNP) and insertion/deletion (indel) polymorphism.

In this example, the inventors adopted the EGG approach to compare the concentrations of Marker 18A on chromosome 18 with those of a fetal genetic marker, the zinc finger protein, Y-linked (ZFY) gene on chromosome Y for the non-invasive prenatal detection of T18.

I. Materials and Methods

Sample Collection

Samples were obtained from women attending the Department of Obstetrics and Gynaecology at the Prince of Wales Hospital, Hong Kong, or the Prenatal Diagnostic and Counselling Department at the Tsan Yuk Hospital, Hong Kong, or the Harris Birthright Research Centre for Fetal Medicine, at the King's College Hospital, London, UK. All of the pregnancies were recruited with informed consent. The study was approved by the respective institutional review boards.

Chorionic villus samples (CVS) were collected during conventional prenatal diagnosis sessions in the first and second trimesters of pregnancy. The chromosome status of each euploid and T18 case was confirmed by full karyotyping.

Maternal peripheral blood samples (12 mL in EDTA tubes) were collected from all subjects. Plasma from the UK was harvested, kept frozen and sent to Hong Kong in batches on dry ice.

Sample Processing

Peripheral blood samples were processed by a double centrifugation protocol as previously described (Chiu et al. *Clin Chem* 2001; 47:1607-13). The blood cell portion was recentrifuged at 2,500 g, and any residual plasma was removed.

DNA from the peripheral blood cells and that from maternal plasma was extracted with the blood and body fluid protocol of the QIAamp DNA Blood Mini Kit and the QIAamp DSP DNA Blood Mini Kit, respectively (Qiagen). DNA from the CVS and placentas was extracted with the QIAamp DNA Mini Kit (Qiagen) according to the manufacturer's tissue protocol.

Analysis of Marker 18A Methylation Status in Placenta and Maternal Blood Cells

DNA Methylation Analysis by Cloning and Bisulfite Sequencing

The methylation status of Marker 18A were analyzed in six pairs of placental tissues and maternal blood cells by cloning and bisulfite sequencing. Briefly, extracted DNA was bisulfite-converted using the EZ DNA METHYLAYION™ Kit (ZymoResearch) according to the manufacturer's instructions. Bisulfite-converted DNA was subjected to PCR amplification by primers targeting the Marker 18A region. The primer sequences for the PCR are listed in Table 10. The PCR conditions are summarized in Table 11A. The PCR product was subsequently TA-cloned into a plasmid vector with the PGEM T-EASY™ Cloning Kit (Promega) according to manufacturer's instructions. Cloning was done with *Escherichia coli* strain JM109 (Promega). The inserts from the clones were then amplified using T7 and SP6 promoter primers (Promega) according to the manufacturer's instructions (Reaction conditions are summarized under the sub-title colony PCR assays in Table 11A). The PCR product was then subjected to sequencing reaction with the BIGDye® Terminator Cycle Sequencing v1.1 kit (Applied Biosystems) according to the manufacturer's instructions (Reaction conditions are summarized under the sub-title sequencing reaction in Table 11A). DNA was then precipitated with ethanol and resuspended in 10 µL of Hi-Di formamide and sequenced on a 3100 DNA Analyzer (Applied Biosystems). The sequencing data were analyzed using the SEQSCAPE v2.5 software (Applied Biosystems). The inventors ensured >99% bisulfite conversion of each clone by examining the conversion rate at non-CpG cytosine residues.

The MI at each CpG site was calculated by the number of methylated clones divided by the total number of clones for each sample. The average MI of the two biological replicates was calculated for each CpG site. The methylated site frequency was given by the number of methylated clones across each sample over the total number of clones scored.

Analysis of Marker 18A Methylation Status in T18 and Euploid Placentas

DNA Methylation Analysis by the Epityper Assay

The EPITYPER™ assay was performed with the standard MASSCLEAVE™ protocol (Sequenom) (Ehrich et al. *Proc Natl Acad Sci USA* 2005; 102:15785-90) (Details of the conditions for individual reactions involved in the protocol are summarized in Table 11 B). Briefly, the bisulfite-converted DNA was subjected to PCR amplification with the Epityper assay targeting Marker 18A. The primer sequences were listed in Table 10. A T7 promoter tag was added to the 3' end of the reverse primer, and a 10-base tag was added to the 5' end of the primer to equalize the melting temperature between the forward and reverse primers. Extracted DNA was subjected to bisulfite conversion with an EZ DNA METHYLATION™ Kit (ZymoResearch) according to the manufacturer's instruction and amplified with PCR. The PCR products were then in vitro transcribed as RNA using the T7 DNA polymerase and T7 RNA polymerase, and cleaved specifically at bases with A- or G-residues by RNase A. The cleavage reaction generated CpG-containing fragments, or CpG unit, whose sizes would be dependent on the methylation status of the CpG sites (i.e., CpG or TpG for methylated and unmethylated CpGs, respectively, after bisulfite conversion). The products were then cleaned up, and resolved with a matrix-assisted laser desorption/ionization time-of-flight (MALDI-TOF) mass spectrophotometer (MassARRAY™ Analyzer Compact). The methylation index (MI) of each CpG unit were calculated by dividing the peak height of the methylated product by the sum of peak heights of both the methylated and unmethylated products.

Detection of Methylated Marker 18A Sequences in Pre- and Post-Delivery Maternal Plasma Quantitative real-time PCR (qPCR) assays were designed to target Marker 18A. The primer and probes were strategically positioned such that the unmethylated CpG sites in maternal DNA, but not the methylated CpG sites in the fetal DNA, would be specifically cleaved by the relevant restriction endonucleases.

Methylation-Sensitive Restriction Endonuclesae (MSRE) Digestion

Two types of MSRE, namely HpaII and HinP1I (New England Biolabs), were used to digest the plasma DNA. For each plasma sample, DNA was extracted from 0.8 mL-3.2 mL plasma and eluted in 50 µL water. 35 µL of the eluted DNA was then incubated with 20 U each of HpaII and HinP1I (New England Biolabs) in 1×NEBuffer 1 at 37° C. for 2 hours.

Conventional Real-Time Quantitative PCR Analysis

1) Concentrations of Digestion-Resistant Marker 18A Before and after Delivery of the Fetus After digestion by MSRE, hypermethylated DNA sequences of Marker 18A were amplified by conventional qPCR on the ABI 7300 HT sequence detection system (Applied Biosystems). The reaction volume of each qPCR assay was 50 µL, which contained 1×TaqMan® Universal PCR Master Mix (Applied Biosystems), 1500 nmol/L of each forward and reverse PCR primers (Integrated DNA Technologies), and 250 nmol/L TAQMan® probe (Integrated DNA Technologies). The probe was labeled with FAM on its 5' end as reporter. The thermal profile was 50° C. for 2 min, 95° C. for 10 min, 40 cycles of 95° C. for 15 s, and 60° C. for 1 minute. The primer and probe sequences are listed in Table 12.

2) Relationship Between the Concentrations of Digestion-Resistant Marker 18A and Those of ZFY in Pre-Delivery Maternal Plasma Obtained from Pregnancies Involving Male Fetuses The concentrations of ZFY were determined by qPCR on the ABI7300 HT sequence detection system (Applied Biosystems) with a previously established assay (Lun et al. *Clin Chem* 2008; 54:1664-72). The reaction volume of each qPCR assay was 50 µL, which contained 1× TAQMan® Universal PCR Master Mix (Applied Biosystems), 300 nmol/L of each forward and reverse PCR primers, and 100 nmol/L TAQ-Man® probe (Applied Biosystems). The probe was labeled with VIC on its 5' end as reporter. The thermal profile was 50° C. for 2 min, 95° C. for 10 min, 40 cycles of 95° C. for 15 s, and 60° C. for 1 minute. The primer and probe sequences are listed in Table 12.

For quantification by qPCR analysis, a calibration curve was derived by serial dilutions of known concentrations of genomic DNA extracted from a male peripheral blood cell sample, which was quantified by NanoDrop ND-1000 (Thermo Fisher Scientific Waltham) using the DNA-50 setting. It was then used to construct the quantitative standards with a linear dynamic range from 3 copies per reaction to 10,000 copies per reaction. The limit of detection (LOD) was 3 copies per reaction. Twenty duplicated reactions (40 replicates) were performed at the LOD concentration and 100% of the wells were positive with a median quantification cycle of 39.1 (range: 38.2-40.8). Any signals detected beyond that limit were considered undetectable. All reactions were duplicated and the mean quantity was taken. Multiple water blanks (no template control) were included in every PCR run.

EGG Chromosome Dosage Analysis

The inventors adopted the EGG approach to compare the relative dosage of the fetal epigenetic marker, Marker 18A, on chromosome 18, and that of a fetal genetic marker, ZFY, on chromosome Y, in placental tissues (CVS) and maternal plasma samples obtained from euploid and T18 pregnancies.

Methylation-Sensitive Restriction Endonuclesae (MSRE) Digestion

The digestion protocol for the EGG analysis involving Marker 18A was the same as that used for qPCR analysis. For analyzing placental samples, 50 ng of DNA was subjected to digestion. All of the placental tissues were obtained from the first trimester. For analyzing plasma samples, DNA was extracted from 1.6 mL-3.2 mL plasma obtained from first, second and third trimester of euploid or T18 pregnancies. Extracted DNA from each case was eluted into 50 μL water, of which 35 μL was subjected to digestion.

Assay Design and Reaction Conditions for the Digital PCR Analysis

A duplex digital PCR assay was developed to amplify digestion-resistant Marker 18A and ZFY sequences. The basis of the digital PCR analysis have been described previously (Lo et al. *Proc Natl Acad Sci USA* 2007; 104:13116-21; Tong et al. *Clin Chem* 2010; 56: 90-8).

The reaction volume was 5 μL per well at a final concentration of 1× TAQMAN® Universal PCR Master Mix (Applied Biosystems) with the respective primers and probes concentrations for each target. For Marker 18A, the reaction involved 250 nM TAQMAN® probe (Integrated DNA Technologies) and 1500 nM of each of the forward and reverse primers (Integrated DNA Technologies). For ZFY, the reaction involved 100 nM TaqMan® probe (Applied Biosystems), and 300 nM of each of the forward and reverse primers (Integrated DNA Technologies). The probe for Marker 18A was labeled with the reporter FAM while that for ZFY was labeled with the reported VIC (Table 12). The total number of digital PCR reactions for each target was 384. The primer and probe sequences are the same as those for qPCR.

To evaluate the completeness of digestion, another digital PCR assay was developed to target a region on the beta-actin gene, which (i) is completely unmethylated in both placentas and maternal blood cells from the first trimester (FIG. 17); and (ii) contains similar number of recognition sites and type of MSRE as Marker 18A. The methylation status of this particular region was confirmed by cloned bisulfite sequencing (FIG. 17). The primer sequences for PCR amplification involved in bisulfite sequencing analysis were listed in Table 10. The reaction conditions were the same as that described for Marker 18A. No beta-actin sequences were expected to be detectable after a complete digestion. The reaction volume was 5 μL per well at a final concentration of 1× TAQMAN® Universal PCR Master Mix (Applied Biosystems) with 250 nM TAQMAN® probe (Applied Biosystems) and 900 nM of each of the forward and reverse primers (Integrated DNA Technologies). The probe was labeled with the reporter VIC at its 5' end (Table 10). The assay was carried out on the 7900HT Sequence Detection System (Applied Biosystems). The reaction was initiated at 50° C. for 2 min and continued at 95° C. for 10 min, followed by 55 cycles of 95° C. for 15 s, and 60° C. for 1 min. The total number of digital PCR reactions for each target was 96.

The fluorescence data of all the digital PCR assays were collected by the "Absolute Quantification" application of SDS 2.3 software (Applied Biosystems).

Statistical Analysis

Statistical analyses were performed with the SigmaStat 3.0 software (SPSS).

II. RESULTS

Marker 18A is a Potential Fetal Epigenetic Marker

Figure 12:
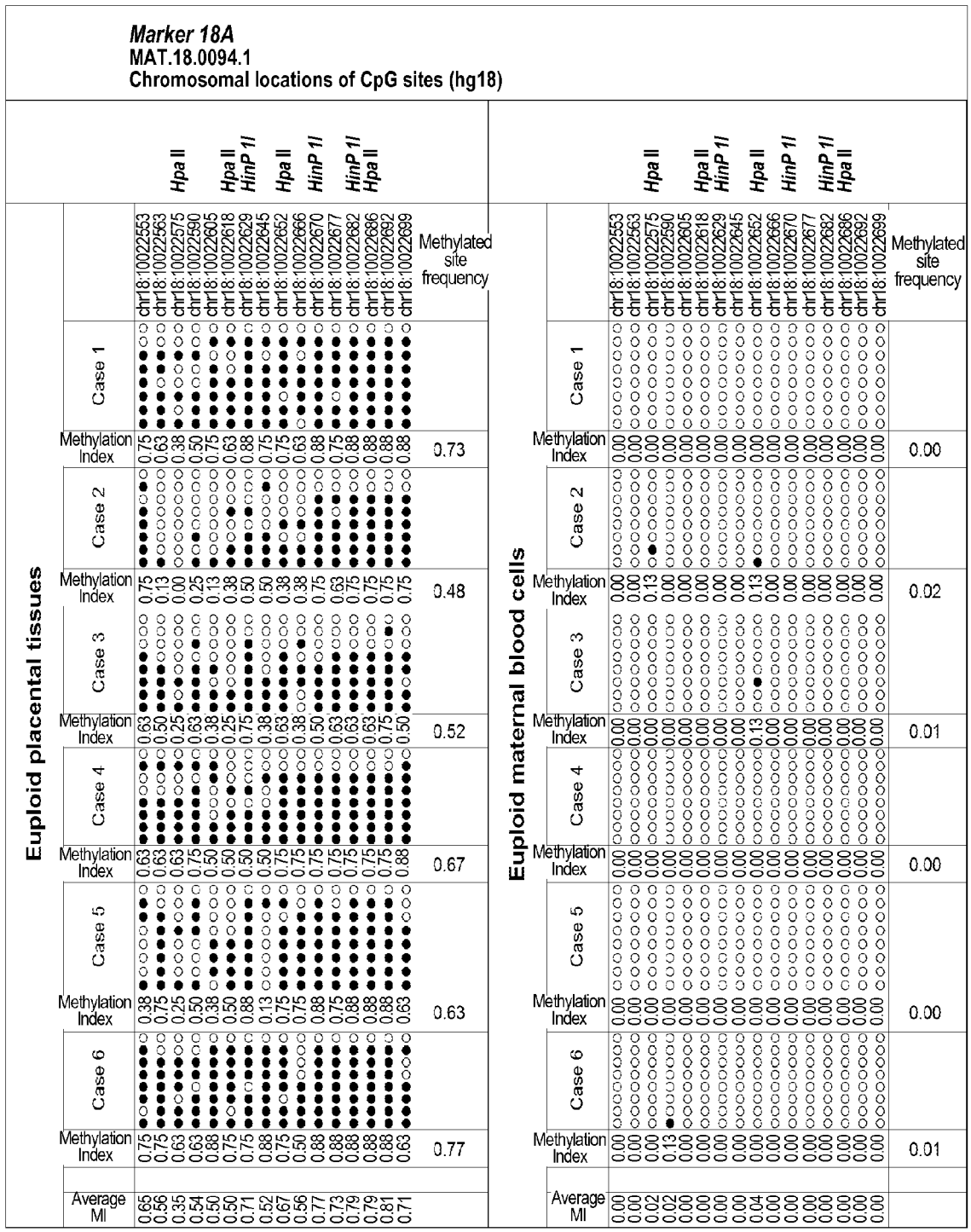
FIG. 12. DNA methylation levels of Marker 18A in 6 pairs of first-trimester euploid placentas and maternal blood cells determined by cloned bisulfite sequencing. A total of 8 clones were scored for each sample. The methylated sites are represented by a filled circle, while the unmethylated sites are represented by an empty circle. The methylation index (MI) at each CpG site was given by the number of methylated clones over the total number of clones at each CpG site. The methylated site frequency was given by the number of cloned methylated CpG sites over the total number of cloned CpG sites for each sample. The positions of the recognition sites of the methylation-sensitive restriction endonuclesae are marked next to each genomic location of the CpG site. The genomic locations were defined according to the Human Genome March 2006 Assembly (hg18) of the UCSC Genome Browser (genome.ucsc.edu).

Previous studies have shown that a genomic region that is differentially methylated between placenta and maternal blood cells has the potential to be developed into fetal epigenetic marker in maternal plasma (Chim et al. *Clin Chem* 2008; 54:500-11; Tong et al. *Clin Chem* 2010; 56:90-8). Cloning and bisulfite sequencing results revealed that Marker 18A is predominantly methylated in euploid placentas (n=6) and essentially unmethylated in maternal blood cells (n=6) (FIG. 12). The average methylation indices in the placentas and maternal blood cells are 0.68 and 0.01, respectively.

The inventors have also studied the methylation levels of Marker 18A in euploid (n=6) and T18 (n=6) placentas by the EPITYPER™. Mann Whitney Rank Sum Test was performed to compare the MIs of the euploid placentas with those of the T18 placentas at each CpG unit (FIG. 13). It was reasoned that if the methylation level of Marker 18A does not change significantly between euploid and T18 placentas, it can be used to compare the dosage of fetal chromosome 18 in euploid and T18 maternal plasma. It was found that within the target region of Marker 18A, all of the CpG units had no significant differential methylation between euploid and T18 placentas (FIG. 13).

Detection of Marker 18A in Maternal Plasma after Enzyme Digestion

Figure 14A:
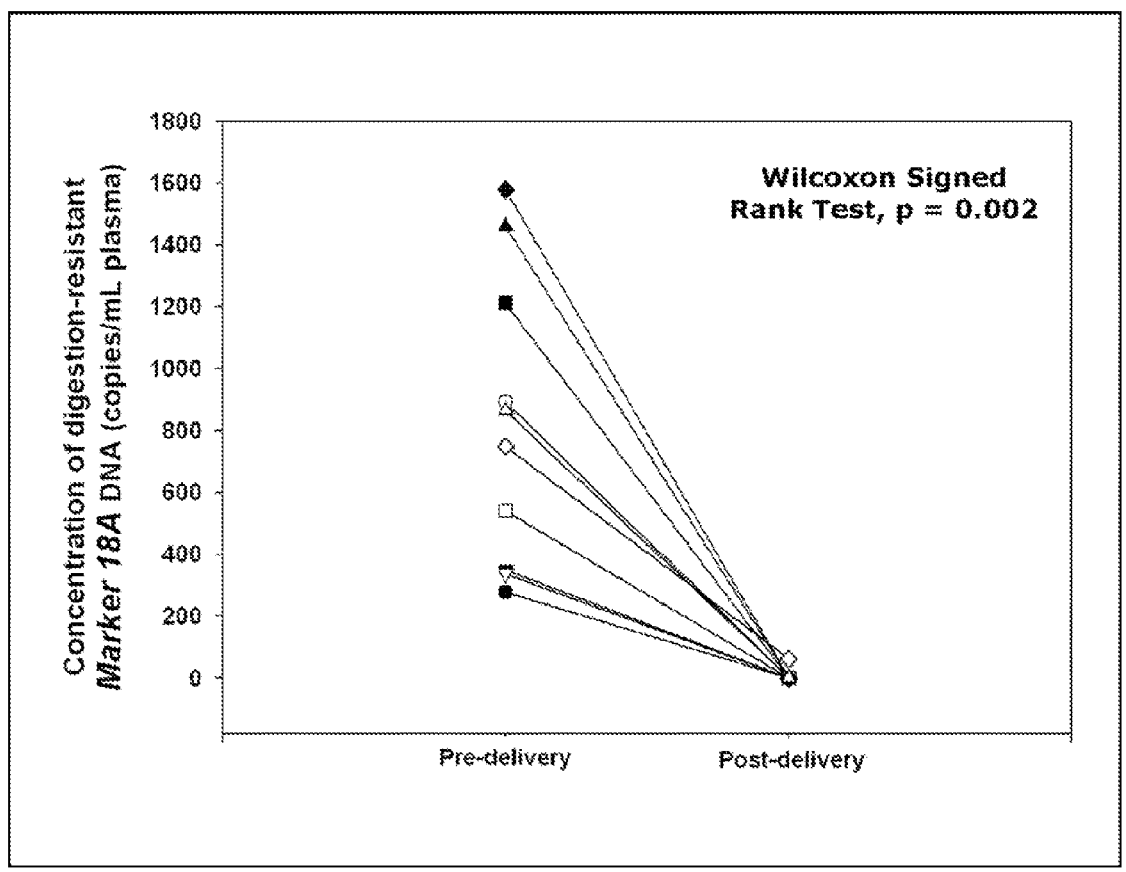
FIG. 14. Characterization of digestion-resistant Marker 18A sequences in maternal plasma (A) Concentrations of digestion-resistant Marker 18A DNA in maternal plasma before and after delivery of the fetus. (B) Correlation between concentrations of digestion-resistant Marker 18A DNA against the concentrations of an established fetal genetic marker, ZFY, in pregnancies bearing male fetuses.

The inventors analyzed and compared the concentrations of digestion-resistant Marker 18A in maternal plasma DNA obtained before delivery and at 24 hour post-delivery. Unmethylated beta-actin sequences were not detectable in every post-digestion sample, indicating digestion was completed. Before delivery of the fetus, the median concentrations of digestion-resistant Marker 18A sequences were 806 copies/mL in third-trimester pregnancies (n=10). After delivery, the plasma concentrations dropped below the detection limit of the assay, which was estimated to be 3 copies per reaction. The plasma concentrations of digestion-resistant Marker 18A sequences before and after delivery of the fetuses were statistically significantly different (Wilcoxon signed-rank test, P-value=0.002) (FIG. 14A).

Figure 14B:
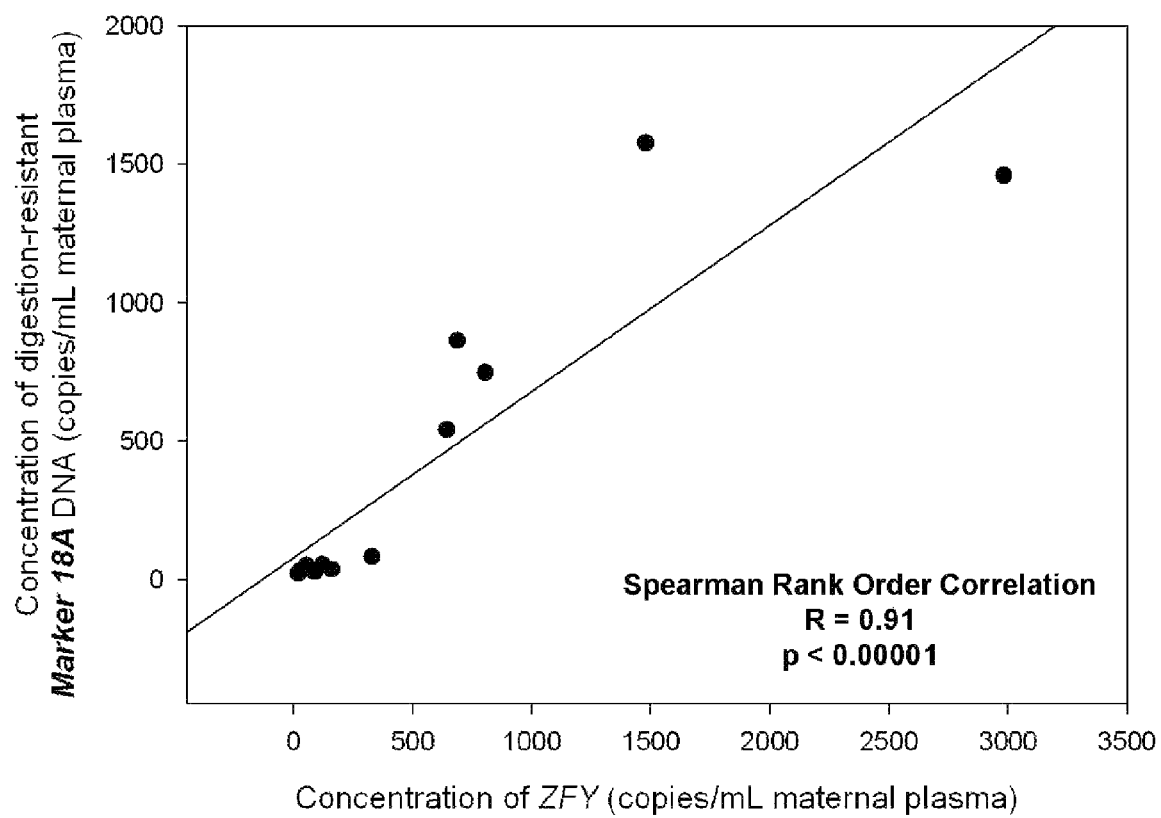

It has been further demonstrated that the plasma concentrations of digestion-resistant Marker 18A sequences were significantly correlated with those of the ZFY gene, an established fetal genetic marker, in pre-delivery (n=13, r=0.91; P-value <0.00001; Spearman correlation) (FIG. 14B). These results suggested that the digestion-resistant Marker 18A sequences in maternal plasma were derived from the fetus.

EGG Chromosome-Dosage Analysis

Marker 18A to ZFY Ratio in Placental DNA Samples

First-trimester placental DNA samples (5 for T18 and 5 for euploid) from pregnancies with male fetuses were analyzed with the duplex digital PCR assays for Marker 18A and ZFY.

Figure 15:
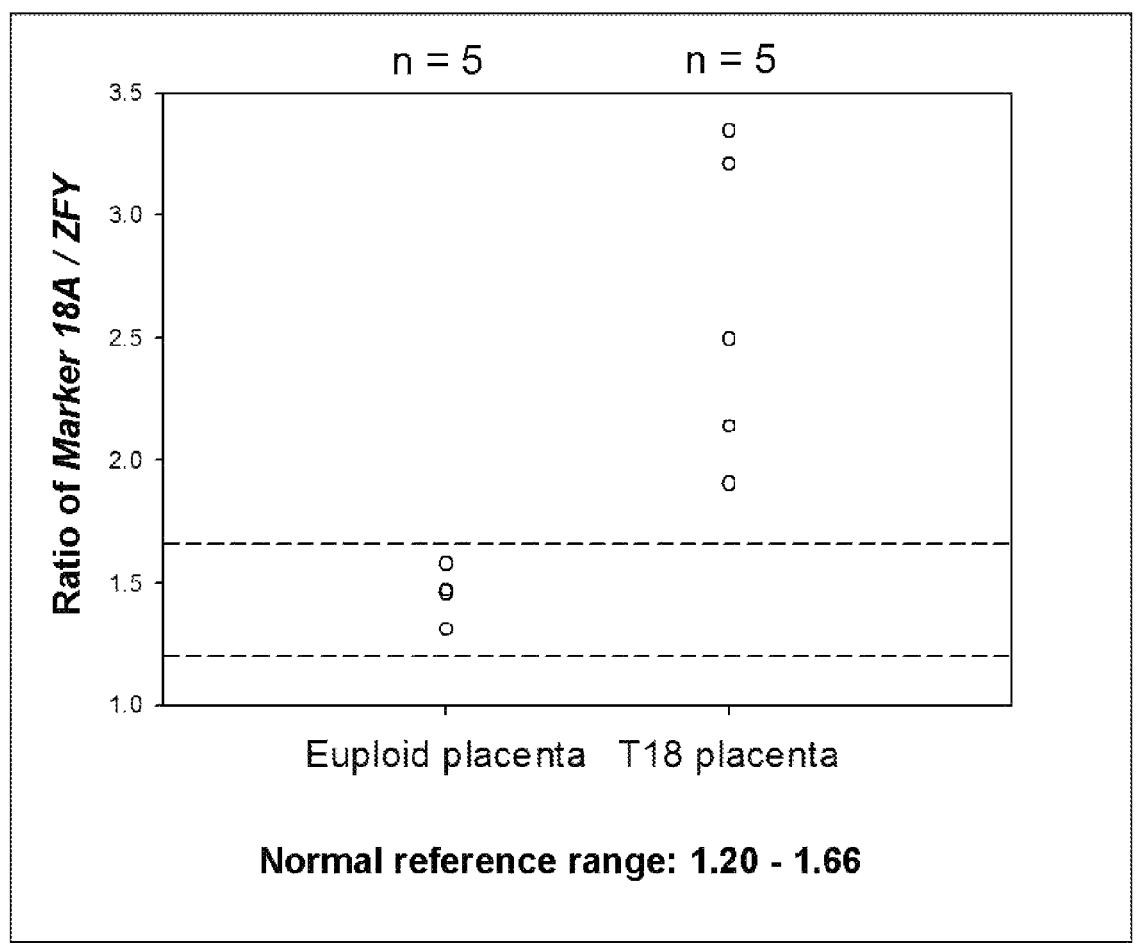
FIG. 15. Relative dosage of chromosome 18 (Marker 18A) to chromosome Y (ZFY) in euploid (n=5) and trisomy 18 (T18) (n=5) placental DNA samples. The normal reference range (mean±1.96SD) is depicted by the dotted lines.

The ratios of Marker 18A to ZFY in euploid and T18 samples were significantly different (Mann Whitney Rank Sum Test, P-value=0.023); The normal reference range, defined as the mean ratio of Marker 18A to ZFY±1.96SD, for the euploid samples was 1.20-1.66. All of the T18 cases had a ratio greater than the upper reference limit (FIG. 15).

Marker 18A to ZFY Ratio in Maternal Plasma Samples

Figure 16:
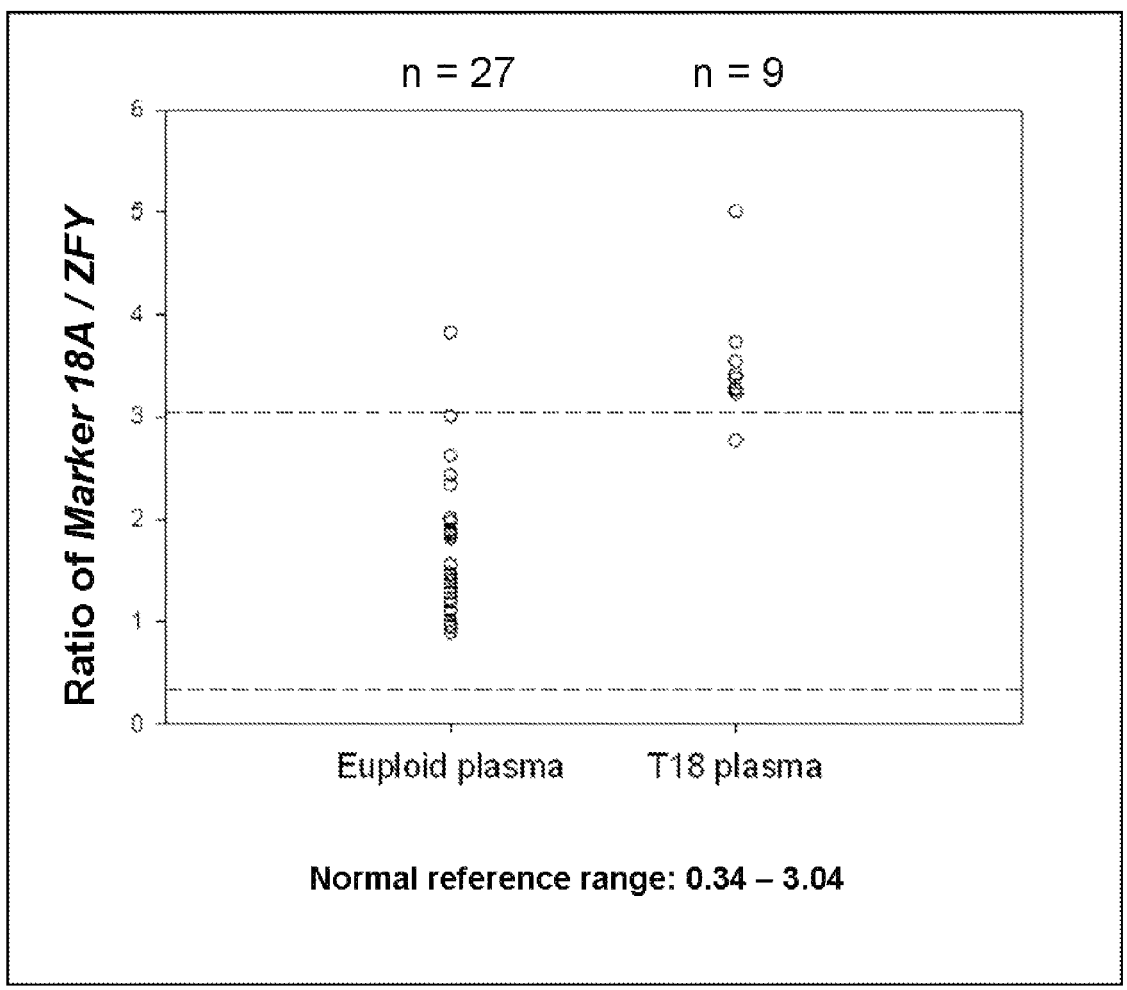
FIG. 16. Relative dosage of fetal chromosome 18 (Marker 18A) to chromosome Y (ZFY) in euploid (n=27) and trisomy 18 (T18) (n=9) maternal plasma samples. The normal reference range (mean±1.96SD) is depicted by the dotted lines.

To demonstrate that this approach is feasible to detect T18 noninvasively in maternal plasma, the inventors analyzed 27 maternal plasma samples obtained from pregnancies with euploid male fetuses and 9 from pregnancies with T18 male fetuses. Among the 27 euploid cases, 18, 4 and 9 cases were obtained from the first, second and third trimesters, respectively. All T18 cases were obtained from the first trimester. The median gestational age of the euploid and T18 groups were 14.1 and 13.3, respectively. The normal reference range was 0.34-3.04 (FIG. 16). Based on this reference range, 26 out of 27 euploid cases and 8 out of 9 T18 were correctly classified, giving a sensitivity of 88.9% and a specificity of 96.3%.

Beta-Actin as a Digestion Control

The enzyme digestion efficiency was evaluated by analyzing the enzyme-digested maternal plasma samples with the beta-actin assay that targeted at a region completely unmethylated in placentas and maternal blood cells while containing similar MSRE restriction sites as the Marker 18A amplicon (FIG. 17). Beta-actin sequences were not detectable in all the digested plasma samples.

III. Conclusion

This example illustrated that, using hypermethylated Marker 18A as the fetal epigenetic marker on chromosome 18 and ZFY as the fetal genetic marker on chromosome Y, the EGG approach can be applied to infer the relative dosage of fetal chromosome 18 from maternal plasma. It has also been demonstrated that, by comparing such relative chromosome dosage in euploid and T18 maternal plasma samples by the EGG approach, noninvasive prenatal detection of trisomy 18 is feasible. The noninvasive prenatal detection of trisomy 18 using this EGG approach could be extended to cover more fetuses in the general population by replacing the Y-specific fetal genetic marker, which was used in this example as an illustration, with other fetal genetic marker, such as paternally-inherited SNP on a reference chromosome, to specifically measure the dosage of the fetal reference chromosome in maternal plasma.

Example 4

Epigenetic-Genetic Chromosome Dosage Approach for the Detection of Fetal Trisomy 13

This example demonstrates the application of epigenetic-genetic (EGG) chromosome dosage approach for the detection of fetal trisomy 13 (T13). This EGG approach involved a fetal epigenetic marker located on chromosome 13 and a fetal genetic marker located on a reference chromosome, respectively. The fetal epigenetic marker is, preferably, Marker 13A [genomic location chr13:105941431-105941818, defined according to the Human Genome March 2006 Assembly (hg18)]. It is a 188-bp region located at the 3' end of the gene EFNB2 (ephrin-B2), as identified by an methylated DNA immunoprecipitation and tiling array analysis (described in U.S. Ser. No. 61/308,578). However, this fetal epigenetic marker can also be any cytosine-containing DNA genomic region located within 100 kb upstream or downstream of the above locus, i.e., chr13:105941431-105941818. Furthermore, this fetal epigenetic marker can also be any cytosine-containing DNA genomic region with different epigenetic signature (DNA methylation levels) that distinguishes the fetal from the maternal chromosome 13 in maternal plasma.

The fetal genetic marker in maternal plasma is, preferably, a region located in the zinc-finger Y-linked (ZFY) gene on chromosome Y. However, this fetal genetic marker can also be any genetic differences between the fetus and its mother, including single-nucleotide polymorphism (SNP) and insertion/deletion (indel) polymorphism.

Materials and Methods

Sample Collection

Samples were obtained from women attending the Department of Obstetrics and Gynaecology at the Prince of Wales Hospital, Hong Kong, or the Harris Birthright Research Centre for Fetal Medicine, at the King's College Hospital, London, UK. All of the pregnancies were recruited with informed consent. The study was approved by the respective institutional review boards.

Chorionic villus samples (CVS) were collected during conventional prenatal diagnosis sessions in the first and second trimesters of pregnancy. The chromosome status of each euploid and T13 case was confirmed by full karyotyping. Maternal peripheral blood samples (12 mL in EDTA tubes) were collected from all subjects. CVS from the UK were harvested, kept frozen and sent to Hong Kong in batches on dry ice.

In this study, 5 T13 cases (4 from the first trimester and 1 from the second trimester) and 10 euploid cases (all from the first trimester) were recruited.

Sample Processing

Peripheral blood samples were processed by a double centrifugation protocol as previously described (Chiu et al. Clin Chem 2001; 47:1607-13). The blood cell portion was recentrifuged at 2,500 g, and any residual plasma was removed. DNA from the peripheral blood cells was extracted with the blood and body fluid protocol of the QIAAMP® DNA Blood Mini Kit (Qiagen).

DNA from the CVS and placentas was extracted with the QIAAMP® DNA Mini Kit (Qiagen) according to the manufacturer's tissue protocol.

Analysis of Marker 13a Methylation Status in Placentas and Maternal Blood Cells

DNA Methylation Analysis by Cloning and Bisulfite Sequencing

The methylation status of Marker 13A were analyzed in six pairs of placental tissues and maternal blood cells by cloning and bisulfite sequencing. Extracted DNA was bisulfite converted using the EZ DNA METHYLATION™ Kit (ZymoResearch) according to the manufacturer's instructions. Bisulfite-converted DNA was subjected to PCR amplification with the forward primer '5-aggaagagagGGAGGATAGGAG-GAGGGAGTTATAGT-3' and reverse primer '5-cagtaatac-gactcactatagggagaaggctAAAAT-TACACACAATACACACCAAAAAAT-3' targeting Marker 13A region. This set of primers were designed for analysis by the EPITYPER™ assay, but was also applied in the PCR amplification of bisulfite-converted DNA for bisulfite sequencing analysis. The PCR conditions are summarized in Table 13A. The PCR product was subsequently TA-cloned into a plasmid vector with the PGEM T-EASY™ Cloning Kit (Promega) according to manufacturer's instructions. Cloning was done with *Escherichia coli* strain JM109 (Promega). The inserts from the clones were then amplified using T7 and SP6 promoter primers (Promega) according to the manufacturer's instructions (Reaction conditions are summarized under the sub-title colony PCR assays in Table 13A). The PCR product was then subjected to sequencing reaction with the BIG- DYE® Terminator Cycle Sequencing v1.1 kit (Applied Biosystems) according to the manufacturer's instructions (Reaction conditions are summarized under the sub-title sequencing reaction in Table 13A). DNA was then precipitated with ethanol and resuspended in 10 µL of Hi-Di formamide and sequenced on a 3100 DNA Analyzer (Applied Biosystems). The sequencing data were analyzed using the SeqScape v2.5 software (Applied Biosystems). The inventors ensured >99% bisulfite conversion of each clone by examining the conversion rate at non-CpG cytosine residues.

The MI at each CpG site was calculated by the number of methylated clones divided by the total number of clones for each sample, which was 8 in our experiments. The average MI of the two biological replicates was calculated for each CpG site. The methylated site frequency was given by the number of methylated clones across each sample over the total number of clones scored.

Analysis of Marker 13A Methylation Status in T13 and Euploid Placentas
DNA Methylation Analysis by the Epityper Assay The EPITYPER™ assay was performed with the standard MASSCLEAVE™ protocol (Sequenom) (Ehrich et al. *Proc Natl Acad Sci USA* 2005; 102:15785-90) (Details of the conditions for individual reactions involved in the protocol are summarized in Table 13B). Briefly, the bisulfite-converted DNA was subjected to PCR amplification with the forward primer '5-aggaagagagGGAGGATAGGAGGAGG-GAGTTATAGT-3' and reverse primer '5-cagtaatacgactcac-tatagggagaaggctAAAATTACACA-CAATACACACCAAAAAAT-3' targeting Marker 13A region. In this set of primer, a T7 promoter tag was added to the 3' end of the reverse primer, and a 10-base tag was added to the 5' end of the primer to equalize the melting temperature between the forward and reverse primers. Extracted DNA was subjected to bisulfite conversion with an EZ DNA METHYLATION™ Kit (ZymoResearch) according to the manufacturer's instruction and amplified with PCR. The PCR products were then in vitro transcribed as RNA using the T7 DNA polymerase and T7 RNA polymerase, and cleaved specifically at bases with A- or G-residues by RNase A. The cleavage reaction generated CpG-containing fragments, or CpG unit, whose sizes would be dependent on the methylation status of the CpG sites (i.e., CpG or TpG for methylated and unmethylated CpGs, respectively, after bisulfite conversion). The products were then cleaned up, and resolved with a matrix-assisted laser desorption/ionization time-of-flight (MALDI-TOF) mass spectrophotometer (MASSARRAY™ Analyzer Compact). The methylation index (MI) of each CpG unit were calculated by dividing the peak height of the methylated product by the sum of peak heights of both the methylated and unmethylated products.

EGG Chromosome Dosage Analysis

The inventors adopted the EGG approach to compare the relative dosage of the fetal epigenetic marker, Marker 13A on chromosome 13, and that of a fetal genetic marker, ZFY on chromosome Y, in placental tissues (CVS) obtained from euploid and T13 pregnancies.

Methylation-Sensitive Restriction Endonuclesae (MSRE) Digestion

Three types of MSRE, namely AccI, NlaIV and HpaII (FASTDIGEST® enzymes, Fermentas Life Sciences), were used to digest the placental DNA. For each sample, 50 ng of placental DNA were incubated with 2 FDU each of the above enzymes, in 1× FASTDIGEST® Buffer at 37° C. for 2 hours, followed by enzyme inactivation at 65° C. for 20 minutes.

Assay Design and Reaction Conditions for the Digital PCR Analysis

Two monoplex digital PCR assays were developed to amplify digestion-resistant Marker 13A and ZFY, respectively. The basis of the digital PCR analysis have been described previously (Lo et al. *Proc Natl Acad Sci USA* 2007; 104:13116-21; Tong et al. *Clin Chem* 2010; 56:90-8).

The reaction volume was 5 µL per well at a final concentration of 1× TAQMAN®aq0 Universal PCR Master Mix (Applied Biosystems) with the respective primers and probes concentrations for each target. For Marker 13A, the reaction involved 250 nM TAQMAN® probe Integrated DNA Technologies) and 900 nM of each of the forward and reverse primers (Integrated DNA Technologies). For ZFY, the reaction involved 100 nM TAQMAN® probe, and 300 nM of each of the forward and reverse primers (Integrated DNA Technologies). The probe for Marker 13A was labeled with the reporter FAM while that for ZFY was labeled with the reporter VIC (Table 14). The total number of digital PCR reactions for each target was 192.

The experiments were carried out on the 7900HT Sequence Detection System (Applied Biosystems). The reaction was initiated at 50° C. for 2 min and continued at 95° C. for 10 min, followed by 55 and 45 cycles of 95° C. for 15 s for Marker 13A and ZFY, respectively, and 60° C. for 1 min. The fluorescence data were collected by the "Absolute Quantification" application of SDS 2.3 software (Applied Biosystems).

Statistical Analysis

Statistical analyses were performed with the SigmaStat 3.0 software (SPSS).

II. Results

Marker 13A is a Potential Fetal Epigenetic Marker

Figure 18:
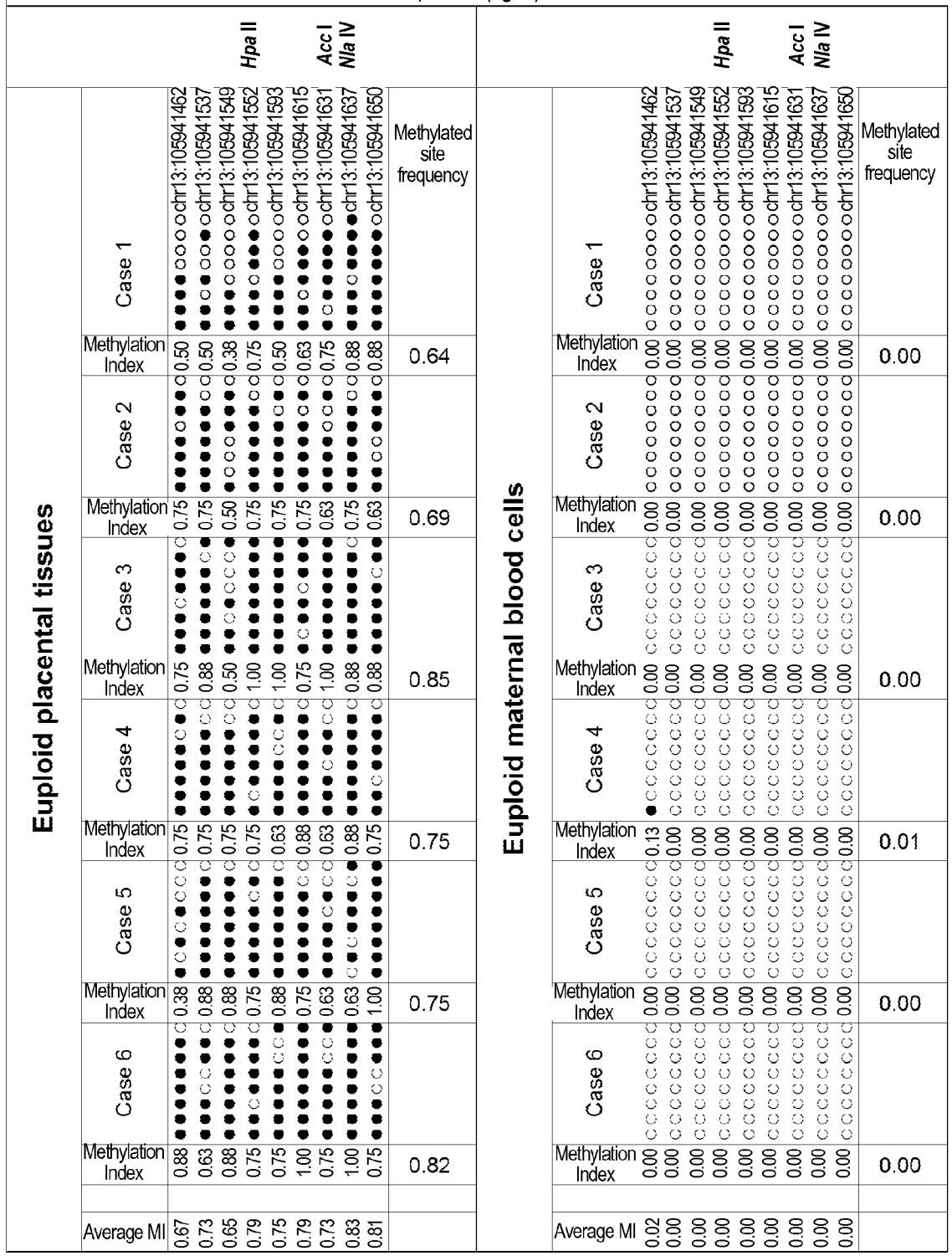
FIG. 18. DNA methylation levels of Marker 13A in euploid placentas (n=6) and maternal blood cells (n=6) analyzed by cloned bisulfite sequencing. All of the samples were obtained from the first trimester. A total of 8 clones were scored for each sample. The methylated sites are represented by a filled circle, while the unmethylated sites are represented by an empty circle. The methylation index (MI) at each CpG site was given by the number of methylated clones over the total number of clones at each CpG site. The methylated site frequency was given by the number of cloned methylated CpG sites over the total number of cloned CpG sites for each sample. The positions of the recognition sites of the methylation-sensitive restriction endonucleases are marked next to each genomic location of the CpG site. The genomic locations were mapped according to the Human Genome March 2006 Assembly (hg18) of the UCSC Genome Browser (genome.ucsc.edu).

Previous studies have shown that genomic region that is differentially methylated between placenta and maternal blood cells has the potential to be developed into fetal epigenetic markers in maternal plasma (Chim et al. *Clin Chem* 2008; 54:500-11; Tong et al. *Clin Chem* 2010; 56:90-8). Cloning and bisulfite sequencing results revealed that Marker 13A is predominantly methylated in euploid placentas (n=6) and essentially unmethylated in maternal blood cells (n=6) (FIG. 18). The average methylation indices in placentas and maternal blood cells are 0.78 and 0.00, respectively.

The inventors have also studied the methylation levels of Marker 13A in euploid (n=5) and T13 (n=5) placentas by the Epityper. Mann Whitney Rank Sum Test was performed to compare the MIs of the 5 euploid placentas with those of the 5 T13 placentas at each CpG unit (FIG. 19). It was reasoned that if the methylation level of Marker 13A does not change significantly between euploid and T18 placentas, it can be used to compare the dosage of fetal chromosome 13 in euploid and T18 fetal tissues or maternal plasma. It was found that within the target region of Marker 13A, 3 CpG units had no significant differential methylation between euploid and T13 placentas (FIG. 19). The inventors therefore design their subsequent digital PCR assays by targeting at these 3 CpG units.

EGG Chromosome-Dosage Analysis Using Placental DNA Samples

Figure 20:
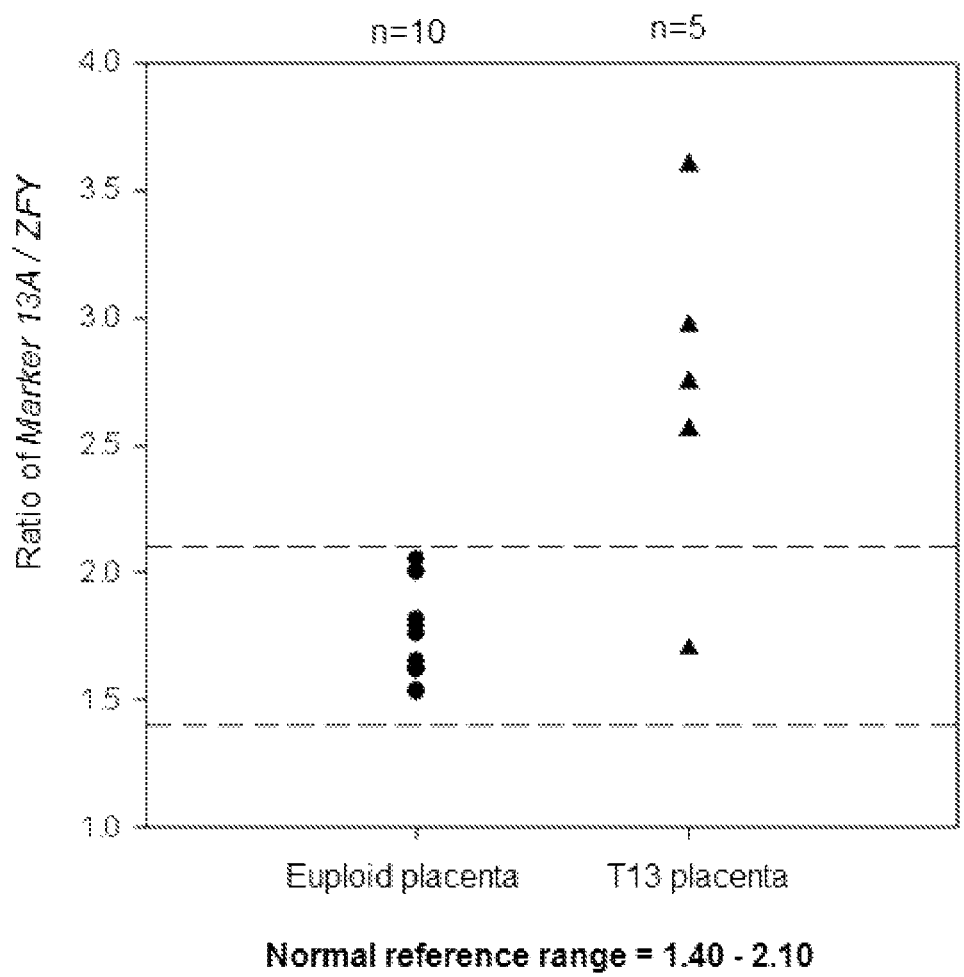
FIG. 20. Chromosome dosage comparison in euploid (n=10) and trisomy 13 (T13) (n=5) placental DNA samples by determining the ratio of digestion-resistant Marker 13A to ZFY. The normal reference range is depicted by dotted lines.

Placental DNA samples (5 for T13 and 10 for euploid) from pregnancies with male fetuses were analyzed with the respective monoplex digital PCR assays for Marker 13A and ZFY. The ratios of Marker 13A to ZFY in euploid and T13 samples were significantly different (Mann Whitney Rank Sum Test, P-value=0.023). A normal reference range, defined as the mean ratio of Marker 13A to ZFY±1.96SD, of the euploid samples was 1.40-2.10. All except one of the T13 cases had a ratio greater than the upper reference limit (FIG. 20).

III. Conclusion

This example illustrated that using hypermethylated Marker 13A as the fetal epigenetic marker on chromosome 13 and ZFY as the fetal genetic marker on chromosome Y, the EGG approach can be applied to infer the dosage of fetal chromosome 13 in placental tissues obtained during the first and second trimesters. It is feasible to detect trisomy 13 by comparing such relative chromosome dosage in euploid and T13 placental tissues. This approach has the potential to be applied to infer the relative chromosome dosage of fetal chromosome 13 in maternal plasma and to detect trisomy 13 in an noninvasive manner.

All patents, patent applications, and other publications, including GenBank Accession Numbers, cited in this application are incorporated by reference in the entirety for all purposes.

Sequence Listing

SEQ ID NO:1 dbSNP for rs6636 (taken from website ncbi.nlm.nih.gov/snp)

```
GAAGATTTTC CAAACTACTT TATGTCATTT AGCTTCTATT TTCTGAAGGG CTTTCTTTGG

TGCCATGTAC TCAGATCAGT CAGTTGACTG AAAGATGATC ATGTTTTCTT CGTAAAGATT

TAAGCAATTG GCAACTACAA AGACATTATT TTCTTACTGT TCTATATCAT GTACTGTTGC

TGACATTACA AAAGGGTCT GGAAGGGAAA CCGTGTCACT GTTTTATCTT TTTTCTTTAA

AATACAAAAG TATCCCAACT AATCATTTAT TATGGTCAGC TTGTTTTACA TGTCCCCTAT

[C/G]

ATGAGAAATG CTATCAACAT CTGTGATTTC TAAGAGTCTT ACCAAATTGT TACTTTAATT

CTTGTGTCCT GCTGAGTGGT TTTTCTTTTA AAATACCATT TTTATCACCC TGTGGCACTG

GGTGTGTTAC TGCGATTACA CTGATGATTC TGAGCTGTGC TTCTTCAAGT AGCTCAGTTC

TTGCGTTTTA TATTAGGTAA CAGTTTTGTG ATGCTTTTGT GCATTCTTTG TCATCTCTTC

TGAGTTTTCG AATCTGTCAT AAATAAACTT TTTCACTATG CACCTGGTAA CATCTGAGTT
```

SEQ ID NO:2 DNA sequence including 100 bp upstream and downstream of SNP rs6636 (taken from website genome.ucsc.edu/cgi-bin/hgGateway)

```
GGAAGGGAAACCGTGTCACTGTTTTATCTTTTTTCTTTAAAATACAAAAG

TATCCCAACTAATCATTTATTATGGTCAGCTTGTTTTACATGTCCCCTAT

[C/G]

ATGAGAAATGCTATCAACATCTGTGATTTCTAAGAGTCTTACCAAATTGT

TACTTTAATTCTTGTGTCCTGCTGAGTGGTTTTTCTTTTAAAATACCATT
```

TABLE 1

Oligonucleotide sequences and specific PCR conditions for the conventional real-time PCR and digital PCR assays.

| Assay | Oligonucleotide Sequence (5' to 3') | Specific Thermal Cycling Condition |
|---|---|---|
| Conventional | | |
| HLCS | Forward Primer CCGTGTGGCCAGAGGTG<br>Reverse Primer TGGGAGCCGGAACCTACC<br>TaqMan Probe FAM-TCCCGACCTGGCCCTTTGCC-TAMRA[a] | As described in specification |
| Digital and Conventional | | |
| HLCS | Forward Primer CCGTGTGGCCAGAGGTG<br>Reverse Primer AAAGGGCCAGGTCGGGA<br>TaqMan Probe FAM-AGGATTTGGGGCTGCGC(MGB)[b] | 50 cycles of 95° C. for 30 seconds and 60° C. for 1 minute |
| RASSF1A | Forward Primer AGCTGGCACCCGCTGG<br>Reverse Primer GTGTGGGGTTGCACGCG<br>TaqMan Probe VIC-ACCCGGCTGGAGCGT(MGB)[c] | 50 cycles of 95° C. for 30 seconds and 60° C. for 1 minute |
| ZFX/Y | Forward Primer CAAGTGCTGGACTCAGATGTAACTG<br>Reverse Primer TGAAGTAATGTCAGAAGCTAAAACATCA | 50 cycles of 95° C. for 15 seconds |

TABLE 1-continued

Oligonucleotide sequences and specific PCR conditions for the
conventional real-time PCR and digital PCR assays.

| Assay | Oligonucleotide Sequence (5' to 3') | Specific Thermal Cycling Condition |
|---|---|---|
| | TaqMan Probe_ZFY FAM-TCTTTACCACACTGCAC(MGB) | and 57° C. for 1 minute |
| | TaqMan Probe_ZFX VIC-TCTTTAGCACATTGCA(MGB) | |

[a]FAM = 6-carboxyfluorescein, TAMRA = 6-carboxytetramethylrhodamine.
[b]MGB = minor-groove binding.
[c]VIC = Applied Biosystems proprietary dye.

TABLE 2

The list of information regarding the 51 COBRA assays, including the names and locations of the loci, the primer sequences, reaction conditions and results.

| Gene Name | Common | Genebank | Sequence name | # of COBRA assay regions | (hg18) UCSC March 2006 | F-primer (5'-3') | R-primer (5'-3') | Conclusion |
|---|---|---|---|---|---|---|---|---|
| 212940_at | COL6A1 | BE350145 | COL6A1 | 1 | chr21: 46,245,627-46,246,005 | GTGTTGGATAGTTTAGAGAGTATTGGTTTGT | AAACCCACACCCAACACTCAAA | both placenta and buffy coat are methylated |
| 233741_at | FTCD | AL109817 | FTCD region A | 1 | chr21: 46,399,972-46,400,232 | AGGGTTATTYGTAGTGGTATAGGGAGGTT | CACCRACTTCTCATTAACCAACAAAA | both placenta and buffy coat are methylated |
| | | | FTCD region B | 2 | chr21: 46,384,245-46,384,408 | GTAATTTTTAGATGGAATAGAAAATTGTATTTTTT | TAATTCCCTAAACAAATCTTAACCAAAAA | both placenta and buffy coat are methylated |
| | | | FTCD region C | | chr21: 46,382,737-46,383,058 | TGGGGTGTAGTGTGTTTATTGTTTGTT | AAATCTCCCTACCTAACTCAACCCAA | both placenta and buffy coat are methylated |
| 202245_at | LSS | AW084510 | LSS | 1 | chr21: 46,438,736-46,439,010 | TTTGTAGGATTGTTTGTGTAGAGGTTTTT | TCCTCTCTACATTCACTCAACCCAAA | both placenta and buffy coat are methylated |
| 241233_x_at C21orf81 | C21orf81 | AI978581 | C21orf81 region A | 2 | chr21: 14,275,136-14,275,436 | GGTTAGGGGTAGTATTYGGTGGTATATTGT | CCRCCACAAACAATACAACAACTAATAA | both placenta and buffy coat are methylated |
| | | | C21orf81 region B | | chr21: 14,274,791-14,275,078 | GGAGTTGTYGGGGGTTAAGTTGTTT | TCCCCCAACCTACCCCCTA | both placenta and buffy coat are methylated |
| | | | C21orf81 region C | 2 | chr21: 14,274,285-14,274,628 | GGTTTTAGTAATATTAGTGGTTTATAAAGAAGGAGTT | RATCCACCACAACCTTCAACAA | placenta unmethylated and BC methylated |
| | | | C21orf81 region D | | chr21: 14,273,725-14,274,165 | AGGTGAAAAGGTGATAGGGAGTTGTT | CTCCACCAACTAACTCCAACCAAAA | both placenta and buffy coat are methylated |
| 232536_at | C21orf30 | AL117578 | C21orf30 region A | 2 | chr21: 44,703,686-44,703,950 | GGATGTATAGGTGAATGATTGGTGTTATTT | AAAACTAACTAACCCCACAAAACACAAA | both placenta and buffy coat are methylated |
| | | | C21orf30 region B | | chr21: 44,704,106-44,704,401 | GGGTTGTTTTAGTTTAGGGTTTGGTT | CAAACACCCACRATAAAAACTCCAATA | both placenta and buffy coat are methylated |

TABLE 2-continued

The list of information regarding the 51 COBRA assays, including the names and locations of the loci, the primer sequences, reaction conditions and results.

| Gene Name | Common | Genebank | Sequence name | # of COBRA assay regions | (hg18) UCSC March 2006 | F-primer (5'-3') | R-primer (5'-3') | Conclusion |
|---|---|---|---|---|---|---|---|---|
| 239602_at | C21orf87 | AI942340 | C21orf87 | 1 | chr21: 39,608,366-39,608,641 | AAAATTTTTTGT TTTGTTAGGTTTT TGATT | CCACAAATTATAA CTTACTCAAAATC AAACTAATAA | both placenta and buffy coat are unmethylated |
| 219482_at | C21orf18 | NM_017438 | C21orf18 | 1 | chr21: 36,373,495-36,373,905 | GGGTAGTATAAA GGTAGTATTAGG AATAGGGGTTT | ACTCATCCACCTT ATCTCAAAACAAC AATAA | both placenta and buffy coat are methylated |
| 238428_at | KCNJ15 | BG542347 | KCNJ15 | 1 | chr21: 38,549,762-38,550,032 | GTATTGTTTTTGG ATTAGTGTAGAG GGTTT | CAAAATTCCATCC TTAAAAAAACTT CTAATAA | both placenta and buffy coat are methylated |
| 230470_at | DSCR9 | AW510868 | DSCR9 region A | 2 | chr21: 37,514,418-37,514,645 | GTGAYGTAATAA TTTAAATTATGAA GAGGTAATAGAG TT | CCCCACCRTTCCA TCCCAAA | both placenta and buffy coat are methylated |
| | | | DSCR9 region B | | chr21: 37,515,197-37,515,378 | GYGTTAGGTTAT GTTGGGGTTGTAT TATT | ACAACCRAAAAAC ACCACCCTAA | both placenta and buffy coat are unmethylated |
| 236631_at | C21orf125 | AA522688 | C21orf125 region A | 2 | chr21: 43,693,742-43,694,068 | TTAATAGTATTAA GGGTAGGTGGGT TT | CTACTAACATAA AAATATTAATTCT TCCCTATCTA | both placenta and buffy coat are methylated |
| | | | C21orf125 region B | | chr21: 43,694,824-43,695,108 | GTATGGTTAGGT AGGAGGTGGGGTT | CAATACCAAATTA AAATAAATCCCCA AAA | both placenta and buffy coat are methylated |
| 237268_at | DSCAM | BE503065 | DSCAM region A | 2 | chr21: 40,647,219-40,647,485 | GGTTGGGTAGYG TGTGGAGTTGTT | RATAAAAACCAAC ACCACCTTTACAAA | both placenta and buffy coat are methylated |
| | | | DSCAM region B | | chr21: 40,647,173-40,647,485 | GGTTGGGTAGYG TGTGGAGTTGTT | AACTACAAAAAA ACATAAAAATTTA CTTAATAACAAAAA | both placenta and buffy coat are methylated |
| 233818_at | ZNF294 | AK023499 | ZNF294 region A | 2 | chr21: 29,286,993-29,287,264 | GGGTTTAATGTTT GGTTTTTTATTGG TT | CCCATAATCRCRA TTACAACTATACT CTAAA | both placenta and buffy coat are unmethylated |
| | | | ZNF294 region B | | chr21: 29,286,764-29,287,046 | AYGTGTTAATYG GGGTTTGAGTGTTT | CACRATTCCCAA TCTACTCAAAA | both placenta and buffy coat are unmethylated |

TABLE 2-continued

The list of information regarding the 51 COBRA assays, including the names and locations of the loci, the primer sequences, reaction conditions and results.

| Gene Name | Common | Genebank | # of COBRA assay regions | Sequence name | (hg18) UCSC March 2006 | F-primer (5'-3') | R-primer (5'-3') | Conclusion |
|---|---|---|---|---|---|---|---|---|
| 242913_at | CLIC6 | AW816405 | 1 | CLIC6 | chr21: 34,963,094-34,963,335 | GAGGGAGGAGGG GAAGATAAAATT | AACTCCTAAACT CTTCCTCCACTACT AA | both placenta and buffy coat are methylated |
| 236910_at | MRPL39 | AI809483 | 2 | MRPL39 region A | chr21: 25,901,919-25,902,230 | GGGGAYGTGTTT YGAGGTTTTATT ATT | CRCCCACCACRTA AACTCTACAAA | both placenta and buffy coat are unmethylated |
| | | | | MRPL39 region B | chr21: 25,901,414-25,901,657 | TGGAGGYGTTGG TTATGGGTTTT | TTCCCATAAATTA ATCCTCCCAAACT ATA | both placenta and buffy coat are unmethylated |
| 241726_at | HLCS | AI682088 | 3 | HLCS region A | chr21: 37,275,090-37,275,427 | GGAGTGTTAAAT TTGGTTATTTTTG TTTGTAT | CRCTACCCCTTCTCC ACTAACTACTCAAA | placenta methylated and buffy coat unmethylated |
| | | | | HLCS region B1 | chr21: 37,274,765-37,275,074 | AGGAGTTAGAYG TTTTAGTTYGTGT GGTT | CTAAACACCCRAA TCCCCCAAA | placenta methylated and buffy coat unmethylated |
| | | | | HLCS region B2 | chr21: 37,274,651-37,275,063 | GTTTTAGTTYGTG TGGTTAGAGGTG GT | CTAAAAAATAAAA AACAAAATCCAAA ACAAA | placenta methylated and buffy coat unmethylated |
| 231696_x_at | C21orf4 | AV648424 | 1 | C21orf4 region A | chr21: 33,744,397-33,744,764 | GTTTTTTATTTTT GAGATTTAGAAT TTGATTTATTT | AAAAATTTCACTT TCTCCCCCAAA | both placenta and buffy coat are methylated |
| | | | 2 | C21orf4 region B | chr21: 33,764,164-33,764,488 | TTAGTAGAGYG GGATTTTATTATG TTGGTT | AAAAAAAAAAA ATCAATATTTTTAA ATAACATAAAAA TA | both placenta and buffy coat are methylated |
| | | | | C21orf4 region C | chr21: 33,763,170-33,763,602 | TTTAGGTTGGAGT GTAGTGGTATAA TTTTGTAT | CCTTTCTTAAAACT TTACACACAACTT TACTTTAAA | both placenta and buffy coat are methylated |
| 232755_at | UBE2G2 | AL355686 | 2 | UBE2G2 region A | chr21: 45,020,136-45,020,445 | GGAAATGTYGTT TGTTAATAGATTT GTTGTT | CTCTTACCTATCA ATTATATTTTTAA CTTTTTATTATAAAA | both placenta and buffy coat are methylated |
| | | | | UBE2G2 region B | chr21: 45,019,358-45,019,633 | AGAGGTGGTTTA TGGATGGATT | CCAACCTATCCTTTA CACTATACCCAAAA | both placenta and buffy coat are methylated |

TABLE 2-continued

The list of information regarding the 51 COBRA assays, including the names and locations of the loci, the primer sequences, reaction conditions and results.

| Gene Name | Common | Genebank | # of COBRA assay regions | Sequence name | (hg18) UCSC March 2006 | F-primer (5'-3') | R-primer (5'-3') | Conclusion |
|---|---|---|---|---|---|---|---|---|
| 236061_at | PRDM15 | BF058757 | 2 | PRDM15 region A | chr21: 42,109,470-42,109,789 | GTATTATAATTTT TGATTTAGTTTTT ATGTTAGGGTT | CAAATACACTCAC TCCTACCAAAACC TAA | both placenta and buffy coat are methylated |
|  |  |  |  | PRDM15 region B | chr21: 42,109,068-42,109,280 | ATTYGTTGTGTTT TTGAAGGTATGA AGATT | ACCCACCTAACTT CCCTACCACATA | both placenta and buffy coat are methylated |
|  |  |  | 1 | PRDM15 region C | chr21: 42,095,814-42,096,235 | GTTTAGGGTAGT GTTGGGGTTGTTT | CTTCACCACCATA AAATCCACATATA CACTATA | both placenta and buffy coat are methylated |
|  |  |  | 1 | PRDM15 region D | chr21: 42,093,090-42,093,290 | AAGTAGAGAGGT TAGTTTATTAATA GAAGTATTAATT GTT | AAACTTCTCCCCA CACCCTCAATA | both placenta and buffy coat are methylated |
| 242784_at | ETS2 | AV646177 | 1 | ETS2 | chr21: 39,101,959-39,102,202 | GTAGTTATGTGG ATTTTGGGTAGAT TGTTT | CACATTCACTCAA AATCTCCACTTAA TAA | both placenta and buffy coat are methylated |
| 231245_s_at | C21orf80 | AW294061 | 1 | C21orf80 | chr21: 45,532,732-45,533,105 | TTYGGGGAATAG YGGGAGTTGTT | AATACTCTAAAACTAAAA | both placenta and buffy coat a little methylated |
| 234315_at | BACH1 | AF317902 | 1 | BACH1 | chr21: 29,644,841-29,645,100 | GAAGAATGGTTA TGTAGGGTAGAG GATAATT | AATTCRTAACTTTC ATAAAAATCTACT CCTCTTCTAA | both placenta and buffy coat are methylated |
| 239968_at | C21orf84 | AW206007 | 1 | C21orf84 | chr21: 43,722,837-43,723,075 | GTTAGGTTAGAT ATGTTGGGTAGTT AGGGTTT | CATATAACCCCTA ACCACCCCAAA | both placenta and buffy coat are methylated |
| 229639_s_at | SLC19A1 | AI858077 | 2 | SLC19A1 region A | chr21: 45,780,108-45,780,457 | TTTTAGTTTTTT GGTTGTAGGAGA GGTT | AATAAACAACCTTA TAATTCAACCCAA AAAA | both placenta and buffy coat are methylated |
|  |  |  |  | SLC19A1 region B | chr21: 45,780,660-45,780,989 | GTTATTGGGATA GTGGAGGTGTTG TT | ACACATAATACTC ACCCCTATAAATA ACCTTAA | both placenta and buffy coat are methylated |
|  |  |  | 1 | SLC19A1 region C | chr21: 45,786,589-45,786,920 | TYGTGGGTGGGA GGGTGTTT | CCCCACCACTCAC CTCACAAA | both placenta and buffy coat are unmethylated |
| 236988_x_at | ITGB2 | W68403 | 1 | ITGB2 region A | chr21: 45,155,727-45,156,027 | GTGTGTATTTGGA AATAAAAGGGTA GGATT | TACACTTCTACCCC AATATACCCCAAA | both placenta and buffy coat are methylated |
|  |  |  | 1 | ITGB2 region B | chr21: 45,154,850-45,155,200 | AGGGGAGTTTTA TGGGTGGTTAGTT | CACCACCCCCAAA TACAAAAAAA | both placenta and buffy coat are unmethylated |

TABLE 2-continued

The list of information regarding the 51 COBRA assays, including the names and locations of the loci, the primer sequences, reaction conditions and results.

| Gene Name | Common | Genebank | # of COBRA assay regions | Sequence name | (hg18) UCSC March 2006 | F-primer (5'-3') | R-primer (5'-3') | Conclusion |
|---|---|---|---|---|---|---|---|---|
| 240406_at | USP16 | AI022850 | 1 | USP16 region A | chr21: 29,318,793-29,319,027 | TGGGGTGGTGGT GGTTTAGTT | CTCCCAACRCAAA AAACCAAA | both placenta and buffy coat are unmethylated |
| | | | 2 | USP16 region B | chr21: 29,345,689-29,346,141 | AAGTGAGGATAT TATAAAGGATTTT AAAGATTTTT | TAATAAATAATCA TATACCTTATCAT AATCCTCAATATA | both placenta and buffy coat are methylated |
| | | | | USP16 region C | chr21: 29,346,422-29,346,772 | GTTTAGATTGTAT ATGGGAATTATA TTATGTTAGTTTTT | CTCCCACAATTCC CACATATCATAA | both placenta and buffy coat are methylated |
| 240809_at | C21orf121 | AI138282 | 1 | C21orf121 region A | chr21: 42,314,588-42,314,901 | GGGGTTATTTATT TGGTGATAGTGG TATATATT | ATCCCTACCCTATT ATTCCTCTTTTACA AA | both placenta and buffy coat are unmethylated |
| | | | 1 | C21orf121 region B | chr21: 42,302,126-42,302,508 | TTTTTATGAGAAAT TTTTTTAAAATGG ATTAATTT | CATCCCAACACAC CRCTAAAA | both placenta and buffy coat are methylated |

TABLE 3A

Detection of HLCS, RASSF1A, ZFY and ZFX in the mock- and BstUI-digested DNA samples.

|  | Copy number | | | |
| --- | --- | --- | --- | --- |
| Sample | HLCS | RASSF1A | ZFY | ZFX |
| Maternal blood 1_mock | 487 | 464 | 0 | 455 |
| Maternal blood 1_BstUI | 6 | 0 | 0 | 459 |
| Maternal blood 2_mock | 374 | 321 | 0 | 397 |
| Maternal blood 2_BstUI | 17 | 0 | 0 | 437 |
| Placenta 1_mock | 295 | 287 | 158 | 171 |
| Placenta 1_BstUI | 196 | 187 | 164 | 177 |
| Placenta 2_mock | 158 | 113 | 93 | 64 |
| Placenta 2_BstUI | 106 | 81 | 90 | 95 |

The copy numbers were corrected for the Poisson distribution using the formula in the text.

TABLE 3B

Detection of HLCS and RASSF1A in the untreated and BstUI-digested DNA samples.

|  |  | Copy number | |
| --- | --- | --- | --- |
| Replicate | Sample | HLCS | RASSF1A |
| 1 | Post-plasma 1_untreated | 172 | 109 |
| 1 | Post-plasma 1_BstUI | 9 | 1 |
| 2 | Post-plasma 1_BstUI | 6 | 0 |
| 1 | Post-plasma 2_untreated | 106 | 66 |
| 1 | Post-plasma 2_BstUI | 4 | 3 |
| 2 | Post-plasma 2_BstUI | 2 | 1 |

The copy numbers were corrected for the Poisson distribution using the formula in the text.

TABLE 4

Information on the samples used for the digital PCR analysis.
(A) Placental tissue samples, (B) Maternal plasma samples.

(A)

| Trimester | Euploid sample | Number of panel | Copy number | | | | HLCS/ RASSF1A | HLCS/ ZFY |
| --- | --- | --- | --- | --- | --- | --- | --- | --- |
|  |  |  | HLCS | RASSF1A | ZFY | ZFX |  |  |
| 3rd | N2541 | 4 | 1187 | 1165 | 994 | 1007 | 1.02 | 1.19 |
| 3rd | N2550 | 4 | 890 | 731 | 685 | 587 | 1.22 | 1.30 |
| 3rd | N2552 | 4 | 1156 | 829 | 808 | 703 | 1.40 | 1.43 |
| 3rd | N2559K | 4 | 957 | 712 | 673 | 670 | 1.35 | 1.42 |
| 3rd | N2582 | 4 | 934 | 781 | 623 | 569 | 1.20 | 1.50 |
| 1st | V2863 | 4 | 714 | 752 | 647 | 581 | 0.95 | 1.10 |
| 1st | V2894 | 4 | 625 | 604 | 481 | 469 | 1.03 | 1.30 |
| 1st | V2951 | 4 | 799 | 611 | 609 | 655 | 1.31 | 1.31 |
| 1st | V3031 | 4 | 1007 | 658 | 709 | 650 | 1.53 | 1.42 |
| 1st | V3104 | 4 | 1059 | 729 | 683 | 665 | 1.45 | 1.55 |

| Trimester | T21 sample | Number of panel | Copy number | | | | HLCS/ RASSF1A | HLCS/ ZFY |
| --- | --- | --- | --- | --- | --- | --- | --- | --- |
|  |  |  | HLCS | RASSF1A | ZFY | ZFX |  |  |
| 2nd | N0349 | 4 | 2028 | 1031 | 1022 | 876 | 1.97 | 1.98 |
| 2nd | N0435K | 4 | 899 | 538 | 448 | 424 | 1.67 | 2.01 |
| 2nd | N0764L | 4 | 990 | 747 | 576 | 571 | 1.33 | 1.72 |
| 2nd | N1519K | 4 | 891 | 507 | 424 | 356 | 1.76 | 2.10 |
| 2nd | N2770K | 4 | 868 | 592 | 517 | 511 | 1.47 | 1.68 |
| 2nd | N3285K | 4 | 1004 | 605 | 469 | 410 | 1.66 | 2.14 |
| 1st | N0234L | 4 | 964 | 764 | 558 | 513 | 1.26 | 1.73 |
| 1st | N0456E | 4 | 717 | 459 | 316 | 308 | 1.56 | 2.27 |
| 1st | N0891L | 4 | 955 | 655 | 520 | 491 | 1.46 | 1.84 |
| 1st | N2849K | 4 | 848 | 562 | 423 | 600 | 1.51 | 2.01 |
| 1st | N3168K | 4 | 825 | 625 | 444 | 406 | 1.32 | 1.86 |
| 1st | N3228K | 4 | 1126 | 761 | 519 | 475 | 1.48 | 2.17 |

(B)

| Trimester | Euploid sample | Plasma vol. | Number of panel | Copy number | | | HLCS/ ZFY |
| --- | --- | --- | --- | --- | --- | --- | --- |
|  |  |  |  | HLCS | ZFY | ZFX |  |
| 3rd | M3885 | 4 mL | 6 | 296 | 147 | 1086 | 2.01 |
| 3rd | M3915 | 3.4 mL | 6 | 820 | 352 | 3941 | 2.33 |
| 3rd | M3936 | 3.8 mL | 6 | 694 | 283 | 3951 | 2.46 |
| 3rd | M4028 | 4.8 mL | 6 | 2123 | 869 | 5679 | 2.44 |
| 3rd | M4029 | 4.8 mL | 6 | 342 | 146 | 1259 | 2.34 |
| 3rd | M4039 | 4 mL | 6 | 752 | 378 | 3380 | 1.99 |
| 3rd | M4055 | 4 mL | 6 | 475 | 285 | 2612 | 1.67 |
| 3rd | M4060 | 3.6 mL | 6 | 681 | 383 | 3882 | 1.78 |
| 2nd | M3364 | 4.4 mL | 12 | 134 | 58 | 1782 | 2.30 |
| 2nd | M3367 | 4.6 mL | 12 | 182 | 107 | 958 | 1.71 |
| 2nd | M3377 | 4.8 mL | 12 | 208 | 76 | 1830 | 2.73 |
| 2nd | M3414 | 5.1 mL | 12 | 144 | 83 | 979 | 1.73 |
| 2nd | M4046 | 5.5 mL | 12 | 152 | 58 | 1633 | 2.62 |
| 2nd | M4048 | 5.8 mL | 12 | 114 | 52 | 1392 | 2.18 |

TABLE 4-continued

Information on the samples used for the digital PCR analysis.
(A) Placental tissue samples, (B) Maternal plasma samples.

| | | | | | | | |
|---|---|---|---|---|---|---|---|
| 2nd | M4096 | 6 mL | 12 | 260 | 85 | 2308 | 3.04 |
| 2nd | M4103 | 6 mL | 12 | 179 | 86 | 1608 | 2.07 |
| 1st | M4049 | 5.2 mL | 12 | 105 | 54 | 1419 | 1.93 |
| 1st | M4050 | 5.8 mL | 12 | 146 | 75 | 1054 | 1.94 |
| 1st | M4095 | 5.2 mL | 12 | 124 | 62 | 1332 | 1.99 |
| 1st | M4232 | 6.6 mL | 12 | 145 | 64 | 964 | 2.26 |
| 1st | M4265 | 6.1 mL | 12 | 111 | 63 | 1685 | 1.75 |
| 1st | M4266 | 6.2 mL | 12 | 1556 | 626 | 9078 | 2.49 |
| 1st | M4541 | 8.8 mL | 18 | 282 | 121 | 2911 | 2.34 |
| 1st | M4621 | 9.1 mL | 12 | 287 | 121 | 2062 | 2.38 |

| Trimester | T21 sample | Plasma vol. | Number of panel | Copy number HLCS | Copy number ZFY | Copy number ZFX | HLCS/ZFY |
|---|---|---|---|---|---|---|---|
| 2nd | M2770 | 7.4 mL | 12 | 731 | 248 | 3504 | 2.95 |
| 2nd | M3870 | 6.6 mL | 12 | 370 | 95 | 1541 | 3.88 |
| 2nd | M4183 | 8.8 mL | 18 | 695 | 231 | 2520 | 3.01 |
| 1st | M2948 | 6 mL | 12 | 705 | 224 | 5322 | 3.15 |
| 1st | M4101 | 6.4 mL | 12 | 630 | 162 | 3368 | 3.88 |

The number of copy of each locus and the ratios of HLCS to RASSF1A and HLCS to ZFY are shown. The copy numbers were corrected for the Poisson distribution using the formula in the text.

TABLE 5

Oligonucleotide sequences for the HLCS, TMED8-C/G SNP and beta-actin assays.

| Assay | Oligonucleotide | Sequences (5' to 3')(SEQ ID NO:) | PCR amplicon length (bp) |
|---|---|---|---|
| HLCS | Forward primer | CCGTGTGGCCAGAGGTG (123) | 96 |
| | Reverse primer | AAAGGGCCAGGTCGGGA (124) | |
| | TaqMan probe (FAM) | FAM-AGGATTTGGGGCTGCGC (MGB)[a] (125) | |
| | TaqMan probe (VIC) | VIC-AGGATTTGGGGCTGCGC (MGB)[b] (126) | |
| TMED8-C/G | Forward primer | TGGTAAGACTCTTAGAAATCACAGATGTT (127) | 96 |
| | Reverse primer | GTATCCCAACTAATCATTTATTATGGTCA (128) | |
| | TaqMan probe_TMED8-C | FAM-CCCCTATCATGAGAAAT (MGB) (129) | |
| | TaqMan probe_TMED8-G | VIC-CCCCTATGATGAGAAAT (MGB) (130) | |
| Beta-actin | Forward primer | CCACCACCGCCGAGAC (131) | 96 |
| | Reverse primer | TGGCCGGGCTTACCTGG (132) | |
| | TaqMan probe | FAM-AGCACAGAGCCTCGCC (MGB) (133) | |

[a]FAM = 6-carboxyfluorescein, MGB = minor-groove binding.
[b]VIC = Applied Biosystems ® proprietary dye.

TABLE 6

Ratio of HLCS to TMED8-C allele in (A) mock-digested placental DNA, and (B) BstUI-digested placental DNA samples.

| Sample type | Sample | Fetal genotype | Maternal genotype | Copies per reaction HLCS | Copies per reaction TMED8-C | HLCS/ TMED8-C |
|---|---|---|---|---|---|---|
| (A) | | | | | | |
| 1T.euploid | V0057 | CG | GG | 2050 | 857 | 2.39 |
| 1T.euploid | V0360 | CG | GG | 866 | 343 | 2.52 |
| 1T.euploid | V3104 | CG | GG | 1877 | 794 | 2.36 |
| 3T.euploid | PLN74 | CG | GG | 3110 | 1502 | 2.07 |
| 3T.euploid | N0425 | CG | GG | 5695 | 2786 | 2.04 |
| 3T.euploid | N0426 | CG | GG | 4117 | 2103 | 1.96 |
| 1T.T21 | N0456 | CG | GG | 1574 | 489 | 3.22 |
| 1T.T21 | N0891 | CG | GG | 2011 | 621 | 3.24 |

TABLE 6-continued

Ratio of HLCS to TMED8-C allele in (A) mock-digested placental DNA, and (B) BstUI-digested placental DNA samples.

| Sample type | Sample | Fetal genotype | Maternal genotype | Copies per reaction HLCS | TMED8-C | HLCS/ TMED8-C |
|---|---|---|---|---|---|---|
| 1T.T21 | N3634 | CG | GG | 3867 | 1193 | 3.24 |
| 2T.T21 | N1519 | CG | GG | 2030 | 606 | 3.35 |
| 3T.euploid | N2541 | GG |  | 4226 | 0 | N/A |

(B)

| Sample type | Sample | Fetal genotype | Maternal genotype | HLCS | TMED8-C | HLCS/ TMED8-C |
|---|---|---|---|---|---|---|
| 1T.euploid | V0057 | CG | GG | 1927 | 1001 | 1.92 |
| 1T.euploid | V0360 | CG | GG | 887 | 489 | 1.82 |
| 1T.euploid | V3104 | CG | GG | 1909 | 1035 | 1.84 |
| 3T.euploid | PLN74 | CG | GG | 3076 | 1504 | 2.05 |
| 3T.euploid | N0425 | CG | GG | 4364 | 2896 | 1.51 |
| 3T.euploid | N0426 | CG | GG | 3653 | 2669 | 1.37 |
| 1T.T21 | N0456 | CG | GG | 1866 | 671 | 2.78 |
| 1T.T21 | N0891 | CG | GG | 2350 | 955 | 2.46 |
| 1T.T21 | N3634 | CG | GG | 4084 | 1493 | 2.73 |
| 2T.T21 | N1519 | CG | GG | 3141 | 1001 | 3.14 |
| 3T.euploid | N2541 | GG |  | 4402 | 0 | N/A |

1T, first trimester; 2T, second trimester; 3T, third trimester.

TABLE 7

Ratio of HLCS to TMED8-G allele in (A) mock-digested placental DNA, and (B) BstUI-digested placental DNA samples.

| Sample type | Sample | Fetal genotype | Maternal genotype | Copies per reaction HLCS | TMED8-G | HLCS/ TMED8-G |
|---|---|---|---|---|---|---|

(A)

| Sample type | Sample | Fetal genotype | Maternal genotype | HLCS | TMED8-G | HLCS/ TMED8-G |
|---|---|---|---|---|---|---|
| 1T.euploid | V0207 | CG | CC | 230 | 66 | 3.50 |
| 1T.euploid | V0208 | CG | CC | 220 | 98 | 2.25 |
| 1T.euploid | V0284 | CG | CC | 966 | 474 | 2.04 |
| 1T.euploid | V0488 | CG | CC | 498 | 226 | 2.20 |
| 1T.euploid | V0492 | CG | CC | 570 | 322 | 1.77 |
| 1T.euploid | V0503 | CG | CC | 1095 | 569 | 1.92 |
| 1T.euploid | V0580 | CG | CC | 892 | 397 | 2.25 |
| 1T.euploid | V3031 | CG | CC | 1993 | 925 | 2.15 |
| 3T.euploid | N0069 | CG | CC | 4858 | 2416 | 2.01 |
| 3T.euploid | PLN113 | CG | CC | 2136 | 886 | 2.41 |
| 3T.euploid | PLN114 | CG | CC | 3973 | 1909 | 2.08 |
| 3T.euploid | N0333 | CG | CC | 3144 | 1301 | 2.42 |
| 3T.euploid | N0524 | CG | CC | 5213 | 2817 | 1.85 |
| 3T.euploid | N0527 | CG | CC | 5376 | 2840 | 1.89 |
| 1T.T21 | N3228 | CG | CC | 6787 | 2239 | 3.03 |
| 1T.T21 | N3438 | CG | CC | 4349 | 1236 | 3.52 |
| 1T.T21 | N4101 | CG | CC | 5787 | 1902 | 3.04 |
| 2T.T21 | N2913 | CG | CC | 4907 | 1027 | 4.78 |
| 2T.T21 | N4183 | CG | CC | 4673 | 1651 | 2.83 |
| 3T.euploid | N2582 | CC |  | 2177 | 0 | N/A |

(B)

| 1T.euploid | V0207 | CG | CC | 246 | 163 | 1.52 |
|---|---|---|---|---|---|---|
| 1T.euploid | V0208 | CG | CC | 262 | 172 | 1.52 |
| 1T.euploid | V0284 | CG | CC | 443 | 463 | 0.96 |
| 1T.euploid | V0488 | CG | CC | 469 | 333 | 1.41 |
| 1T.euploid | V0492 | CG | CC | 501 | 308 | 1.63 |
| 1T.euploid | V0503 | CG | CC | 1144 | 755 | 1.52 |
| 1T.euploid | V0580 | CG | CC | 615 | 503 | 1.22 |
| 1T.euploid | V3031 | CG | CC | 2249 | 1290 | 1.74 |
| 3T.euploid | N0069 | CG | CC | 3389 | 2446 | 1.39 |
| 3T.euploid | PLN113 | CG | CC | 2001 | 969 | 2.07 |
| 3T.euploid | PLN114 | CG | CC | 2751 | 2019 | 1.36 |
| 3T.euploid | N0333 | CG | CC | 2499 | 1613 | 1.55 |
| 3T.euploid | N0524 | CG | CC | 3579 | 2834 | 1.26 |
| 3T.euploid | N0527 | CG | CC | 3250 | 3049 | 1.07 |
| 1T.T21 | N3228 | CG | CC | 5448 | 2753 | 1.98 |
| 1T.T21 | N3438 | CG | CC | 5733 | 2272 | 2.52 |
| 1T.T21 | N4101 | CG | CC | 4610 | 2272 | 2.03 |
| 2T.T21 | N2913 | CG | CC | 4057 | 1991 | 2.04 |

TABLE 7-continued

Ratio of HLCS to TMED8-G allele in (A) mock-digested placental DNA, and (B) BstUI-digested placental DNA samples.

| Sample type | Sample | Fetal genotype | Maternal genotype | Copies per reaction HLCS | Copies per reaction TMED8-G | HLCS/TMED8-G |
|---|---|---|---|---|---|---|
| 2T.T21 | N4183 | CG | CC | 4517 | 1196 | 3.78 |
| 3T.euploid | N2582 | CC |  | 1439 | 0 | N/A |

1T, first trimester; 2T, second trimester; 3T, third trimester.

TABLE 8

Digestion efficiency evaluated by beta-actin real-time qPCR analysis.

| Sample type | Sample | Copies per reaction Mock | Copies per reaction BstUI | % digested |
|---|---|---|---|---|
| (A) | | | | |
| 1T.euploid | V0057 | 1845 | 5 | 99.7 |
| 1T.euploid | V0360 | 856 | 6 | 99.3 |
| 1T.euploid | V3104 | 1852 | 8 | 99.5 |
| 3T.euploid | PLN74 | 2937 | 5 | 99.8 |
| 3T.euploid | N0425 | 4845 | 24 | 99.5 |
| 3T.euploid | N0426 | 4283 | 33 | 99.2 |
| 1T.T21 | N0456 | 1022 | 3 | 99.7 |
| 1T.T21 | N0891 | 1315 | 13 | 99.0 |
| 1T.T21 | N3634 | 2275 | 15 | 99.3 |
| 2T.T21 | N1519 | 1607 | 28 | 98.3 |
| 3T.euploid | N2541 | 3974 | 58 | 98.5 |
| (B) | | | | |
| 1T.euploid | V0207 | 131 | 1 | 98.9 |
| 1T.euploid | V0208 | 200 | 7 | 96.8 |
| 1T.euploid | V0284 | 856 | 2 | 99.8 |
| 1T.euploid | V0488 | 220 | 2 | 99.3 |
| 1T.euploid | V0492 | 560 | 7 | 98.8 |
| 1T.euploid | V0503 | 1036 | 2 | 99.8 |
| 1T.euploid | V0580 | 837 | 7 | 99.2 |
| 1T.euploid | V3031 | 2154 | 13 | 99.4 |
| 3T.euploid | N0069 | 4977 | 17 | 99.7 |
| 3T.euploid | PLN113 | 1873 | 31 | 98.3 |
| 3T.euploid | PLN114 | 3569 | 15 | 99.6 |
| 3T.euploid | N0333 | 2982 | 10 | 99.7 |
| 3T.euploid | N0524 | 5583 | 18 | 99.7 |
| 3T.euploid | N0527 | 5667 | 14 | 99.8 |
| 1T.T21 | N3228 | 3649 | 26 | 99.3 |
| 1T.T21 | N3438 | 3136 | 20 | 99.4 |
| 1T.T21 | N4101 | 2748 | 16 | 99.4 |
| 2T.T21 | N2913 | 2822 | 19 | 99.3 |
| 2T.T21 | N4183 | 3544 | 9 | 99.7 |
| 3T.euploid | N2582 | 2341 | 12 | 99.5 |

(A) Samples for HLCS to TMED8-C ratio analysis.
(B) Samples for HLCS to TMED8-G ratio analysis.
1T, first trimester; 2T, second trimester; 3T, third trimester.

TABLE 9

Specificity of the TMED8-C/G SNP assays. Genotypes of the placentas are indicated after the sample number. The copy numbers were corrected for Poisson distribution.

(A)

| Sample | Copies HLCS | Copies TMED8-C | No. of PCR wells analyzed |
|---|---|---|---|
| Placenta1_CG | 41 | 29 | 192 |
| Placenta2_CG | 95 | 46 | 192 |
| Placenta3_CC | 76 | 87 | 192 |
| Placenta4_CC | 28 | 20 | 192 |
| Placenta5_GG | 39 | 0 | 192 |
| Placenta6_GG | 13 | 0 | 192 |

(B)

| Sample | Copies HLCS | Copies TMED8-G | No. of PCR wells analyzed |
|---|---|---|---|
| Placenta1_CG | 82 | 37 | 192 |
| Placenta2_CG | 76 | 40 | 192 |
| Placenta3_CC | 192 | 0 | 384 |
| Placenta4_CC | 83 | 0 | 384 |
| Placenta5_GG | 51 | 53 | 192 |
| Placenta6_GG | 45 | 47 | 192 |

(A) HLCS and TMED8-C duplex assay.
(B) HLCS and TMED8-G duplex assay.

TABLE 10

Primer sequences for the PCR amplification of bisulfite-converted DNA involved in the analysis by the Epityper and bisulfite sequencing for Marker 18A and beta-actin.

| Target | Assays | Directions | Sequences (5' to 3') (SEQ ID NO:) |
|---|---|---|---|
| Marker 18A | Bisulfite sequencing | Forward | 5'-aggaagagagGGTTATTTGGGGGTAGTAGG-3' (134) |
| | | Reverse | 5'-cagtaatacgactcactatagggagaaggctAAACTCAAAACTAAAACAAACACTC-3' (135) |
| Marker 18A | Epityper | Forward | 5'-aggaagagagGGTTATTTGGGGGTAGTAGG-3' (136) |
| | | Reverse | 5'-cagtaatacgactcactatagggagaaggctAAACTCAAAACTAAAACAAACACTC-3' (137) |

TABLE 10-continued

Primer sequences for the PCR amplification of bisulfite-converted DNA involved in the analysis by the Epityper and bisulfite sequencing for Marker 18A and beta-actin.

| Target | Assays | Directions | Sequences (5' to 3')(SEQ ID NO:) |
|---|---|---|---|
| Beta-actin | Bisulfite sequencing | Forward | 5'-TTTATTTTGYGATTTTTATTGGTAAGAGTT-3'(138) |
|  |  | Reverse | 5'-AACACAAAACCTCRCCTTTACC-3'(139) |

TABLE 11A

Reaction conditions for bisulfite sequencing analysis.

|  | Final concentration | Thermal profile |  |  |
|---|---|---|---|---|
| Bisulfite PCR reaction conditions | | | | |
| 10X buffer II | 1X | | | |
| MgCl$_2$ | 3 mM | | | |
| dNTP | 200 μM | 95° C. | 10 min | |
| Forward primer | 200 nM | 95° C. | 40 s | |
| Reverse primer | 200 nM | Specific annealing temperature | 45 s | ] 40 cycles |
| AmpliTaq Gold | 1 U | 72° C. | 45 s | |
| Bisulfite-converted DNA | 50 ng | 72° C. | 7 min | |
| Total reaction volume | 25 μL | | | |
| Colony PCR assays | | | | |
| 10X buffer II | 1X | 95° C. | 10 min | |
| MgCl$_2$ | 4 mM | 95° C. | 1 min | |
| dNTP | 200 μM | 55° C.-0.5° C. per cycle | 1.5 min | ] 10 cycles |
| SP6/T7 primers | Each 100 nM | 72° C. | 1 min | |
| AmpliTaq Gold | 1 U | 95° C. | 1 min | |
| Template DNA | Colony | 50° C. | 1.5 min | ] 18 cycles |
| Total reaction volume | 25 μL | 72° C. | 1 min | |
|  |  | 72° C. | 7 min | |
| Sequencing reaction | | | | |
| Big Dye v. 3.1 | 2.5X | 96° C. | 10 s | |
| 5x BigDye sequencing buffer | 1X | 50° C. | 5 s | ] 25 cycles |
| Primer (SP6) | 250 nM | 60° C. | 4 min | |
| Water | variable | | | |
| Product from colony PCR reaction | 1.5 μL | | | |
| Total reaction volume | 10 μL | | | |

TABLE 11B

Reaction conditions for the Epityper analysis.
Epityper assay

| PCR amplification | | | | |
|---|---|---|---|---|
|  | Final concentration | Thermal profile | | |
| 10X Hot Star Buffer | 1X | | | |
| dNTP | 200 μM | 94° C. | 15 min | |
| Forward primer | 200 nM | 94° C. | 20 s | |
| Reverse primer | 200 nM | Specific annealing temperature | 30 s | ] 45 cycles |
| Hot Star Taq | 0.2 unit | 72° C. | 1 min | |
| Bisulfite-converted DNA | 50 ng | | | |
| Total reaction volume | 5 μL | 72° C. | 3 min | |
| Dephosphorylation | | | | |
|  | Volume per reaction | Thermal profile | | |
| RNase-free water | 1.7 μL | 37° C. | 40 min | |
| Shrimp alkaline phosphatase (SAP) | 0.3 μL | 85° C. | 5 min | |
| Total reaction volume | 2 μL | | | |
| This mixture is added to the product of the PCR amplification | | | | |

TABLE 11B-continued

Reaction conditions for the Epityper analysis.
Epityper assay

In vitro transcription and Rnase A cleavage

|  | Final concentration | Thermal profile | |
|---|---|---|---|
| RNase-free water | variable | 37° C. | 3 hours |
| 5X T7 Polymerase Buffer | 0.64X | | |
| T-cleavage mix (or C-cleavage) | 0.24 μL | | |
| DTT | 3.14 mM | | |
| T7 RNA & DNA Polymerase | 22 units | | |
| RNaseA | 0.09 mg/mL | | |
| SAP-treated PCR product | 2 μL | | |
| Total reaction volume | 5 μL | | |

Sample conditioning

Add 20 μL water and 6 mg Clean Resin to each well in a 384-well setting. Rotate for 10 minutes and spin down for 5 minutes at 3,200 g. The samples are then ready to be dispensed onto the SpectroCHIP ® bioarray.

20

TABLE 12

Oligonucleotide sequences for the Marker 18A, ZFY, and beta-actin qPCR/digital PCR assays.

| Assay | Oligonucleotide | Sequences (5' to 3')(SEQ ID NO:) | PCR amplicon length (bp) |
|---|---|---|---|
| Marker 18A | Forward primer | 5'-AGGCCTGCGCAGGTGG-3' (140) | 83 bp |
|  | Reverse primer | 5'-CACTCGCTGAGCGTCCCC-3' (141) | |
|  | TaqMan probe (FAM) | 5'-FAM-CGCCCCGCACAGCGCTCG-BHQ1-3' (142) | |
| ZFY | Forward primer | 5'-CAAGTGCTGGACTCAGATGTAACTG-3' (143) | 87 bp |
|  | Reverse primer | 5'-TGAAGTAATGTCAGAAGCTAAAACATCA-3' (144) | |
|  | TaqMan probe (VIC) | 5'-VIC-TCTTTACCACACTGCAC-MGB-3' (145) | |
| Beta-actin | Forward primer | 5'-CCCCCATCTCCGGAGGC-3' (146) | 88 bp |
|  | Reverse primer | 5'-GTCTGGGCCGCAGCGG-3' (147) | |
|  | TaqMan probe (VIC) | 5'-VIC-AGGGGCTTCTCCCGCGC-MGB-3' (148) | |

NOTE:
FAM is 6-carboxyfluorescein,
VIC is Applied Biosystems ® proprietary dye,
BHQ1 is Black-hole quencher 1, and
MGB is minor groove binding.

TABLE 13A

Reaction conditions for bisulfite sequencing analysis.

|  | Final concentration | Thermal profile | | |
|---|---|---|---|---|
| Bisulfite PCR reaction conditions | | | | |
| 10X buffer II | 1X | | | |
| MgCl$_2$ | 3 mM | | | |
| dNTP | 200 μM | 95° C. | 10 min | |
| Forward primer | 200 nM | 95° C. | 40 s | |
| Reverse primer | 200 nM | Specific annealing temperature | 45 s | 40 cycles |
| AmpliTaq Gold | 1 U | 72° C. | 45 s | |
| Bisulfite-converted DNA | 50 ng | 72° C. | 7 min | |
| Total reaction volume | 25 μL | | | |
| Colony PCR assays | | | | |
| 10X buffer II | 1X | 95° C. | 10 min | |
| MgCl$_2$ | 4 mM | 95° C. | 1 min | |
| dNTP | 200 μM | 55° C.-0.5° C. per cycle | 1.5 min | 10 cycles |
| SP6/T7 primers | Each 100 nM | 72° C. | 1 min | |
| AmpliTaq Gold | 1 U | 95° C. | 1 min | |
| Template DNA | Colony | 50° C. | 1.5 min | 18 cycles |

TABLE 13A-continued

Reaction conditions for bisulfite sequencing analysis.

| | Final concentration | Thermal profile | |
|---|---|---|---|
| Total reaction volume | 25 µL | 72° C. | 1 min |
| | | 72° C. | 7 min |

Sequencing reaction

| | Final concentration | Thermal profile | | |
|---|---|---|---|---|
| Big Dye v. 3.1 | 2.5X | 96° C. | 10 s | |
| 5x BigDye sequencing buffer | 1X | 50° C. | 5 s | 25 cycles |
| Primer (SP6) | 250 nM | 60° C. | 4 min | |
| Water | variable | | | |
| Product from colony PCR reaction | 1.5 µL | | | |
| Total reaction volume | 10 µL | | | |

15

TABLE 13B

Reaction conditions for the Epityper analysis.
Epityper assay

PCR amplification

| | Final concentration | Thermal profile | | |
|---|---|---|---|---|
| 10X Hot Star Buffer | 1X | | | |
| dNTP | 200 µM | 94° C. | 15 min | |
| Forward primer | 200 nM | 94° C. | 20 s | |
| Reverse primer | 200 nM | Specific annealing temperature | 30 s | 45 cycles |
| Hot Star Taq | 0.2 unit | 72° C. | 1 min | |
| Bisulfite-converted DNA | 50 ng | | | |
| Total reaction volume | 5 µL | 72° C. | 3 min | |

Dephosphorylation

| | Volume per reaction | Thermal profile | |
|---|---|---|---|
| RNase-free water | 1.7 µL | 37° C. | 40 min |
| Shrimp alkaline phosphatase (SAP) | 0.3 µL | 85° C. | 5 min |
| Total reaction volume | 2 µL | | |
| This mixture is added to the product of the PCR amplification | | | |

In vitro transcription and Rnase A cleavage

| | Final concentration | Thermal profile | |
|---|---|---|---|
| RNase-free water | variable | 37° C. | 3 hours |
| 5X T7 Polymerase Buffer | 0.64X | | |
| T-cleavage mix (or C-cleavage) | 0.24 µL | | |
| DTT | 3.14 mM | | |
| T7 RNA & DNA Polymerase | 22 units | | |
| RNase A | 0.09 mg/mL | | |
| SAP-treated PCR product | 2 µL | | |
| Total reaction volume | 5 µL | | |

Sample conditioning

Add 20 µL water and 6 mg Clean Resin to each well in a 384-well setting. Rotate for 10 minutes and spin down for 5 minutes at 3,200 g. The samples are then ready to be dispensed onto the SpectroCHIP ® bioarray.

TABLE 14

Oligonucleotide sequences for the Marker 13A and ZFY digital PCR assays, respectively.

| Assay | Oligonucleotide | Sequences (5' to 3')(SEQ ID NO:) | PCR amplicon length (bp) |
|---|---|---|---|
| Marker 13A | Forward Primer | 5'-GAAATAAACGCCGGAACATCTTG-3' (149) | 103 bp |
| | Reverse primer | 5'-TCTCACGGAACCGTAGACTAGGAA-3' (150) | |

TABLE 14-continued

Oligonucleotide sequences for the Marker 13A and ZFY digital PCR assays, respectively.

| Assay | Oligonucleotide | Sequences (5' to 3')(SEQ ID NO:) | PCR amplicon length (bp) |
|---|---|---|---|
| | TaqMan probe (FAM) | 5'-FAM-ACAGAGCAGGAAGCCGATGTGACTGC-BHQ1-3' (151) | |
| ZFY | Forward Primer | 5'-CAAGTGCTGGACTCAGATGTAACTG-3'(143) | 87 bp |
| | Reverse primer | 5'-TGAAGTAATGTCAGAAGCTAAAACATCA-3'(144) | |
| | TaqMan probe (VIC) | 5'-VIC-TCTTTACCACACTGCAC-MGB-3'(145) | |

NOTE:
FAM is 6-carboxyfluorescein,
VIC is Applied Biosystems ® proprietary dye,
BHQ1 is Black-hole quencher 1, and
MGB is minor groove binding.

What is claimed is:

1. A method for detecting a chromosomal aneuploidy in a fetus carried by a pregnant woman, comprising the steps of:
   (a) determining in a biological sample taken from the pregnant woman the amount of a methylation marker of fetal origin, wherein the methylation marker is located on a chromosome relevant to the chromosomal aneuploidy or within a section of a chromosome relevant to the chromosomal aneuploidy, and wherein the methylation marker of fetal origin is distinguished from its counterpart of maternal origin due to differential DNA methylation, wherein the biological sample is maternal whole blood, serum, plasma, amniotic fluid, genital tract lavage fluid, placental-tissue sample, chorionic villus sample, or a sample containing fetal cells isolated from maternal blood;
   (b) determining the amount of a genetic marker of fetal origin in the sample, wherein the genetic marker is located on a reference chromosome, and wherein the genetic marker of fetal origin is distinguished from its counterpart of maternal origin in the sample due to difference in polynucleotide sequence, or the genetic marker does not exist in the maternal genome;
   (c) determining the ratio of the amounts from (a) and (b);
   (d) comparing the ratio with a standard control;
   (e) detecting the ratio to be higher or lower than the standard control; and
   (f) detecting the presence of a chromosomal aneuploidy in the fetus carried by the woman.

2. The method of claim 1, wherein the methylation marker of fetal origin is from the placenta.

3. The method of claim 1, wherein the counterpart of maternal origin is from the pregnant woman's blood cells.

4. The method of claim 1, wherein the methylation marker of fetal origin is more methylated than its counterpart of maternal origin.

5. The method of claim 1, wherein the methylation marker of fetal origin is less methylated than its counterpart of maternal origin.

6. The method of claim 1, wherein the sample contains fetal nucleic acids.

7. The method of claim 1, wherein the methylation marker is a part of, or in proximity to, the *Holocarboxylase Synthetase* (HLCS) gene.

8. The method of claim 7, wherein the methylation marker is the putative promoter of the HLCS gene.

9. The method of claim 1, wherein the methylation marker is Marker 18A or Marker 13A.

10. The method of claim 1, wherein step (a) comprises treating the sample with a reagent that differentially modifies methylated and unmethylated DNA.

11. The method of claim 10, wherein the reagent comprises bisulfite or a protein or chemical that binds to DNA based on methylation status.

12. The method of claim 10, wherein the reagent comprises an enzyme that preferentially cleaves methylated DNA.

13. The method of claim 10, wherein the reagent comprises an enzyme that preferentially cleaves unmethylated DNA.

14. The method of claim 1, wherein the genetic marker does not exist in the maternal genome.

15. The method of claim 14, wherein the genetic marker is located on the Y chromosome.

16. The method of claim 1, wherein the genetic marker of fetal origin is distinguished from the genetic marker of maternal origin due to genetic polymorphism.

17. The method of claim 16, wherein the polymorphism comprises a single nucleotide polymorphism (SNP), simple tandem repeat polymorphism, or insertion-deletion polymorphism.

18. The method of claim 1, wherein the genetic marker is the Zinc-Finger protein, Y-linked (ZFY) gene.

19. The method of claim 1, wherein the genetic marker comprises SNP rs6636 in TMED8 gene.

20. The method of claim 1, wherein more than one methylation marker or genetic marker is used.

21. The method of claim 1, wherein step (a) or (b) comprises amplification of the methylation marker or genetic marker.

22. The method of claim 21, wherein the amplification is by a polymerase chain reaction (PCR).

23. The method of claim 22, wherein the PCR is a methylation-specific PCR.

24. The method of claim 21, wherein the amplification is a nucleic acid sequence-specific amplification.

25. The method of claim 1, wherein step (a) or (b) is performed by molecular counting.

26. The method of claim 1, wherein step (a) or (b) comprises digital polymerase chain reaction, real-time quantitative polymerase chain reaction, array capture, a nucleic acid sequence-based detection, massively parallel genomic sequencing, single molecule sequencing, or multiplexed detection of polynucleotide with color-coded probe pairs.

27. The method of claim 1, wherein step (a) or (b) comprises mass spectrometry or hybridization to a microarray, fluorescence probe, or molecular beacon.

28. The method of claim 1, wherein the chromosome relevant to the chromosomal aneuploidy is chromosome 13, 18, 21, or X.

29. The method of claim 1, wherein the ratio being higher or lower than the standard control by at least 1 standard deviation indicates the presence of the chromosomal aneuploidy in the fetus.

30. The method of claim 1, wherein the ratio being higher or lower than the standard control by at least 2 standard deviations indicates the presence of the chromosomal aneuploidy in the fetus.

31. The method of claim 1, wherein the ratio being higher or lower than the standard control by at least 3 standard deviations indicates the presence of the chromosomal aneuploidy in the fetus.

* * * * *